(12) United States Patent
Kawchuk et al.

(10) Patent No.: US 6,608,245 B1
(45) Date of Patent: Aug. 19, 2003

(54) TOMATO NUCLEIC ACID SEQUENCES THAT CONFER RESISTANCE TO VERTICILLIUM AND PLANTS TRANSFORMED THEREWITH

(75) Inventors: Lawrence M. Kawchuk, Coaldale (CA); Dermot R. Lynch, Lethbridge (CA); John Hachey, Lethbridge (CA); Frank Kulcsar, Coaldale (CA)

(73) Assignee: Her Majesty the Queen in right of Canada, as represented by the Minister of Agriculture and Agri-Food, Lethbridge (CA)

(*) Notice: Subject to any disclaimer, the term of this patent is extended or adjusted under 35 U.S.C. 154(b) by 0 days.

(21) Appl. No.: 09/513,505

(22) Filed: Feb. 25, 2000

Related U.S. Application Data

(60) Provisional application No. 60/124,129, filed on Mar. 12, 1999, and provisional application No. 60/130,586, filed on Apr. 22, 1999.

(51) Int. Cl.[7] ............................. A01H 5/00; A01H 5/10; C12N 5/04; C12N 15/29; C12N 15/82; C12N 5/10
(52) U.S. Cl. ................. 800/317.2; 800/301; 800/317; 800/279; 435/320.1; 435/419; 536/23.6
(58) Field of Search ..................... 536/23.6; 800/279, 800/301, 287, 317.4, 313, 317.2, 306, 314, 317.3, 317, 317.1, 307, 323; 435/468, 418, 419, 320.1

(56) References Cited

U.S. PATENT DOCUMENTS

| | | | |
|---|---|---|---|
| 4,407,956 A | 10/1983 | Howell | 435/172 |
| 5,859,339 A | 1/1999 | Ronald et al. | 800/205 |
| 5,920,000 A | 7/1999 | Jones et al. | 800/301 |
| 6,225,532 B1 * | 5/2001 | Dixon et al. | 800/301 |

FOREIGN PATENT DOCUMENTS

| | | | |
|---|---|---|---|
| WO | WO 96/35790 | 11/1996 | C12N/15/29 |
| WO | WO 97/43429 | 11/1997 | C12N/15/82 |

OTHER PUBLICATIONS

Kawchuk et al (1998) Identification of a dominant gene in potato conferring resistance to verticullum wilt. Can. J. Plant Path. 20:123.*

Tabaeizadeh et al (1997) Transgenic tomato plants expressing *L. chilense* chitinase gene demonstrate resistance to *verticillum dahliae*. Plant Phys. 114:299.*

Maiti, I. B. et al., "Promoter/leader deletion analysis and plant expression vectors with the figwort mosaic virus (FMV) full length transcript (FLt) promoter containing single or double enhancer domains." 1997, Transgenic Research, vol. 6, pp. 143–156.*

Neuhaus, J. et al., "High–level expression of a tobacco chitinase gene in *Nicotiana sylvestris*. Susceptibility of transgenic plants to *Cercospora nicotianae* infection." 1991, Plant Molecular Biology, vol. 16, pp. 141–151.*

Hill, M. A. and Preiss, J. "Functional Analysis of Conserved Histidines in ADP–Glucose Pyrophosphorylase from *Escherichia coli*." 1998, Biochemical and Biophysical Res. Comm., vol. 244, pp. 573–577.*

Broun, P. et al., "Catalytic Plasticity of Fatty Acid Modification Enzymes Underlying Chemical Diversity of Plant Lipids." 1998, Science, vol. 282, pp. 1315–1317.*

Bowie, J. U. et al., "Deciphering the Message in Protein Sequences: Tolerance to Amino Acid Substitutions."1990, Science, vol. 247, pp. 1306–1310.*

Lazar, E. et al., "Transforming Growth Factor a: Mutation of Aspartic Acid 47 and Leucine 48 Results in Different Biological Activities." 1988, Molecular and Cellular Biology, vol. 8, pp. 1247–1252.*

Kawchuk, L. M. et al., "Tomato Ve disease resistance genes encode cell surface–like receptors." 2001, PNAS, vol. 98, pp. 6511–6515.*

D'Ascenzo, M. et al. (Jun. 30, 1999) EST 259460 tomato susceptible, Cornell *Lycopersicon esculentum* cDNA clone cLES5D14, mRNA Sequence. EMBL Accession NoA1778581.

Wu, Gusui et al. (1997) Activation of host defense mechanisms by elevated production of $H_2O_2$ in transgenic plants. *Plant Physiology* vol. 115:427–435.

Alber, Tom and Kawasaki, Glenn. 1982. Nucleotide Sequence of the Triose Phosphate Isomerase Gene of *Saccharomyces cerevisiae*. Journal of Molecular and Applied Genetics. 1:419–434.

Altschul, Stephen F., et al. 1990. Basic Local Alignment Search Tool. J. Mol. Biol. 215:403–410.

Altschul, Stephen F., et al. 1997. Gapped BLAST and PSI–BLAST: a new generation of protein database search programs. Nucleic Acids Research. vol. 25, No. 17:3389–3402.

Bent, Andrew F., et al. 1994. RPS2 of *Arabidopsis thaliana*: A leucine–Rich Repeat Class of Plant Disease Resistance Genes. Science. vol. 265:1856–1860.

Bilang, Roland, et al. 1994. PEG–mediated direct gene transfer and electroporation. Plant Molecular Biology Manual. A1:1–16.

(List continued on next page.)

Primary Examiner—Amy J. Nelson
Assistant Examiner—Anne Kubelik
(74) Attorney, Agent, or Firm—Greenlee Winner and Sullivan, PC

(57) ABSTRACT

The invention provides tomato polynucleotides which, when transformed into a plant, confer on the plant resistance to Verticillium species. The polynucleotides of the invention are useful for producing transgenic plants that are resistant to Verticillium species.

22 Claims, 18 Drawing Sheets

OTHER PUBLICATIONS

De Block, M. 1988. Genotype–independent leaf disc transformation of potato (*Solanum tuberosum*) using *Agrobacterium tumefaciens*. Theor. Appl Genet. 76:767–774.

Depicker, A., et al. 1982. Nopaline Synthase: Transcript Mapping and DNA Sequence. Journal of Molecular and Applied Genetics. 561–573.

Diwan, N., et al. 1999. Mapping of Ve in tomato: a gene conferring resistance of the broad–spectrum pathogen, *Verticillium dahliae* race 1. Theor Appl Genet. 98:315–319.

Dixon, Mark S., et al. 1998. The Tomato Cf–5 Disease Resistance Gene and Six Homologs Show Pronounced Allelic Variation in Leucine–Rich Repeat Copy Number. The Plant Cell. vol. 10, 1915–1925.

Domsch, K. H., et al. 1980. Compendium of Soil Fungi. Academic Press London. 828–845.

Flor, H.H. 1946. Genetics of Pathogenicity in *Melampsora Lini*. Journal of Agricultural Research. vol. 73:335–357.

Gardina, Paul J., et al. 1996. Attractant Signaling by an Aspartate Chemoreceptor Dimer with a Single Cytoplasmic Domain. Science. vol. 274:425–426.

Gielen, J., et al. 1984. The complete nucleotide sequence of the TL–DNA of the *Agrobacterium tumefaciens* plasmid pTiAch5. EMBO Journal. vol. 3, No. 4:835–846.

Grant, Murray R., et al. 1995. Structure of the Arabidopsis RPM1 Gene Enabling Dual Specificity Disease Resistance. Science. vol. 269:843–846.

Hammond–Kosack, Kim E., et al. 1997. Plant Disease Resistance Genes. Annu. Rev. Plant Physiol. Plant Mol. Biol. 48:575–607.

Ihle, James N. 1995. Cytokine receptor signalling. Nature. vol. 377:591–594.

Jackson, Michael R., et al. 1990. Identification of a consensus motif for retention of transmembrane proteins in the endoplasmic reticulum. EMBO Journal. vol. 9, No. 10:3153–3162.

Johal, Gurmukh and Briggs, Steven P. 1992. Reductase Activity Encoded by the HM1 Disease Resistance Gene in Maize. Science. vol. 258:985–987.

Jones, David A., et al. 1994. Isolation of the Tomato Cf–9 Gene for Resistance to *Cladosporium fulvum* by Transposon Tagging. Science. vol. 266:789–793.

Kawchuk, L.M., et al. 1998. Development of sequence characterised DNA markers linked to a dominant verticillium wilt resistance gene in tomato. Genome. 41:91–95.

Kawchuk, L.M., et al. 1994. Identification of a codominant amplified polymorphic DNA marker linked to the verticillium wilt resistance gene in tomato. Theor Appl Genet. 89:661–664.

Lawrence, Gregory J., et al. 1995. The L6 Gene for Flax Rust Resistance is Related to the Arabidopsis Bacterial Resistance Gene RPS2 and the Tobacco Viral Resistance Gene N. The Plant Cell. vol. 7:1195–1206.

Leister, Dario, et al. 1996. A PCT–based approach for isolating pathogen resistance genes from potato with potential for wide application in plants.

Livnah, Oded, et al. 1999. Crystallographic Evidence for Preformed Dimer of Erythropoietin Receptor Before Ligand Activation. Science. vol. 283:987–990.

Lynch, D. R., et al. 1997. Identification of a Gene Conferring High Levels of Resistance to Verticillium Wilt in *Solanum chacoense*. Plant Disease. vol. 81, No. 9:1011–1014.

Martin, Gregory B., et al. 1993. Map–Based Cloning of a Protein Kinase Gene Conferring Disease Resistance in Tomato. Science. vol. 262:1432–1436.

Milligan, Stephen B., et al. 1998. The Root Knot Nematode Resistance Gene Mi from Tomato Is a Member of the Leucine Zipper, Nucleotide Binding, Leucine–Rich Repeat Family of Plant Genes. Plant Cell. vol. 10:1307–1320.

Mindrinos, Mciahel, et al. 1994. The *A. Thaliana* Disease Resistance Gene RPS2 Encodes a Protein Containing a Nucleotide–Binding Site and Leucine–Rich Repeats. Cell. vol. 78:1089–1099.

Ori, Naomi, et al. 1997. The /2C Family from the Wilt Disease Resistance Locus /2 Belongs to the Nucleotide Binding, Leucine–Rich Repeat Superfamily of Plant Resistance Genes. Plant Cell. vol. 9:521–532.

Remy, Ingrid, et al. 1999. Erythropoietin Receptor Activation by a Ligand–Induced Conformation Change. Science. vol. 283:990–993.

Rogers, Scott, et al. 1986. Amino Acid Sequences Common to Rapidly Degraded Proteins: The PEST Hypothesis. Science. vol. 234: 364–368.

Rommens, Calus M. T., et al. 1995. Intergeneric Transfer and Functional Expression of the Tomato Disease Resistance Gene Pto. Plant Cell. vol. 7:1537–1544.

Rossi, Magdalena, et al. 1998. The nematode resistance gene Mi of tomato confers resistance against the potato aphid. Proc. Natl. Acad. Sci. USA. vol. 95:9750–9754.

Sambrook, J., et al. 1989. Molecular Cloning, A Laboratory Manual. Cold Spring Harbor Laboratory Press. pp. 387–389.

Schaible, Lester, et al. 1951. Inhertitance of Resistance to Verticillium Wilt in a Tomato Cross. Phytopathology. vol. 41:986–990.

Simons, Guus, et al. 1998. Dissection of the Fusarium /2 Gene Cluster in Tomato Reveal Six Homologs and One Active Gene Copy. Plant Cell. vol. 10:1055–1068.

Song, Nen–Yuan, et al. 1995. A Receptor Kinase–Like Protein Encoded by the Rice Disease Resistance Gene, Xa21. Science. vol. 270:1804–1806.

Staebell, Mark, et al. A Quantitative Assay for Neomycin Phosphotransferase Activity in Plants. Analytical Biochemistry. vol. 185: 319–323.

Thilmony, Roger L., et al. 1995. Expression of the Tomato Pto Gene in Tobacco Enhances Resistance to *Pseudomonas syringae* pv tabaci Expressing avrPto. Plant Cell. vol. 7:1529–1536.

von Heijne, Gunnar. 1985. Signal Sequences. The Limits of Variation. J. Mol. Biol. vol. 184:99–105.

Vos, Pieter, et al. 1998. The tomato Mi–1 gene confers resistance to both root–knot nematodes and potato aphids. Nature Biotechnology. vol. 16:1365–1369.

Wang, Guo–Liang, et al. 1998. Xa21D Encodes a Receptor–like Molecule with a Leucine–Rich Repeat Domain That Determines Race–Specific Recognition and Is Subject to Adaptive Evolution. Plant Cell. vol. 10:765–779.

Whitham, Steve, et al. 1996. The N gene of tobacco confers resistance to tobacco mosaic virus in transgenic tomato. Proc. Natl. Acad. Sci. USA. vol. 93:8776–8781.

\* cited by examiner

Fig. 2A

*Ve1.1* genomic DNA

```
ATGAGATTTTTACACTTTCTATGGATCTTCTTCATCATACCCTTTTTGCAAATTTTATTAGG
TAATGAGATTTTATTGGTTTCCTCTCAATGTCTTGATGATCAAAAGTCATTGTTGCTGCAGT
TGAAGGGCAGCTTCCAATATGATTCTACTTTGTCAAATAAATTGGCAAGATGGAACCACAAC
ACAAGTGAATGTTGTAACTGGAATGGGGTTACATGTGACCTCTCTGGTCATGTGATTGCCTT
GGAACTGGATGATGAGAAAATTTCTAGTGGAATTGAGAATGCAAGTGCTCTTTTCAGTCTTC
AGTATCTTGAGAGGCTAAATTTGGCTTACAACAAGTTCAATGTTGGCATACCAGTTGGTATA
GGCAACCTCACCAACTTGACGTACCTGAATTTATCCAATGCCGGTTTTGTTGGCCAAATTCC
TATGATGTTATCAAGGTTAACAAGGCTAGTTACTCTTGATCTCTCAACTCTTTTCCCTGACT
TTGCCCAGCCACTAAAACTAGAGAATCCCAATTTGAGTCATTTCATTGAGAACTCAACAGAG
CTTAGAGAGCTTTACCTTGATGGGGTTGATCTCTCAGCTCAGAGGACTGAGTGGTGTCAATC
TTTATCTTCATATTTGCCTAACTTGACTGTCTTGAGCTTGCGTACTTGTCGAATTTCAGGCC
CTATTGATGAATCACTTTCTAAGCTTCACTTTCTCTCTTTCATCCGTCTTGACCAGAACAAT
CTCTCTACCACAGTTCCTGAATACTTTGCCAATTTCTCAAACTTGACTACCTTGACCCTCTC
CTCTTGTAATCTGCAAGGAACATTTCCTAAAAGAATCTTTCAGGTACCAGTCTTAGAGTTTT
TGGACTTGTCAACTAACAAATTGCTTAGTGGTAGTATTCCGATTTTTCCTCAAATTGGATCA
TTGAGGACGATATCACTAAGCTACACCAAGTTTTCTGGTTCATTACCAGACACCATTTCGAA
CCTTCAAAACCTATCCAGGTTAGAACTCTCCAACTGCAATTTCAGTGAACCAATACCTTCCA
CAATGGCGAACCTTACCAATCTTGTTTATTTAGATTTCTCCTTCAACAATTTCACTGGTTCC
CTCCCATATTTCCAAGGGGCCAAGAAACTCATCTACTTGGACCTTTCACGTAATGGTCTAAC
TGGTCTCTTGTCTAGAGCTCATTTTGAAGGACTCTCAGAACTTGTCTACATTAATTTAGGGA
ACAATTCACTCAACGGGAGCCTTCCTGCATATATATTTGAGCTCCCCTCGTTGAAGCAGCTT
TTTCTTTACAGCAATCAATTTGTTGGCCAAGTCGACGAATTTCGCAATGCATCCTCCTCTCC
GTTGGATACAGTTGACTTGAGAAACAACCACCTGAATGGATCGATTCCCAAGTCCATGTTTG
AAGTTGGGAGGCTTAAGGTCCTCTCACTTTCTTCCAACTTCTTTAGAGGGACAGTTCCCCTT
GACCTCATTGGGAGGCTGAGCAACCTTTCAAGACTGGAGCTTTCTTACAATAACTTGACTGT
TGATGCAAGTAGCAGCAATTCAACCTCTTTCACATTTCCCCAGTTGAACATATTGAAATTAG
CGTCTTGTCGGCTGCAAAAGTTCCCCGATCTCAAGAATCAGTCAAGGATGATGCACTTAGAC
CTTTCAGACAACCAAATATTGGGGCAATACCAAATTGGATCTGGGGAATTGGTGGTGGAGG
TCTCGCCCACCTGAATCTTTCATTCAATCAGCTGGAGTACGTGGAACAGCCTTACACTGTTT
CCAGCAATCTTGCAGTCCTTGATTTGCATTCCAACCGTTTAAAAGGTGACTTACTAATACCA
CCTTCCACTGCCATCTATGTGGACTACTCGAGCAATAATTTAAACAATTCCATCCCAACAGA
TATTGGAAGATCTCTTGGTTTTGCCTCCTTTTCTCGGTAGCAAACAATAGCATCACTGGAA
TAATTCCTGAATCCATATGCAACGTCAGCTACCTTCAAGTTCTTGATTTCTCTAACAATGCC
TTGAGTGGAACAATACCACCATGTCTACTGGAATATAGTCCAAAACTTGGAGTGCTGAATCT
AGGGAACAATAGACTCCATGGTGTTATACCAGATTCATTTCCAATTGGTTGTGCTCTAATAA
CTTTAGACCTCAGCAGGAATATCTTTGAAGGGAAGCTACCAAAATCGCTTGTCAACTGCACG
TTGTTGGAGGTCCTGAATGTTGGAAATAACAGTCTTGTTGATCGTTTCCCATGCATGTTGAG
GAACTCAACCAGCCTGAAGGTCCTAGTCTTGCGCTCCAATAAATTCAATGGAAATCTTAC
```

Fig. 2B

```
GTGTAATATAACCAAACATAGCTGGAAGAATCTCCAGATCATAGATATAGCTTCCAACAATT
TTACTGGTATGTTGAATGCAGAATGCTTTACAAATTGGAGAGGAATGATGGTTGCAAAAGAT
TACGTGGAGACAGGACGCAATCATATCCAGTATGAGTTCTTACAACTAAGTAACTTGTACTA
TCAGGATACAGTGACATTAATCATCAAAGGCATGGAGCTGGAGCTTGTGAAGATTCTTAGGG
TCTTCACATCTATTGATTTCTCTTCCAATAGATTTCAAGGAAAGATACCAGATACTGTTGGG
GATCTTAGCTCACTTTATGTTTTGAACCTGTCACACAATGCCCTCGAGGGACCAATTCCAAA
ATCAATTGGGAAGCTACAAATGCTTGAATCACTAGACCTGTCAACAAACCACCTGTCCGGGG
AGATCCCCTCAGAGCTTTCAAGTCTCACATTCTTAGCAGTTTTGAACTTATCGTTCAACAAT
TTGTTTGGAAAAATCCCGCAAAGTAATCAATTTGAAACATTCCCAGCAGAATCCTTTGAAGG
AAACAGAGGCCTATGCGGGCTTCCTCTTAACGTCATTTGCAAAAGCGATACTTCAGAGTTGA
AACCAGCACCAAGTTCTCAAGATGACTCTTATGATTGGCAGTTCATATTTACGGGTGTGGGA
TATGGAGTAGGGCAGCAATCTCCATTGCACCTCTGTTGTTTTACAAGCAAGGAAACAAATA
CTTTGACAAACATTTGGAGAGAATGCTTAAACTGATGTTTCCTAGATACTGGTTCAGTTACA
CCAGATTTGACCCTGGGAAGGTTGTGGCTGTGGAACACTATGAAGATGAGACCCCAGATGAC
ACCGAAGATGACGATGAGGGGGGAAAAGAAGCATCTCTTGGGCGTTATTGTGTCTTCTGTAG
TAAACTTGATTTTCAGAAAAATGAAGCAATGCATGATCCAAAATGCACTTGTCATATGTCAT
CATCCCCCAATTCTTTTCCTCCTACGCCGTCCTCTTCTTCACCTTTATTAGTCATATATCAC
AAAAAGTTTTGA
```

Fig. 3A

*Ve1.1* cDNA

```
GCACGAGAGAAAAAACAACAAGTTTGATGGATTATAATTCCTCCAAGACTTAAGCAATGAGA
TTTTTACACTTTCTATGGATCTTCTTCATCATACCCTTTTTGCAAATTTTATTAGGTAATGA
GATTTTATTGGTTTCCTCTCAATGTCTTGATGATCAAAAGTCATTGTTGCTGCAGTTGAAGG
GCAGCTTCCAATATGATTCTACTTTGTCAAATAAATTGGCAAGATGGAACCACAACACAAGT
GAATGTTGTAACTGGAATGGGGTTACATGTGACCTCTCTGGTCATGTGATTGCCTTGGAACT
GGATGATGAGAAAATTTCTAGTGGAATTGAGAATGCAAGTGCTCTTTTCAGTCTTCAGTATC
TTGAGAGGCTAAATTTGGCTTACAACAAGTTCAATGTTGGCATACCAGTTGGTATAGGCAAC
CTCACCAACTTGACGTACCTGAATTTATCCAATGCCGGTTTTGTTGGCCAAATTCCTATGAT
GTTATCAAGGTTAACAAGGCTAGTTACTCTTGATCTCTCAACTCTTTTCCCTGACTTTGCCC
AGCCACTAAAACTAGAGAATCCCAATTTGAGTCATTTCATTGAGAACTCAACAGAGCTTAGA
GAGCTTTACCTTGATGGGGTTGATCTCTCAGCTCAGAGGACTGAGTGGTGTCAATCTTTATC
TTCATATTTGCCTAACTTGACTGTCTTGAGCTTGCGTACTTGTCGAATTTCAGGCCCTATTG
ATGAATCACTTTCTAAGCTTCACTTTCTCTCTTTCATCCGTCTTGACCAGAACAATCTCTCT
ACCACAGTTCCTGAATACTTTGCCAATTTCTCAAACTTGACTACCTTGACCCTCTCCTCTTG
TAATCTGCAAGGAACATTTCCTAAAAGAATCTTTCAGGTACCAGTCTTAGAGTTTTTGGACT
TGTCAACTAACAAATTGCTTAGTGGTAGTATTCCGATTTTTCCTCAAATTGGATCATTGAGG
ACGATATCACTAAGCTACACCAAGTTTTCTGGTTCATTACCAGACACCATTTCGAACCTTCA
AAACCTATCCAGGTTAGAACTCTCCAACTGCAATTTCAGTGAACCAATACCTTCCACAATGG
CGAACCTTACCAATCTTGTTTATTTAGATTTCTCCTTCAACAATTTCACTGGTTCCCTCCCA
TATTTCCAAGGGGCCAAGAAACTCATCTACTTGGACCTTTCACGTAATGGTCTAACTGGTCT
CTTGTCTAGAGCTCATTTTGAAGGACTCTCAGAACTTGTCTACATTAATTTAGGGAACAATT
CACTCAACGGGAGCCTTCCTGCATATATATTTGAGCTCCCCTCGTTGAAGCAGCTTTTTCTT
TACAGCAATCAATTTGTTGGCCAAGTCGACGAATTTCGCAATGCATCCTCCTCTCCGTTGGA
TACAGTTGACTTGAGAAACAACCACCTGAATGGATCGATTCCCAAGTCCATGTTTGAAGTTG
GGAGGCTTAAGGTCCTCTCACTTTCTTCCAACTTCTTTAGAGGGACAGTTCCCCTTGACCTC
ATTGGGAGGCTGAGCAACCTTTCAAGACTGGAGCTTTCTTACAATAACTTGACTGTTGATGC
AAGTAGCAGCAATTCAACCTCTTTCACATTTCCCCAGTTGAACATATTGAAATTAGCGTCTT
GTCGGCTGCAAAAGTTCCCCGATCTCAAGAATCAGTCAAGGATGATGCACTTAGACCTTTCA
GACAACCAAATATTGGGGGCAATACCAAATTGGATCTGGGGAATTGGTGGTGGAGGTCTCGC
CCACCTGAATCTTTCATTCAATCAGCTGGAGTACGTGGAACAGCCTTACACTGTTTCCAGCA
ATCTTGTAGTCCTTGATTTGCATTCCAACCGTTTAAAAGGTGACTTACTAATACCACCTTCC
ACTGCCATCTATGTGGACTACTCGAGCAATAATTTAAACAATTCCATCCCAACAGATATTGG
AAGATCTCTTGGTTTTGCCTCCTTTTTCTCGGTAGCAAACAATAGCATCACTGGAATAATTC
CTGA
```

Fig. 3B

```
ATCCATATGCAACGTCAGCTACCTTCAAGTTCTTGATTTCTCTAACAATGCCTTGAGTGGAA
CAATACCACCATGTCTACTGGAATATAGTCCAAAACTTGGAGTGCTGAATCTAGGGAACAAT
AGACTCCATGGTGTTATACCAGATTCATTTCCAATTGGTTGTGCTCTAATAACTTTAGACCT
CAGCAGGAATATCTTTGAAGGGAAGCTACCAAAATCGCTTGTCAACTGCACGTTGTTGGAGG
TCCTGAATGTTGGAAATAACAGTCTTGTTGATCGTTTCCCATGCATGTTGAGGAACTCAACC
AGCCTGAAGGTCCTAGTCTTGCGCTCCAATAAATTCAATGGAAATCTTACGTGTAATATAAC
CAAACATAGCTGGAAGAATCTCCAGATCATAGATATAGCTTCCAACAATTTTACTGGTATGT
TGAATGCAGAATGCTTTACAAATTGGAGAGGAATGATGGTTGCAAAAGATTACGTGGAGACA
GGACGCAATCATATCCAGTATGAGTTCTTACAACTAAGTAACTTGTACTATCAGGATACAGT
GACATTAATCATCAAAGGCATGGAGCTGGAGCTTGTGAAGATTCTTAGGGTCTTACATCTA
TTGATTTCTCTTCCAATAGATTTCAAGGAAGATACCAGATACTGTTGGGGATCTTAGCTCA
CTTTATGTTTTGAACCTGTCACACAATGCCCTCGAGGGACCAATTCCAAAATCAATTGGGAA
GCTACAAATGCTTGAATCACTAGACCTGTCAAGAAACCACCTGTCCGGGGAGATCCCCTCAG
AGCTTTCAAGTCTCACATTCTTAGCAGTTTTGAACTTATCGTTCAACAATTTGTTTGGAAAA
ATCCCGCAAAGTAATCAATTTGAAACATTCTCAGCAGAATCCTTTGAAGGAAACAGAGGCCT
ATGCGGGCTCCCTCTTAACGTCATTTGCAAAAGCGATACTTCAGAGTTGAAACCAGCACCAA
GTTCTCAAGATGACTCTTATGATTGGCAGTTCATATTTACGGGTGTGGGATATGGAGTAGGG
GCAGCAATCTCCATTGCACCTCTGTTGTTTTACAAGCAAGGAAACAAATACTTTGACAAACA
TTTGGAGAGAATGCTTAAACTGATGTTTCCTAGATACTGGTTCAGTTACACCAGATTTGACC
CTGGGAAGGTTGTGGCTGTGGAACACTATGAAGATGAGACCCCAGATGACACCGAAGATGAC
GATGAGGGTGGAAAAGAAGCATCTCTTGGGCGTTATTGTGTCTTCTGTAGTAAACTTGATTT
TCAGAAAAATGAAGCAATGCATGATCCAAAATGCACTTGTCATATGTCATCATCCCCAATT
CTTTTCCTCCTACGCCGTCCTTTTTTTCACCTTTATTAGTCATATATCACAAAAAGTTTTGA
TT
```

Fig. 4A

Ve1.1 AA from cDNA

| | | |
|---|---|---:|
| A | MRFLHFLWIFFIIPFLQILLGNEILLVSSQ | 30 |
| B | CLDDQKSLLLQLKGSFQYDSTLSNKLA | 60 |
| | RWNHNTSECCNWNGVTCDLSGHVIALELDDEKISSGIE | 95 |
| | NASALFSLQYLERLNLAYNKFNVGIP | 121 |
| | VGIGNLTNLTYLNLSNAGFVGQIP | 145 |
| | MMLSRLTRLVTLDLSTLFPDFAQP | 169 |
| | LKLENPNLSHFIENSTELRELYLDGVDLSAQRT | 202 |
| | EWCQSLSSYLPNLTVLSLRTCRISGPID | 230 |
| | ESLSKLHFLSFIRLDQNNLSTTVP | 254 |
| | EYFANFSNLTTLTLSSCNLQGTFP | 278 |
| | KRIFQVPVLEFLDLSTNKLLSGSIP | 303 |
| | IFPQIGSLRTISLSYTKFSGSLP | 326 |
| | DTISNLQNLSRLELSNCNFSEPIP | 350 |
| | STMANLTNLVYLDFSFNNFTGSLP | 374 |
| | YFQGAKKLIYLDLSRNGLTGLLS | 397 |
| | RAHFEGLSELVYINLGNNSLNGSLP | 422 |
| | AYIFELPSLKQLFLYSNQFVGQVD | 446 |
| | EFRNASSSPLDTVDLRNNHLNGSIP | 471 |
| | KSMFEVGRLKVLSLSSNFFRGTVP | 495 |
| | LDLIGRLSNLSRLELSYNNLTVDAS | 520 |
| | SSNSTSFTFPQLNILKLASCRLQKFPD | 547 |
| | LKNQSRMMHLDLSDNQILGAIP | 569 |
| | NWIWGIGGGGLAHLNLSFNQLEYVEQ | 595 |
| | PYTVSSNLVVLDLHSNRLKGDLLIP | 620 |
| | PSTAIYVDYSSNNLNNSIP | 639 |
| | TDIGRSLGFASFFSVANNSITGIIP | 664 |
| | ESICNVSYLQVLDFSNNALSGTIP | 688 |
| | PCLLEYSPKLGVLNLGNNRLHGVIP | 713 |
| | DSFPIGCALITLDLSRNIFEGKLP | 737 |
| | KSLVNCTLLEVLNVGNNSLVDRFP | 761 |
| | CMLRNSTSLKVLVLRSNKFNGNLT | 785 |
| | CNITKHSWKNLQIIDIASNNFTGMLN | 811 |
| | AECFTNWRGMMVAKDYVETGRNHIQ | 836 |
| | YEFLQLSNLYYQDTVTLIIKG | 857 |
| | MELELVKILRVFTSIDFSSNRFQGKIP | 884 |
| | DTVGDLSSLYVLNLSHNALEGPIP | 908 |
| | KSIGKLQMLESLDLSRNHLSGEIP | 932 |
| | SELSSLTFLAVLNLSFNNLFGKIP | 959 |
| | QSNQFETFSAESFEGNRGLCGLPLNVICKSDTSE | 990 |
| C | LKPAPSSQDDSYDWQFIFTGVGYGVGAAISIA | 1022 |

Fig. 4B

| | | |
|---|---|---|
| D | PLLFY<u>KQGNKY</u>FD<u>KH</u>LE<u>R</u>MLK<u>L</u>MFP<u>RY</u>WF<u>SYTR</u>FDP<u>GK</u>VVAV | 1064 |
| E | EHY<u>EDET</u>P<u>DD</u>TE<u>DDDE</u>GG | 1082 |
| F | KEASLGRYCVFCSKLDFQKNEAMHDPKCTC | 1112 |
| | HMSSSPNSFPPTPSFFSPLLVIYHKKF | 1139 |

Fig. 5A

*Ve1.2* genomic DNA

```
ATGAAAATGATGGCAACTCTGTACTTCCCTATGGTTCTCTTGATTCCCTCGTTTCAAATCTT
ATCAGGATACCACATTTTCTTGGTTTCCTCTCAATGCCTTGACGATCAAAAGTCATTGTTGC
TGCAGTTTAAGGGAAGCCTCCAATATGATTCTACTTTGTCAAAGAAATTGGCAAAATGGAAC
GACATGACAAGTGAATGTTGCAATTGGAATGGGGTTACATGCAATCTCTTTGGTCATGTGAT
CGCTTTGGAACTGGATGATGAGACTATTTCTAGTGGAATTGAGAATTCTAGTGCACTTTTCA
GTCTTCAATATCTTGAGAGCCTAAATTGGCTGACAACATGTTCAATGTTGGCATACCAGTT
GGTATAGACAACCTCACAAACTTGAAGTACCTGAATTTATCCAATGCTGGTTTTGTCGGGCA
AATTCCTATAACATTATCAAGATTAACAAGGCTAGTTACTCTTGATCTCTCAACTATTCTCC
CTTTTTTTGATCAGCCACTTAAACTTGAGAATCCCAATTTGAGTCATTTCATTGAGAACTCA
ACAGAGCTTAGAGAGCTTTACCTTGATGGGGTTGATCTTTCGTCTCAGAGGACTGAGTGGTG
TCAATCTTTATCTTTACATTTGCCTAACTTGACCGTTTTGAGCTTGCGTGATTGTCAAATTT
CAGGCCCTTTGGATGAATCACTTTCTAAGCTTCACTTTCTCTCTTTTGTCCAACTTGACCAG
AACAATCTCTCTAGCACAGTTCCTGAATATTTTGCCAATTTCTCGAACTTGACTACATTGAC
CCTGGGCTCTTGTAATCTACAGGGAACATTTCCTGAAAGAATCTTTCAGGTATCAGTTTTAG
AGAGTTTGGACTTGTCAATTAACAAGTTGCTTCGTGGTAGTATTCCAATTTTTTTCCGAAAT
GGATCTCTGAGGAGGATATCACTAAGCTACACCAACTTTTCCGGTTCATTACCAGAGTCCAT
TTCGAACCATCAAAATCTATCCAGGTTAGAGCTTTCTAATTGCAATTTCTATGGATCAATAC
CTTCCACAATGGCAAACCTTAGAAATCTTGGTTATTTGGATTTCTCCTTCAACAATTTCACT
GGTTCTATCCCATATTTTCGACTGTCCAAGAAACTCACCTACTTAGACCTTTCACGTAATGG
TCTAACTGGTCTCTTGTCTAGAGCTCATTTTGAAGGACTCTCAGAGCTTGTCCACATTAATT
TAGGGAACAATTTACTCAGCGGGAGCCTTCCTGCATATATATTTGAGCTCCCCTCGTTGCAG
CAGCTTTTTCTTTACAGAAATCAATTTGTTGGCCAAGTCGACGAATTTCGCAATGCATCCTC
CTCTCCGTTGGATACAGTTGACTTGACAAACAACCACCTGAATGGATCGATTCCGAAGTCCA
TGTTTGAAATTGAAAGGCTTAAGGTGCTCTCACTTTCTTCCAACTTCTTTAGAGGGACAGTG
CCCCTTGACCTCATTGGGAGGCTGAGCAACCTTTCAAGACTGGAGCTTTCTTACAATAACTT
GACTGTTGATGCAAGTAGCAGCAATTCAACCTCTTTCACATTTCCCCAGTTGAACATATTGA
AATTAGCGTCTTGTCGGCTGCAAAAGTTCCCCGATCTCAAGAATCAGTCATGGATGATGCAC
TTAGACCTTTCAGACAACCAAATATTGGGGGCAATACCAAATTGGATCTGGGGAATTGGTGG
TGGAGGTCTCACCCACCTGAATCTTTCATTCAATCAGCTGGAGTACGTGGAACAGCCTTACA
CTGCTTCCAGCAATCTTGTAGTCCTTGATTTGCATTCCAACCGTTTAAAAGGTGACTTACTA
ATACCACCTTGCACTGCCATCTATGTGGACTACTCTAGCAATAATTTAAACAATTCCATCCC
AACAGATATTGGAAAGTCTCTTGGTTTTGCCTCCTTTTTCTCGGTAGCAAACAATGGCATTA
CTGGAATAATTCCTGAATCCATATGCAACTGCAGCTACCTTCAAGTTCTTGATTTCTCTAAC
AATGCCTTGAGTGGAACAATACCACCATGTCTACTGGAATATAGTACAAAACTTGGAGTGCT
GAATCTTGGGAACAATAAACTCAATGGTGTTATACCAGATTCATTTTCAATTGGTTGTGCTC
TACAAACATTAGACCTCAGTGCGAATAACTTACAAGGCAGGCTGCCAAAATCGATTGTGAAT
TGTAAGTTGTTGGAGGTCCTGAATGTTGGAAATAACAGACTTGTTGATCATTTCCCATGCAT
GTTGAGGAACTCAAACAGTCTGAGGGTCCTAGTCTTGCGCTCCAATAAATTCTATGGAAATC
TTATGTGTGATGTAACCAGAAATAGCTGGCAGAATCTCCAGATCATAGATATAGCTTCCAAC
AACTTCACTGGTGTGTTAATGCAGAATTCTTTTCAAATTGGAGAGGAATGATGGTTGCAGA
TGATTACGTGGAGACAGGACGCAATCATATCCAGTATGAGTTCTTACAACTAAGT
```

Fig. 5B

```
AAATTGTACTATCAGGACACAGTGACATTAACCATCAAAGGCATGGAGCTGGAGCTTGTGAA
GATTCTCAGGGTCTTCACATCTATTGATTTCTCTTCCAATAGATTTCAAGGAGCGATACCAG
ATGCTATCGGGAATCTCAGCTCACTTTATGTTCTGAATCTGTCACACAATGCCCTTGAGGGA
CCAATCCCAAAATCGATTGGGAAGCTACAAATGCTTGAATCACTAGACCTGTCAACAAACCA
CCTGTCCGGGGAGATCCCATCAGAGCTTGCAAGTCTCACATTCTTAGCAGCTTTGAACTTAT
CGTTCAACAAATTGTTTGGCAAAATTCCATCAACTAATCAGTTTCAAACATTCTCAGCAGAT
TCCTTTGAAGGAAACAGTGGCCTATGCGGGCTCCCTCTCAACAACAGTTGTCAAAGCAATGG
CTCAGCCTCAGAGTCCCTGCCTCCACCAACTCCGCTACCAGACTCAGATGATGAATGGGAGT
TCATTTTTGCAGCAGTTGGATACATAGTAGGGGCAGCAAATACTATTTCAGTTGTGTGGTTT
TACAAGCCAGTGAAGAAATGGTTTGATAAGCATATGGAGAAATGCTTGCTTTGGTTTTCAAG
AAAGTGA
```

Fig. 6A

*Vel.2* cDNA

ATGAAAATGATGGCAACTCTGTACTTCCCTATGGTTCTCTTGATTCCCTCGTTTCAAATCTT
ATCAGGATACCACATTTTCTTGGTTTCCTCTCAATGCCTTGACGATCAAAAGTCATTGTTGC
TGCAGTTTAAGGGAAGCCTCCAATATGATTCTACTTTGTCAAAGAAATTGGCAAAATGGAAC
GACATGACAAGTGAATGTTGCAATTGGAATGGGGTTACATGCAATCTCTTTGGTCATGTCAT
CGCTTTGGAACTGGATGATGAGACTATTTCTAGTGGAATTGAGAATTCTAGTGCACTTTTCA
GTCTTCAATATCTTGAGAGCCTAAATTTGGCTGACAACATGTTCAATGTTGGCATACCAGTT
GGTATAGACAACCTCACAAACTTGAAGTACCTGAATTTATCCAATGCTGGTTTTGTCGGGCA
AATTCCTATAACATTATCAAGATTAACAAGGCTAGTTACTCTTGATCTCTCAACTATTCTCC
CTTTTTTTGATCAGCCACTTAAACTTGAGAATCCCAATTTGAGTCATTTCATTGAGAACTCA
ACAGAGCTTAGAGAGCTTTACCTTGATGGGGTTGATCTTTCGTCTCAGAGGTCTGAGTGGTG
TCAATCTTTATCTTTACATTTGCCTAACTTGACCGTTTTGAGCTTGCGTGATTGTCAAATTT
CAGGCCCTTTGGATGAATCACTTACTAAGCTTCACTTTCTCTCTTTTGTCCAACTTGACCAG
AACAATCTCTCTAGCACAGTTCCTGAATATTTTGCCAATTTCTCGAACTTGACTACATTGAC
CCTGGGCTCTTGTAATCTACAGGGAACATTTCCTGAAAGAATCTTTCAGGTATCAGTTTTAG
AGAGTTTGGACTTGTCAATTAACAAGTTGCTTCGTGGTAGTATTCCAATTTTTTTCCGAAAT
GGATCTCTGAGGAGGATATCACTAAGCTACACCAACTTTTCCGGTTCATTACCAGAGTCCAT
TTCGAACCATCAAAATCTATCCAGGTTAGAGCTTTCTAATTGCAATTTCTATGGATCAATAC
CTTCCACAATGGCAAACCTTAGAAATCTTGGTTATTTGGATTTCTCCTTCAACAATTTCACT
GGTTCTATCCCATATTTTCGACTGTCCAAGAAACTCACCTACTTAGACCTTTCACGTAATGG
TCTAACTGGTCTCTTGTCTAGAGCTCATTTTGAAGGACTCTCAGAGCTTGTCCACATTAATT
TAGGGAACAATTTACTCAGCGGGAGCCTTCCTGCATATATATTTGAGCTCCCCTCGTTGCAG
CAGCTTTTTCTTTACAGAAATCAATTTGTTGGCCAAGTCGACGAATTTCGCAATGCATCCTC
CTCTCCGTTGGATACAGTTGACTTGACAAACAACCACCTGAATGGATCGATTCCGAAGTCCA
TGTTTGAAATTGAAAGGCTTAAGGTGCTCTCACTTTCTTCCAACTTCTTTAGAGGGACAGTG
CCCCTTGACCTCATTGGGAGGCTGAGCAACCTTTCAAGACTGGAGCTTTCTTACAATAAGTT
GACTGTTGATGCAAGTAGCAGCAATTCAACCTCTTTCACATTTCCCCAGTTGAACATATTGA
AATTAGCGTCTTGTCGGCTGCAAAAGTTCCCGATCTCAAGAATCAGTCATGGATGATGCAC
TTAGACCTTTCAGACAACCAAATATTGGGGCAATACCAAATTGGATCTGGGGAATTGGTGG
TGGAGGTCTCACCCACCTGAATCTTTCATTCAATCAGCTGGAGTACGTGGAACAGCCTTACA
CTGCTTCCAGCAATCTTGTAGTCCTTGATTTGCATTCCAACCGTTTAAAAGGTGACTTACTA
ATACCACCTTGCACTGCCATCTATGTGAACTACTCTAGCAATAATTTAAACAATTCCATCCC
AACAGATATTGGAAAGTCTCTTGGTTTTGCCTCCTTTTTCTCGGTAGCAAACAATGGCATTA
CTGGAATAATTCCTGAATCCATATGCAACTGCAGCTACCTTCAAGTTCTTGATTTCTCTAAC
AATGCCTTGAGTGGAACAATACCACCATGTCTACTGGAATATAGTACAAAACTTGGAGTGCT
GAATCTTGGGAACAATAAACTCAATGGTGTTATACCAGATTCATTTCAATTGGTTGTGCTC
TACAAACATTAGACCTCAGTGCGAATAACTTACAAGGCAGGCTGCCAAAATCGATTGTGAAT
TGTAAGTTGTTGGAGGTCCTGAATGTTGGAAATAACAGACTTGTTGATCATTTCCCATGCAT
GTTGAGGAACTCAAACAGTCTGAGGGTCCTAGTCTTGCGCTCCAATAAATTCTATGGAAATC
TTATGTGTGATGTAACCAGAAATAGCTGGCAGAATCTCCAGATCATAGATATAGCTTCCAAC
AACTTCACTGGTGTGTTGAATGCAGAATTCTTTTCAAATTGGAGAGGAATGATGGTTGCAGA
TGATTACGTGGAGACAGGACGCAATCATATCCAGTATGAGTTCTTACAACTAAGT

Fig. 6B

```
AAATTGTACTATCAGGACACAGTGACATTAACCATCAAAGGCATGGAGCTGGAGCTTGTGAA
GATTCTCAGGGTCTTCACATCTATTGATTTCTCTTCCAATAGATTTCAAGGAGCGATACCAG
ATGCTATCGGGAATCTCAGCTCACTTTATGTTCTGAATCTGTCACACAATGCCCTTGAGGGA
CCAATCCCAAAATCGATTGGGAAGCTACAAATGCTTGAATCACTAGACCTGTCAACAAACCA
CCTGTCCGGGGAGATCCCATCAGAGCTTGCAAGTCTCACATTCTTAGCAGCTTTGAACTTAT
CGTTCAACAAATTGTTTGGCAAAATTCCATCAACTAATCAGTTTCAAACATTCTCAGCAGAT
TCCTTTGAAGGAAACAGTGGCCTATGCGGGCTCCCTCTCAACAACAGTTGTCAAAGCAATGG
CTCAGCCTCAGAGTCCCTGCCTCCACCAACTCCGCTACCAGACTCAGATGATGAATGGGAGT
TCATTTTTGCAGCAGTTGGATACATAGTAGGGGCAGCAAATACTATTTCAGTTGTGTGGTTT
TACAAGCCAGTGAAGAAATGGTTTGATAAGCATATGGAGAAATGCTTGCTTTGGTTTTCAAG
AAAGTGATTATTAAACCCATAAATAATGAGTTTATTCTTGGAGTGTTTTGTTTTAAATAAAC
AACAGGATAAGGAAAATCAAGTTAATAAGCTCGCAGAACATGATTGTTATTTCCTTTGATGA
ATGTATACAATTTTCAATATTGGTTCTTCAACCATAACCGCAGGCTAACTGTCAGTTGTTGG
AAGTCCTGAATTTTGGAAATGACATACATTTTTATAGTTTC
```

Fig. 7

Ve 1.2 AA from cDNA

A          MKMMAAT*LYFPMVLLIPSFQILSGYHIFLV*

B          MTSECCNWNGVTCNLFGHVIALELDDETISSGIE
NSSALFSLQYLESLNLADNMFNVGIP
VGIDNLTNLKYLNLSNAGFVGQIP
ITLSRLTRLVTLDLSTILPFFDQP
LKLENPNLSHFIENSTELRELYLDGVDLSSQRS
EWCQSLSLHLPNLTVLSRDCQISGPLD
ESLTKLHFLSFVQLDQNNLSSTVP
EYFANFSNLTTLTLGSCNLQGTFP
ERIFQVSVLESLDLSINKLLRGSIP
IFFRNGSLRRISLSYTNFSGSLP
ESISNHQNLSRLELSNCNFYGSIP
STMANLRNLGYLDFSFNNFTGSIP
YFRLSKKLTYLDLSRNGLTGLLS
RAHFEGLSELVHINLGNNLLSGSLP
AYIFELPSLQQLFLYRNQFVGQVD
EFRNASSSPLDTVDLTNNHLNGSIP
KSMFEIERLKVLSLSSNFFRGTVP
LDLIGRLSNLSRLELSYNKLTVDAS
SSNSTSFTFPQLNILKLASCRLQKFPD
LKNQSWMMHLDLSDNQILGAIP
NWIWGIGGGGLTHLNLSFNQLEYVEQ
PYTASSNLVVLDLHSNRLKGDLLIP
PCTAIYVNYSSNNLNNSIPTDIG
KSLGFASFFSVANNGITGIIP
ESICNCSYLQVLDFSNNALSGTIP
PCLLEYSTKLGVLNLGNNKLNGVIP
DSFSIGCALQTLDLSANNLQGRLP
KSIVNCKLLEVLNVGNNRLVDHFP
CMLRNSNSLRVLVLRSNKFYGNLM
CDVTRNSWQNLQIIDIASNNFTGVLN
AEFFSNWRGMMVADDYVETGRNHIQ
YEFLQLSKLYYQDTVTLTIKGMELELVKI
LRVFTSIDFSSNRFQGAIP
DAIGNLSSLYVLNLSHNALEGPIP
KSIGKLQMLESLDLSTNHLSGEIP
SELASLTFLAALNLSFNKLFGKIP
STNQFQTFSADSFEGNSGLCGLPLNNSCQSNGSA

E          SESLPPPTPLPDSDDEWE

C          FIFAAVGYIVGAANTISVVWF

D          YKPVKKWFDKHMEKCLLWFSRK

Fig. 9A

Sequence Alignment of Ve1.1 and Ve1.2 AA sequences from cDNA

```
VE1F    - MRFLHFLWI--FFIIPFLQILLGNEILLVSSQCLDDQKSLLLQLKGSFQY  -48
          |..  |.   .||  ||| |  | ||||||||||||||| ||| ||
VE2F    - MKMMATLYFPMVLLIPSFQILSGYHIFLVSSQCLDDQKSLLLQFKGSLQY  -50

VE1F    - DSTLSNKLARWNHNTSECCNWNGVTCDLSGHVIALELDDEKISSGIENAS  -98
          ||||| |||.|| |||||||||||| |||||||||||||| |||||||.|
VE2F    - DSTLSKKLAKWNDMTSECCNWNGVTCNLFGHVIALELDDETISSGIENSS  -100

VE1F    - ALFSLQYLERLNLAYNKFNVGIPVGNLTNLTYLNLSNAGFVGQIPMML   -148
          |||||||| |||| | |||||||||| ||||| |||||||||||||.|
VE2F    - ALFSLQYLESLNLADNMFNVGIPVGIDNLTNLKYLNLSNAGFVGQIPITL -150

VE1F    - SRLTRLVTLDLSTLFPDFAQPLKLENPNLSHFIENSTELRELYLDGVDLS -198
          |||||||||||.|| | |||||||||||||||||||||||||||||||
VE2F    - SRLTRLVTLDLSTILPFFDQPLKLENPNLSHFIENSTELRELYLDGVDLS -200

VE1F    - AQRTEWCQSLSSYLPNLTVLSLRTCRISGPIDESLSKLHFLSFIRLDQNN -248
          .||.|||||||  |||||||||| | ||||.||||.|||||||.  |||||
VE2F    - SQRSEWCQSLSLHLPNLTVLSLRDCQISGPLDESLTKLHFLSFVQLDQNN -250

VE1F    - LSTTVPEYFANFSNLTTLTLSSCNLQGTFPKRIFQVPVLEFLDLSTNKLL -298
          ||.|||||||||||||||||| ||||||||| ||||| ||| ||| ||||
VE2F    - LSSTVPEYFANFSNLTTLTLGSCNLQGTFPERIFQVSVLESLDLSINKLL -300

VE1F    - SGSIPIFPQIGSLRTISLSYTKFSGSLPDTISNLQNLSRLELSNCNFSEP -348
          ||||||   ||||  ||||||| ||||||  ||| ||||||||||||
VE2F    - RGSIPIFFRNGSLRRISLSYTNFSGSLPESISNHQNLSRLELSNCNFYGS -350

VE1F    - IPSTMANLTNLVYLDFSFNNFTGSLPYFQGAKKLIYLDLSRNGLTGLLSR -398
          ||||||||  || |||||||||||||. ||| ||| ||||||||||||||
VE2F    - IPSTMANLRNLGYLDFSFNNFTGSIPYFRLSKKLTYLDLSRNGLTGLLSR -400

VE1F    - AHFEGLSELVYINLGNNSLNGSLPAYIFELPSLKQLFLYSNQFVGQVDEF -448
          |||||||||| ||||||| |||||||||||||  ||||| |||||||||||
VE2F    - AHFEGLSELVHINLGNNLLSGSLPAYIFELPSLQQLFLYRNQFVGQVDEF -450

VE1F    - RNASSSPLDTVDLRNNHLNGSIPKSMFEVGRLKVLSLSSNFFRGTVPLDL -498
          ||||||||||||||  ||||||||||||. ||||||||||||||||||||
VE2F    - RNASSSPLDTVDLTNNHLNGSIPKSMFEIERLKVLSLSSNFFRGTVPLDL -500

VE1F    - IGRLSNLSRLELSYNNLTVDASSSNSTSFTFPQLNILKLASCRLQKFPDL -548
          ||||||||||||||| ||||||||||||||||||||||||||||||||||
VE2F    - IGRLSNLSRLELSYNKLTVDASSSNSTSFTFPQLNILKLASCRLQKFPDL -550
```

Fig. 9B

```
VE1F      - KNQSRMMHLDLSDNQILGAIPNWIWGIGGGGLAHLNLSFNQLEYVEQPYT -598
            |||| |||||||||||||||||||||||||||·|||||||||||||||||
VE2F      - KNQSWMMHLDLSDNQILGAIPNWIWGIGGGGLTHLNLSFNQLEYVEQPYT -600

VE1F      - VSSNLVVLDLHSNRLKGDLLIPPSTAIYVDYSSNNLNNSIPTDIGRSLGF -648
             |||||||||||||||||||||| ||||| |||||||||||||||·||||
VE2F      - ASSNLVVLDLHSNRLKGDLLIPPCTAIYVNYSSNNLNNSIPTDIGKSLGF -650

VE1F      - ASFFSVANNSITGIIPESICNVSYLQVLDFSNNALSGTIPPCLLEYSPKL -698
            ||||||||| ||||||||||| ||||||||||||||||||||||||| ||
VE2F      - ASFFSVANNGITGIIPESICNCSYLQVLDFSNNALSGTIPPCLLEYSTKL -700

VE1F      - GVLNLGNNRLHGVIPDSFPIGCALITLDLSRNIFEGKLPKSLVNCTLLEV -748
            ||||||||·| ||||||| ||||| ||||| |   |·||||·||| ||||
VE2F      - GVLNLGNNKLNGVIPDSFSIGCALQTLDLSANNLQGRLPKSIVNCKLLEV -750

VE1F      - LNVGNNSLVDRFPCMLRNSTSLKVLVLRSNKFNGNLTCNITKHSWKNLQI -798
            |||||| ||| |||||||| ||·||||||||| ||| | ·|· || ||||
VE2F      - LNVGNNRLVDHFPCMLRNSNSLRVLVLRSNKFYGNLMCDVTRNSWQNLQI -800

VE1F      - IDIASNNFTGMLNAECFTNWRGMMVAKDYVETGRNHIQYEFLQLSNLYYQ -848
            ||||||||||·|||| |·|||||||| |||||||||||||||||| ||||
VE2F      - IDIASNNFTGVLNAEFFSNWRGMMVADDYVETGRNHIQYEFLQLSKLYYQ -850

VE1F      - DTVTLIIKGMELELVKILRVFTSIDFSSNRFQGKIPDTVGDLSSLYVLNL -898
            ||||| ||||||||||||||||||||||||||| |||··| |||||||||
VE2F      - DTVTLTIKGMELELVKILRVFTSIDFSSNRFQGAIPDAIGNLSSLYVLNL -900

VE1F      - SHNALEGPIPKSIGKLQMLESLDLSRNHLSGEIPSELSSLTFLAVLNLSF -948
            ||||||||||||||||||||||||| |||||||||||·|||||| |||||
VE2F      - SHNALEGPIPKSIGKLQMLESLDLSTNHLSGEIPSELASLTFLAALNLSF -950

VE1F      - NNLFGKIPQSNQFETFSAESFEGNRGLCGLPLNVICKSD--TSELKPAPS -996
            | |||||| ·||| ||||·||||| ||||||||  | |   ·||  | |·
VE2F      - NKLFGKIPSTNQFQTFSADSFEGNSGLCGLPLNNSCQSNGSASESLPPPT -1000

VE1F      - SQDDSYD-WQFIFTGVGYGVGAAISIAPLLFYKQGNKYFDKHLERMLKLM -1045
               || | | |||· ||| |||| ·|· · |||   |·||||·|· |
VE2F      - PLPDSDDEWEFIFAAVGYIVGAANTISVVWFYKPVKKWFDKHMEKCL--- -1047

VE1F      - FPRYWFSYTRFDPGKVVAVEHYEDETPDDTEDDDEGGKEASLGRYCVFCS -1095
               |||
VE2F      - ---LWFS------------------------------------------- -1051

VE1F      - KLDFQKNEAMHDPKCTCHMSSSPNSFPPTPSFFSPLLVIYHKKF -1139
                                                      ·|
VE2F      - ------------------------------------------RK  -1053
```

Fig. 10

Vc Partial Genomic DNA Sequence

CATGATTACGCCAAGCTATTTAGGGACATATAGAATACTCAAGCTATGCATCCAACGCGTGG
GGGAGCTCTCCCATATGGTCGACCTGCAGGCGNCCGCGAATTCACTAGTGATTAATTCACTC
AACGGGAGCCTTCCTGCATGTATCTTTGAGCTTCCCTCCTTGCAGACGCTTTTACTTAACAG
CAATCAATTTGTTGGCCAAGTCAACCATTTTCACAATGCATCCTCCTTTCTCGATGAAATTG
ATTTGAGCAACAACCAACTGAATGGTTCAATTCCCAAGTCCATGTTTGACGTTGGGAGGCTT
AAGGTTCTCTCACTTTCTTCCAATTTCTTTAGCGGAACAGTACCCCTTGACCTCATTGGGAA
GCTGAGCAATCTTTCACGACTGGAGCTTTCTTACAATAACTTGACTGTTGATGCAAGTAGCA
GTAATTCAGACTCTTTCACATTTCCCCAGTTGAACATATTGAAACTAGCTTCGTGTCGGCTG
CAAAAGTTTCCTGATCTTAAAAATCAGTCAAGGATGATCCAATTAGACCTTTCTGACAACAA
AATACTGGGGGCAATACCAAATTGGATTTGGCGAATAGGTAACGGAGCTCTGAGTCACCTGA
ATCTTTCTTTCAATCAGTTGGAGTACGTGGAACAGCCTTACAATGTTTCCAGATATCTTGTC
GTCCTTGACTTGCATTCCAATAAGCTAAAGGGTGACCTACCAATTCCACCTTCCTTTGCTGC
ATATTTGGACTACTCGAGCAATAATTTCAGCAATTCCATCCCACTAGATATTGGCAATTATC
TTGGTTTTGCCTCCTTTTTCTCGGTAGCAAACAATGGCATTACTGGAAGAATTCCCGAATCC
ATATGCAATGTCAGCTACCTTCAAGTTCTTGATTTCTCTAACAATGCCTTGAAATCGAATTC
CCGCGGCCGCCATGGCGGCCGGGAGCATGCGACGTCGGGCCCAATTCGCCCT

Fig. 11A

Sequence Alignment Ve1.2 and Vc

```
VC1    - MITPS--------------YLGTYRILKLCIQRVGE-------------- -22
         |    .             |  | |   .  | . .
VE2F   - MKMMATLYFPMVLLIPSFQILSGYHIFLVSSQCLDDQKSLLLQFKGSLQY -50

VC1    - -------------------------------------------------- -22

VE2F   - DSTLSKKLAKWNDMTSECCNWNGVTCNLFGHVIALELDDETISSGIENSS -100

VC1    - -------------------LSHMVDLQAXAN------------------- -34
                            .  |  .   .|
VE2F   - ALFSLQYLESLNLADNMFNVGIPVGIDNLTNLKYLNLSNAGFVGQIPITL -150

VC1    - -------------------------------------------------- -34

VE2F   - SRLTRLVTLDLSTILPFFDQPLKLENPNLSHFIENSTELRELYLDGVDLS -200

VC1    - -------------------------------------------------- -34

VE2F   - SQRSEWCQSLSLHLPNLTVLSLRDCQISGPLDESLTKLHFLSFVQLDQNN -250

VC1    - -------------------------------------------------- -34

VE2F   - LSSTVPEYFANFSNLTTLTLGSCNLQGTFPERIFQVSVLESLDLSINKLL -300

VC1    - -------------------------------------------------- -34

VE2F   - RGSIPIFFRNGSLRRISLSYTNFSGSLPESISNHQNLSRLELSNCNFYGS -350

VC1    - -------------------------------------------------- -34

VE2F   - IPSTMANLRNLGYLDFSFNNFTGSIPYFRLSKKLTYLDLSRNGLTGLLSR -400

VC1    - ------------SLVINSLNGSLPACIFELPSLQTLLLNSNQFVGQVNHF -72
                     |  | | ||||| |||||||| | |  ||||||| |
VE2F   - AHFEGLSELVHINLGNNLLSGSLPAYIFELPSLQQLFLYRNQFVGQVDEF -450

VC1    - HNASSF-LDEIDLSNNQLNGSIPKSMFDVGRLKVLSLSSNFFSGTVPLDL -121
          ||||  || .||.|| ||||||||||.. ||||||||||| |||||||
VE2F   - RNASSSPLDTVDLTNNHLNGSIPKSMFEIERLKVLSLSSNFFRGTVPLDL -500

VC1    - IGKLSNLSRLELSYNNLTVDASSSNSDSFTFPQLNILKLASCRLQKFPDL -171
         ||.||||||||||| ||||||||| ||||||||||||||||||||||
VE2F   - IGRLSNLSRLELSYNKLTVDASSSNSTSFTFPQLNILKLASCRLQKFPDL -550

VC1    - KNQSRMIQLDLSDNKILGAIPNWIWRIGNGALSHLNLSFNQLEYVEQPYN -221
         |||| |. |||||| |||||||||| || | |.||||||||||||||||
VE2F   - KNQSWMMHLDLSDNQILGAIPNWIWGIGGGGLTHLNLSFNQLEYVEQPYT -600
```

Fig. 11B

```
VC1    - VSRYLVVLDLHSNKLKGDLPIPPSFAAYLDYSSNNFSNSIPLDIGNYLGF -271
          |  |||||||||.||||| |||  | |. |||||  |||| |||  |||
VE2F   - ASSNLVVLDLHSNRLKGDLLIPPCTAIYVNYSSNNLNNSIPTDIGKSLGF -650
VC1    - ASFFSVANNGITGRIPESICNVSYLQVLDFSNNAL--------------- -306
         ||||||||||||| ||||||| |||||||||||||
VE2F   - ASFFSVANNGITGIIPESICNCSYLQVLDFSNNALSGTIPPCLLEYSTKL -700
VC1    - -------------------------------------------------- -306
VE2F   - GVLNLGNNKLNGVIPDSFSIGCALQTLDLSANNLQGRLPKSIVNCKLLEV -750
VC1    - -----------------KSNS----------------------------- -310
                           |||
VE2F   - LNVGNNRLVDHFPCMLRNSNSLRVLVLRSNKFYGNLMCDVTRNSWQNLQI -800
VC1    - --------------------RGRHGGREHATSG----------------- -323
                             ||      .   .|
VE2F   - IDIASNNFTGVLNAEFFSNWRGMMVADDYVETGRNHIQYEFLQLSKLYYQ -850
VC1    - -------------------------------------------------- -323
VE2F   - DTVTLTIKGMELELVKILRVFTSIDFSSNRFQGAIPDAIGNLSSLYVLNL -900
VC1    - -------PI----------------------------------------- -325
                ||
VE2F   - SHNALEGPIPKSIGKLQMLESLDLSTNHLSGEIPSELASLTFLAALNLSF -950
VC1    - -------------------------------------------------- -325
VE2F   - NKLFGKIPSTNQFQTFSADSFEGNSGLCGLPLNNSCQSNGSASESLPPPT -1000
VC1    - -------------------------------------------------- -325
VE2F   - PLPDSDDEWEFIFAAVGYIVGAANTISVVWFYKPVKKWFDKHMEKCLLWF -1050
VC1    - -RP -327
          |
VE2F   - SRK -1053
```

TOMATO NUCLEIC ACID SEQUENCES THAT CONFER RESISTANCE TO VERTICILLIUM AND PLANTS TRANSFORMED THEREWITH

CROSS-REFERENCE TO RELATED APPLICATIONS

This application claims the benefit of United States Provisional Patent Application Serial No. 60/124,129 filed Mar. 12, 1999 and United States Provisional Patent Application Serial No. 60/130,586 filed Apr. 22, 1999. To the extent that they are consistent herewith, the aforementioned applications are incorporated herein by reference.

FIELD OF THE INVENTION

The invention pertains to the field of molecular biology. In particular, the invention pertains to genes which confer resistance on plants to Verticillium species.

BACKGROUND OF THE INVENTION

Verticillium wilt is a common vascular disease that causes severe yield and quality losses in many crops. The disease is caused by fungi of the genus Verticillium, most commonly *Verticillium albo-atrum* Reingke & Berthier or *Verticillium dahliae* Kleb. The relationship between *V. albo-atrum* and *V. dahliae* has been the subject of debate (see, generally, Domsch et al., 1980). They have previously been considered representatives of a single variable species, but they have more recently been viewed as distinct species.

*V. albo-atrum* was first identified as a causal agent of Verticillium wilt in potato, but is now known also to cause wilt in hop, tomato, alfalfa, strawberry, sainfoin, runner bean, broad bean, pea, clover and cucumber. Vascular infection of these hosts by *V. albo-atrum* leads to wilt, with or without obvious flaccidity, and, commonly, browning of the infected xylem stems.

*V. dahlia* is far more common than *V. albo-atrum*, but causes disease symptoms that are less severe than those caused by *V. albo-atrum* infection. Further, in the above-mentioned hosts, *V. dahlia* is usually less virulent than *V. albo-atrum*. *V. dahlia* is known to infect canola, cotton, dahlia, mint species, vine, tomato, potato, eggplant, olive, pistachio, stone fruits, Brussels sprouts, groundnut, horse radish, tobacco, red pepper, strawberry, and other plant species. Symptoms of *V. dahlia* infection usually include flaccidity or chlorosis of leaves, followed by permanent wilting.

In a recent survey in North America, Verticillium wilt was ranked as the most important disease of both seed and commercial potato crops, and the second greatest constraint on tuber yield. Pathogen-mediated reductions in net photosynthesis, transpiration, and increased leaf temperature cause premature foliage senescence and yield loss. Disease symptoms in potato include wilting and leaf chlorosis and necrosis, while the tubers of infected plants develop necrosis in the vascular tissue that reduces tuber quality, in particular for the manufacture of french fries and chips. Abiotic factors such as moisture stress and high temperatures accelerate development of visual disease symptoms. Studies have demonstrated a synergistic interaction between root-lesion nematodes (*Pratylenchus penetrans*) and Verticillium wilt, further complicating disease control.

Management strategies for the control of Verticillium wilt include soil fumigation, crop rotation, and development of resistant cultivars. Of these strategies, only disease resistance is effective. While several recent potato cultivar releases have some resistance to the pathogen, the major potato varieties grown in North America are susceptible. The genetic mechanisms of resistance towards fungi of the taxon Verticillium spp. vary from polygenic in strawberry and alfalfa, to a dominant single gene in cotton, sunflower, and tomato. Conclusions from studies with tetraploid *Solanum tuberosum* subsp. tuberosum L. suggest that inheritance is polygenic and complex. Screening for resistance in the non-cultivated diploid tuber-bearing wild Solanum species has identified resistance but not immunity, and a recent study concluded that resistance is polygenic and genetically complex. Thus, incorporation of resistance into new potato cultivars by classical breeding techniques is difficult and inefficient. It would therefore be desirable to develop alternative approaches to obtaining plants that are resistant to Verticillium wilt.

Plants have natural defenses which prevent infection of the plant by viruses, bacteria, fungi, nematodes and insects. As plants do not have a circulatory system, each plant cell must have a preformed or inducible defensive capacity. Recently, disease resistance genes, which confer resistance to specific pathogens, have been identified in various plants. It is believed that the mechanism of resistance may differ depending on the mode of pathogen attack.

Necrotrophy, biotrophy and hemibiotrophy are the three principal modes of pathogen attack on plants (see, generally, Hammond-Kosack et al., 1997). Necrotrophs first kill host cells, then metabolize the cell contents. Necrotrophs often have a broad host range, and cause host cell death with toxins or enzymes targeted to certain substrates. Plant resistance to necrotrophs may therefore be achieved through loss or alteration of the target of the toxin in the plant, or through detoxification of the toxin produced by the plant. An example of a plant disease resistance gene of the latter type Hm1, isolated from maize, and which confers resistance to the leaf spot fungus *Cochliobolus carbonum*. Hm1 encodes a reductase enzyme which is thought to inactivate the *C. carbonum* toxin.

Flor (1949) developed the classic "gene-for-gene" model for plant pathogen resistance. Flor proposed that for incompatibility (i.e. resistance) to occur, complementary pairs of dominant genes are required, one in the host and the other in the pathogen. Loss or alteration of either the plant resistance ("R") gene or the pathogen avirulence ("Avr") gene results in compatibility (i.e. disease). It is thought that R genes encode proteins that can recognize Avr-gene-dependent ligands. The simplest possibility is that the Avr-gene-dependent ligand binds directly to the R gene product. Following binding, the R gene product is believed to activate downstream signaling cascades to induce defense responses, such as the hypersensitive response, which causes localized plant cell death at the point of pathogen attack, thereby depriving the pathogen of living host cells. Downstream signaling components may include kinase and phosphatase cascades, transcription factors, and reactive oxygen species (see, generally, Hammond-Kosack et al., 1997).

Hammond-Kosack et al. (1997) summarize the five classes of known R genes, classified according to predicted features of the R gene product.

The first class is composed of R genes that encode detoxifying enzymes. An example is Hm1 from maize, discussed above, which confers resistance to *Cochliobolus carbonum* (Johal et al., 1992).

R genes of the second class encode intracellular serine/threonine-specific protein kinases. An example is Pto, isolated from tomato, and which confers resistance to *Pseudomonas syringe* pv. tomato (Martin et al., 1993).

The third class of R genes is divided into two subclasses. The first encode intracellular proteins with an amino terminal leucine zipper domain, a nucleotide binding site ("NBS") domain, and a leucine rich repeat ("LRR") domain. Examples include RPS2 of Arabidopsis, which confers resistance to *Pseudomonas syringe* pv. tomato (Bent et al., 1994; Mindrinos et al., 1994), and I2, from tomato, which confers resistance to *Fusarium oxysporum* (Ori et al., 1997). R genes of the second subclass encode intracellular proteins with an amino terminal domain having homology with Drosophila Toll protein, and NBS and LRR domains. Examples include R gene N of the tobacco plant, which confers resistance to tobacco mosaic virus (Whitman et al., 1994), and L6 of flax, which confers resistance to *Melampsora lini* (Lawrence et al., 1995).

R genes of the fourth class encode proteins having an extracellular LRR, a single membrane spanning region, and a short cytoplasmic carboxyl terminus. An example is Cf9 of tomato, which confers resistance to *Cladosporium fulvum* (Jones et al., 1994).

The fifth class encompasses R genes encoding proteins having an extracellular LRR, a single membrane spanning region, and a cytoplasmic kinase domain. An example is R gene Xa21 of rice, which confers resistance to *Xanthomonas oryzae* pv. oryzae (Song et al., 1995).

Certain isolated R genes have been introduced into susceptible plants, resulting in transgenic, disease-resistant plants. For instance, U.S. Pat. No. 5,859,339 teaches transformation of susceptible rice plants with the rice Xa21R gene, resulting in transgenic rice plants that are resistant to Xanthomonas infection. U.S. Pat. No. 5,920,000 teaches transformation of susceptible tomato plants with the tomato Cf9 R gene, resulting in transgenic tomato plants that are resistant to infection by *Cladosporium fulvum*.

However, the prior art R genes and methods do not confer on plants resistance to Verticillium species. Hence, there is a need for isolated Verticillium wilt resistance genes, and for methods for conferring resistance on plant species to infection by Verticillium species.

SUMMARY OF THE INVENTION

The invention provides isolated polynucleotides of at least about 50 nucleotides, preferably at least about 100 nucleotides, more preferably at least about 200 nucleotides, more preferably at least about 500 nucleotides, more preferably at least about 1000 nucleotides, and even more preferably at least about 2000 nucleotides, which encode polypeptides comprising amino acid sequences having at least 40% homology to the amino acid sequence depicted in SEQ ID NO: 2, 4, 6, 8, or 14 and which polynucleotides, when present in a plant, confer on the plant resistance to Verticillium species. These polynucleotides are denoted herein as "Ve" polynucleotides. The isolated Ve polynucleotides preferably encode polypeptides comprising amino acid sequences having at least 50% homology, more preferably at least 60% homology, more preferably at least 70% homology, more preferably at least 80% homology, more preferably at least 85% homology, more preferably at least 90% homology, and even more preferably at least 95% homology with the amino acid sequence depicted in SEQ ID NO: 2, 4, 6, 8, or 14. Preferably, the polynucleotides of the invention are isolated from tomato (*Lycopersicon esculentum*), though they may be obtained from other plant species such as potato, hop, alfalfa, strawberry, sainfoin, runner bean, broad bean, pea, clover, cucumber, canola, cotton, dahlia, mint species, vine, eggplant, olive, pistachio, stone fruit, Brussels sprouts, groundnut, horse radish, tobacco, and red pepper.

In an exemplified case, the Ve polynucleotide is isolated from *L. esculentum*, and has the nucleotide sequence depicted in SEQ ID NO: 1 from nucleotide 1 to nucleotide 3417, SEQ ID NO: 3 from nucleotide 57 to nucleotide 3473, SEQ ID NO: 5 from nucleotide 1 to nucleotide 3159, or in SEQ ID NO: 7 from nucleotide 1 to nucleotide 3159. The sequences depicted in SEQ ID NO: 3 from nucleotide 57 to nucleotide 3473, and in SEQ ID NO: 7 from nucleotide 1 to nucleotide 3159 are complementary DNA ("cDNA") sequences, and are denoted herein as, respectively, the *L. esculentum* verticillium wilt resistance genes Ve1.1 and Ve1.2. The sequences depicted in SEQ ID NO: 1 from nucleotide 1 to nucleotide 3417, and SEQ ID NO: 5 from nucleotide 1 to nucleotide 3159 are genomic DNA sequences of Ve1.1 and Ve1.2. Ve1.1 and Ve1.2 are two open reading frames ("ORFs") occurring at the same locus, denoted herein as Ve1.

In another exemplified case, the Ve polynucleotide is isolated from *Solanum chacoense*, has the partial nucleotide sequence depicted in SEQ ID NO: 13, and is denoted herein as Vc.

The invention extends to purified and isolated polynucleotides of at least 50 nucleotides, preferably at least 100 nucleotides, more preferably at least 200 nucleotides, even more preferably at least 500 nucleotides, and most preferably at least 1000 nucleotides, comprising Verticillium wilt resistance gene promoters. An exemplified promoter sequence is depicted in SEQ ID NO: 10.

The invention also provides nucleic acid constructs, vectors, and transformed cells containing at least one of the aforementioned Ve polynucleotides.

The invention further extends to transgenic plants, cells, seeds and embryos transformed with at least one Ve polynucleotide of the invention, and to methods for conferring on susceptible plants resistance to Verticillium species, by transforming plant cells with at least one Ve polynucleotide of the invention and regenerating mature plants. It may be desirable to transform the plant with more than one Ve polynucleotide. For instance, an additive effect may result if the plant is transformed with both Ve1.1 and Ve1.2.

The invention further extends to methods for obtaining a polynucleotide which, when present in a plant, confers on the plant resistance to Verticillium species. Broadly stated, such methods comprise the steps of: isolating polynucleotides from a plant having resistance to Verticillium species; performing nucleic acid hybridization between said polynucleotides and a probe comprising a nucleotide sequence derived from any of the sequences depicted in SEQ ID NO:1–8, 10, 13 or 14; and, testing polynucleotides that hybridize with said probe for ability to confer on a plant resistance to Verticillium species.

Vertical lines indicate location of the AUG initiation codons. Expressed sequences were cloned into λ and the arrowhead depicts the direction of transcription for the cDNA identified using the genomic clone pG1Ve. Potato plants transformed with the genomic subclones (pG1Ve, pG2Ve, pG3Ve) and cDNA (pC1.1Ve, pC1.2Ve) exhibited in vivo complementation and resistance (R) when challenged with *Verticillium albo-atrum*.

FIGS. 2A and 2B depict the Ve1.1 genomic DNA sequence (SEQ ID NO: 1, from nucleotide 1 to nucleotide 3417). The deduced Ve1.1 amino acid sequence encoded by the Ve1.1 genomic DNA sequence is depicted in SEQ ID NO: 2.

FIGS. 3A and 3B depict the Ve1.1 cDNA sequence (SEQ ID NO: 3 from nucleotide 57 to nucleotide 3473).

FIGS. 4A and 4B depict the primary structure of the encoded Ve1.1 protein (SEQ ID NO: 4) deduced from the Ve1.1 cDNA sequence (SEQ ID NO: 3 from nucleotide 57 to nucleotide 3473). Domains A through F are identified, as described in Example 1 herein. In the potential membrane associated domains A and C, hydrophobic amino acids are underlined. Within the leucine-rich repeat ("LRR") domain B, conserved amino acids L and G, and potential N-glycosylation sites, are underlined. In domain D, the neutral and basic amino acids are underlined. In domain E, acidic amino acids of the putative PEST sequence are underlined.

FIGS. 5A and 5B depict the Ve1.2 genomic DNA sequence (SEQ ID NO: 5 from nucleotide 1 to nucleotide 3159). The deduced Ve1.2 amino acid sequence encoded by the Ve1.2 genomic DNA sequence is depicted in SEQ ID NO: 6.

FIGS. 6A and 6B depict the Ve1.2 cDNA sequence (SEQ ID NO: 7 from nucleotide 1 to nucleotide 3159).

FIG. 7 depicts the primary structure of the encoded Ve1.2 protein (SEQ ID NO: 8) deduced from the Ve1.2 cDNA sequence (SEQ ID NO: 7 from nucleotide 1 to nucleotide 3159). Domains A through E are identified, as described in Example 1 herein. In the potential membrane associated domains A and C, hydrophobic amino acids are underlined. The italicized amino acids in domain A represent the putative leucine zipper region. Within the LRR domain B, conserved amino acids L and G, and potential N-glycosylation sites are underlined. In domain D, the neutral and basic amino acids are underlined. In domain E, acidic amino acids of the putative PEST sequence are underlined.

Figure 8:
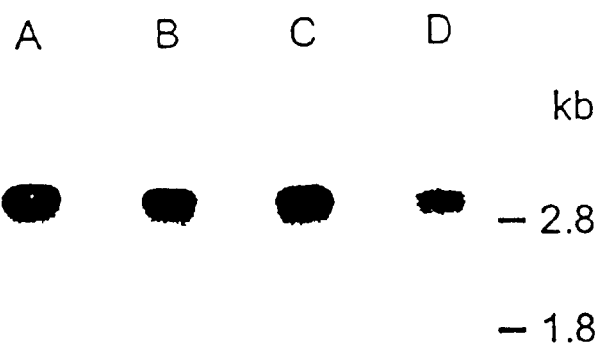

FIG. 8 is a Northern analysis of Ve1.1 cDNA expression. Hybridization of pC1Ve was determined using 5 μg of poly (A⁺) RNA extracted from uninoculated (A) Ailsa Craig and (B) Craigella or (C) Ailsa Craig and (D) Craigella inoculated with race 1 of *V. dahliae* three days prior to RNA isolation. Transcript of Ve1 is constitutively expressed in susceptible and resistant genotypes.

FIGS. 9A and 9B are a sequence alignment of the Ve1.1 and Ve1.2 protein sequences. The sequences have about 84% identity. Aligned identical residues are identified by the "|" character. Aligned similar residues are identified by the "." character. Similar amino acids are deemed to be: A, S, and T; D and E; N and Q; R and K; I, L, M and V; F, Y and W.

FIG. 10 depicts a partial genomic DNA sequence of the Vc Verticillium wilt resistance gene of *Solanum chacoense* (SEQ ID NO: 13). The deduced partial Vc amino acid sequence encoded by the Vc genomic DNA sequence is depicted in SEQ ID NO: 14.

FIGS. 11A and 11B are a sequence alignment of the Ve1.2 protein sequence and the Vc partial protein sequence. The sequences have about 72% identity. Aligned identical residues are identified by the "|" character. Aligned similar residues are identified by the "." character. Similar amino acids are deemed to be: A, S, and T; D and E; N and Q; R and K; I, L, M and V; F, Y and W.

DETAILED DESCRIPTION OF THE INVENTION

In order to provide a clear and consistent understanding of the specification and claims, including the scope to be given to such terms, the following definitions are provided.

A polynucleotide or polypeptide having the "biological activity" of, respectively, an exemplified Ve polynucleotide or Ve polypeptide of the invention, is a sequence that is functional in a plant to conf aligned for maximum correspondence as described herein. Sequence comparisons between two or more polynucleotides or polypeptides are generally performed by comparing portions of the two sequences over a comparison window to identify and compare local regions of sequence similarity. The comparison window is generally from about 20 to about 200 contiguous nucleotides or contiguous amino acid residues. The "percentage of sequence identity" or "percentage of sequence homology" for polynucleotides and polypeptides may be determined by comparing two optimally aligned sequences over a comparison window, wherein the portion of the polynucleotide or polypeptide sequence in the comparison window may include additions or deletions (i.e., gaps) as compared to the reference sequence (which does not comprise additions or deletions) for optimal alignment of the two sequences. The percentage is calculated by: (a) determining the number of positions at which the identical nucleic acid base or amino acid residue occurs in both sequences to yield the number of matched positions; (b) dividing the number of matched positions by the total number of positions in the window of comparison; and, (c) multiplying the result by 100 to yield the percentage of sequence identity.

Optimal alignment of sequences for comparison may be conducted by computerized implementations of known algorithms, or by inspection. A list providing sources of both commercial available and free software is found in Ausubel et al. (1999, and in previous editions). Readily available sequence comparison and multiple sequence alignment algorithms are, respectively, the Basic Local Alignment Search Tool (BLAST) (Altschul et al., 1990; Altschul et al., 1997) and ClustalW programs. Other suitable programs include GAP, BESTFIT, FASTA, and TFASTA in the Wisconsin Genetics Software Package (Genetics Group (GCG), 575 Science Dr., Madison, Wis.). For greater certainty, as used herein and in the claims, "percentage of sequence identity" or "percentage of sequence homology" of amino acid sequences is determined based on optimal sequence alignments determined in accordance with the default values of the BLASTX program.

As discussed in greater detail hereinafter, homology between nucleotide sequences can also be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated", but the same polynucleotide or polypeptide separated from the coexisting materials of its natural state is "isolated", as the term is employed herein.

Two DNA sequences are "operably linked" if the nature of the linkage does not interfere with the ability of the sequences to effect their normal functions relative to each other. For instance, a promoter region would be operably linked to a coding sequence if the promoter were capable of effecting transcription of that coding sequence.

A "polynucleotide" is a linear sequence of deoxyribonucleotides (in DNA) or ribonucleotides (in RNA) in which the 3' carbon of the pentose sugar of one nucleotide is linked to the 5' carbon of the pentose sugar of the adjacent nucleotide via a phosphate group.

A "polynucleotide construct" is a nucleic acid molecule which is isolated from a naturally occurring gene or which has been modified to contain segments of nucleic acid which are combined and juxtaposed in a manner which would not otherwise exist in nature.

A "polypeptide" is a linear polymer of amino acids that are linked by peptide bonds.

A "promoter" is a cis-acting DNA sequence, generally 80–120 base pairs long and located upstream of the initiation site of a gene, to which RNA polymerase may bind and initiate correct transcription.

A "recombinant" polynucleotide, for instance a recombinant DNA molecule, is a novel nucleic acid sequence formed in vitro through the ligation of two or more nonhomologous DNA molecules (for example a recombinant plasmid containing one or more inserts of foreign DNA cloned into its cloning site or its polylinker).

A plant that is "resistant" to Verticillium species, is a plant that, after inoculation with a strain of Verticillium, such as *Verticillium albo-atrum*, exhibits reduced or delayed symptoms of Verticillium wilt, such as wilting, chlorosis, necrosis, and death, relative to a control plant inoculated with the pathogen under the same conditions. A control plant may be, for example, a plant of the same species that has been transformed with a vector that does not have a disease resistance gene inserted therein. Accordingly, a gene that confers "resistance" to Verticillium species is a gene that, when present in a plant, makes the plant resistant to Verticillium species.

A "Solanaceous plant" is a plant of the botanical family Solanaceae. Also known as the nightshade family, this group includes several widely cultivated plants such as potato, tomato, tobacco, pepper, eggplant, and petunia.

"Transformation" means the directed modification of the genome of a cell by the external application of purified recombinant DNA from another cell of different genotype, leading to its uptake and integration into the subject cell's genome. In bacteria, the recombinant DNA is not integrated into the bacterial chromosome, but instead replicates autonomously as a plasmid.

A "transgenic" organism, such as a transgenic plant, is an organism into which foreign DNA has been introduced. A "transgenic plant" encompasses all descendants, hybrids, and crosses thereof, whether reproduced sexually or asexually, and which continue to harbour the foreign DNA.

"Upstream" means on the 5' side of any site in DNA or RNA.

A "vector" is a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g. promoter) for the expression of the inserted DNA. Common vectors include plasmid vectors and phage vectors.

A "Ve polynucleotide" is a polynucleotide which, when present in a plant, including a transgenic plant, confers on the plant resistance to Verticillium species.

A "Ve polypeptide" is a polypeptide encoded by a Ve polynucleotide, and which is active to confer resistance to Verticillium species on a plant.

"Verticillium wilt" is a plant disease caused by a fungus of the genus Verticillium, and which is characterized by wilting, chlorosis, necrosis, reduced yield, and, possibly, eventual death of the infected plant.

The term "Verticillium species" encompasses all members of the genus Verticillium, as described by Domsch et al. (1980). Verticillium species include, without limitation, *V. albo-atrum, V dahlia, V. catenulatum, V chlamydosporium, V. lecanii, V nigrescens, V. nubilum, V. psalliotae,* and *V. tricorpus.*

The invention provides Ve polynucleotides which, when present in a plant, confer on the plant resistance to Verticillium species. In an exemplified case, the Ve polynucleotide is isolated from *Lycopersicon esculentum*, and has the cDNA sequence depicted in SEQ ID NO: 3 from nucleotide 57 to nucleotide 3473 (Ve1.1), or in SEQ ID NO: 7 from nucleotide 1 to nucleotide 3159 (Ve1.2) and encodes, respectively, the Ve polypeptide having the amino acid sequence depicted in SEQ ID NOS: 4 or 8. Although it appears that Ve1.1 and Ve1.2 do not contain introns, the respective genomic DNA sequences depicted in SEQ ID NO: 1 from nucleotide 1 to nucleotide 3417 and SEQ ID NO: 5 from nucleotide 1 to nucleotide 3159, and consequently the deduced amino acid sequences depicted in SEQ ID NOS: 2 and 6, differ slightly from the cDNA sequences. Without being limited by the same, it is thought that this difference may be due to natural variation among *L. esculentum* strains. Although both Ve1.1 and Ve1.2 are functional to confer on plants resistance to Verticillium species, as shown in FIG. 9, the Ve1.1 and Ve1.2 DNA sequences differ substantially, and have only about 84% sequence homology.

As described in detail in Example 1 herein, Ve1.1 and Ve1.2 were isolated from a strain of *L. esculentum* (tomato) that is resistant to *Verticillium dahliae.* Potato plants regenerated from plant cells transformed with a vector containing Ve1.1 or Ve1.2, and then inoculated with *V. albo-atrum*, exhibited reduced and/or delayed symptoms of verticillium wilt (e.g. wilting, chlorosis, necrosis) relative to inoculated control plants transformed only with vector DNA. As shown in Table 1, untransformed potato plants (Désirée), or potato plants transformed only with vector DNA (pBI121 and pBIN19) exhibited no resistance to *V. albo-atrum.* In contrast, plants transformed with the Ve1.1 genomic and cDNA sequences (pG3Ve and pC1.1Ve, respectively) and Ve1.2 genomic and cDNA sequences (pG2Ve and pC1.2Ve, respectively) exhibited substantial resistance to *V. albo-atrum.* Hence, not only do the exemplified Ve polynucleotides confer resistance on various plant species (tomato, potato), they confer resistance to various Verticillium species (*V. dahliae* and *V. albo-atrum*).

In another exemplified case, the Ve polynucleotide is isolated from *Solanum chacoense*, a wild potato variety, and has a partial nucleotide sequence as depicted in SEQ ID NO: 13.

It will be appreciated by those of skill in the art that, due to the degeneracy of the genetic code, numerous functionally equivalent nucleotide sequences encode the same amino acid sequence. Therefore, all Ve polynucleotides that encode the Ve polypeptides depicted in SEQ ID NOS: 2, 4, 6, and 8, and the partial Ve polypeptide sequence depicted in SEQ ID NO: 14, are included in the invention.

Further, strains of *L. esculentum* or *S. chacoense* may contain naturally occurring allelic variants of the exemplified Ve polynucleotides. All such allelic variants of the exemplified Ve polynucleotides Ve1.1 and Ve1.2, and the exemplified partial Vc sequence, and the encoded Ve polypeptides are included within the scope of the invention.

The invention also extends to truncated Ve polynucleotides and Ve polypeptides that, despite truncation, retain the ability to confer on plants resistance to Verticillium species.

For instance, as discussed in Example 1 herein, a fragment of Ve1.1, 1332 nucleotides in length (SEQ ID NO: 1 from nucleotide 1 to nucleotide 1332), and a fragment of Ve1.2, 1146 nucleotides in length (SEQ ID NO: 5 from nucleotide 1 to nucleotide 1146), were both were functional to confer on a plant resistance to Verticillium species.

Using a variety of techniques that are well known in the art (generally as described in Sambrook et al., 1989; Ausubel et al., 1990; Ausubel et al., 1999), the exemplified Ve polynucleotides can be used to isolate additional Ve polynucleotides. Ve polynucleotides of the invention can be isolated from, without limitation, tomato, potato, hop, alfalfa, strawberry, sainfoin, runner bean, broad bean, pea, clover, cucumber, canola, cotton, dahlia, mint species, vine, eggplant, olive, pistachio, stone fruit, Brussels sprouts, groundnut, horse radish, tobacco, and red pepper. In particular, Ve polynucleotides can be isolated from Solanaceous plants. For instance, as discussed in detail in Example 2 herein, the inventors have now mapped a highly active Verticillium wilt resistance gene Vc in *Solanum chacoense*, a wild potato variety, to the same position on chromosome IX as Ve1 occurs in tomato. Further, complete linkage between Vc and Verticillium wilt resistance was observed, and Vc hybridized with a probe comprising a portion of Ve1.1. Moreover, sequence alignment analysis of the Ve1.2 deduced amino acid sequence and a partial deduced amino acid sequence of Vc, having 327 amino acid residues, revealed 72.48% sequence identity. Hence, it appears that Vc and Ve1 may be related Ve polynucleotides.

The Ve polynucleotides depicted in SEQ ID NOS: 1, 3, 5 and 7, and the partial Ve polynucleotide sequence depicted in SEQ ID NO: 13 can be used to construct probes for use in nucleic acid hybridization assays with genomic DNA or complementary DNA ("cDNA") libraries to identify homologous nucleic acid sequences. The principle of hybridization analysis is that a single-stranded DNA or RNA molecule, having a defined sequence, can base-pair with a second DNA or RNA molecule having a complementary sequence to the probe, and which is immobilized. The stability of the probe/target sequence hybrid is dependent on the extent of base pairing that occurs. Techniques for constructing primers and probes, for making recombinant DNA libraries, and for performing nucleic acid hybridization, are well known in the art.

In order to construct a probe, the exemplified Ve polynucleotides can be used first to design a pair of primers. Alternately, degenerate primers may be designed based on the exemplified Ve polypeptides (SEQ ID NOS: 2, 4, 6 and 8), or the exemplified partial Ve polypeptide (Vc) depicted in SEQ ID NO: 14. The primers are typically obtained by using chemical DNA synthesis to form oligonucleotides of about 30 nucleotides. The primers may be based on any part of the exemplified Ve polynucleotides or Ve polypeptides. Known sequence alignment techniques, as described hereinbefore, can be used to identify conserved regions, which may be preferred sources for primers.

The primers can then used to amplify by polymerase chain reaction ("PCR") a homologous sequence from polynucleotides isolated from a plant that may be either susceptible or resistant to Verticillium species. The plant may conveniently be a resistant tomato strain as exemplified herein. The amplified sequence is obtained for subsequent use as a probe in a hybridization assay. Hybridization probes generally have a minimum length of about 200 nucleotides, although smaller probes (e.g. as little as 50 nucleotides in length) can also be used.

To obtain the probe by PCR, double stranded DNA to be amplified is denatured by heating. In the presence of DNA polymerase, excess deoxyribonucleoside triphosphates ("dNTPs"), buffers, salts, and excess single-stranded oligonucleotide primers (based on the exemplified Ve polynucleotides or Ve polypeptides), new DNA synthesis occurs. The primers hybridize to opposite strands of the DNA, and DNA polymerase catalyzes the extension of new strands in the 5' to 3' direction across the DNA segment bounded by the primers. The first cycle of synthesis results in new strands of indeterminate length which, like the parental strands, can hybridize to the primers in the next cycle of denaturation and annealing. These products of indeterminate length build up only arithmetically during subsequent cycles of denaturation, annealing, and DNA synthesis. But discrete products (the target sequence), which are the length of the portion of the parental strands between the 5' ends of the primers, accumulate at an exponential rate, doubling in each cycle of denaturation, annealing and DNA synthesis. Typically, between 20 and 40 cycles are used.

The amplified probe sequence may then be purified by gel electrophoresis. Alternatively, the probe sequence can be cloned into a plasmid and maintained therein, then restricted out of the plasmid and purified by gel electrophoresis. The probe is typically then labeled by, for instance, radiolabeling or biotin-labeling, to permit ready visualization.

The probes based on the exemplified Ve polynucleotide or Ve polypeptide sequences can be used to probe a genetic library of a resistant plant strain. As discussed earlier, a wide variety of plant species may be used as the source of the genetic library. Any resistant strain of a plant species that is known to be affected by Verticillium wilt is a likely candidate for the isolation of Ve polynucleotides. Libraries may be obtained from commercial sources or constructed by known techniques. Genomic libraries are generally constructed by digesting genomic DNA to fragments of manageable size using restriction endonucleases, packaging the genomic DNA fragments into vectors such as bacteriophage λ vectors or cosmid vectors, and introducing the recombinant vectors into suitable host cells (generally *E. coli*). Sufficient numbers of clones are generated to ensure that the particular sequence of interest is represented. The construction of cDNA libraries is similar, but commences with the generation of a double-stranded DNA copy of messenger RNA ("mRNA") from plant tissues of interest through reverse transcription. A primer is annealed to the mRNA, providing a free 3' end that can be used for extension by the enzyme reverse transcriptase. The enzyme engages in the usual 5'-3' elongation, as directed by complementary base pairing with the mRNA template to form a hybrid molecule, consisting of a template RNA strand base-paired with the complementary cDNA strand. After degradation of the original mRNA, a DNA polymerase is used to synthesize the complementary DNA strand to convert the single-stranded cDNA into a duplex DNA.

In a common approach to hybridization analysis, once the appropriate library is constructed, the library is plated out, transferred to a solid support membrane such as a nitrocellulose filter or nylon membrane, and hybridized to the labeled probe.

All hybridization methods (discussed in detail in Sambrook et al., 1989; and in Ausubel et al., 1990, 1999) depend on the ability of denatured DNA to re-anneal when complementary strands are present in an environment near, but below, their melting temperature ($T_m$), the temperature at which fifty percent of existing DNA duplex molecules are dissociated into single strands. A number of annealing reactions occur during hybridization. These include: annealing of the probe to homologous DNA sequences; mis-matched annealing of the probe to partially homologous sequences; and non-sequence specific interactions, which result in background noise. Mis-matched sequences form less stable hybrids than do completely homologous sequences. As a general rule, the $T_m$ of a double-stranded DNA molecule decreases by 1–1.5° C. with every 1% decrease in homology. Increases in temperature, and decreases in salt concentration disfavour annealing, and increase the stringency of the assay. Therefore, hybridization and wash conditions can be adjusted to achieve desired levels of annealing.

Hybridization is typically carried out in solutions of high ionic strength (e.g. 6×SSC (sodium chloride/sodium citrate buffer) or 6×SSPE (20×SSPE=3.0 M NaCl, 0.2 M NaH2PO4.H2O, 20 mM EDTA, pH 7.4)) at a temperature 20–25 ° C. below $T_m$. For Na$^+$ concentrations in the range of 0.01 M to 0.4 M, and G+C content from about 30–70%, $T_m$ of hybrids of greater than 100 nucleotides in length can be estimated by the equation Tm=81.5° C.−16.6($\log_{10}$ [Na$^+$])+0.41(%G+C)−0.63(% formamide)−(600/1), where 1=the length of the hybrid in base pairs. This equation applies to the "reversible" $T_m$ defined by measurement of hyperchromicity at OD$_{257}$. The "irreversible" $T_m$, which is more important for autoradiographic detection of DNA hybrids is usually 7–10° C. higher. (Sambrook et al., 1989). A convenient formula for estimating hybridization temperature ($T_h$) provided in product literature for NYTRAN brand nylon membranes is $T_h$=$T_m$−5° C.=2° C. (A–T bp)+4° C. (G–C bp)−5° C. To avoid background problems, hybridization time and the amount of probe used should be minimized. The probe preferably has a high specific activity and a length of at least about 50 nucleotides.

Washing is performed to remove excess probe, as well as probes that are bound as mis-match hybrids having less than a desired homology level. Washing proceeds in the order from least stringent to most stringent conditions. The stringency of the wash conditions can be varied by adjusting the temperature and salt concentrations of the wash solution. These conditions can be determined empirically by preliminary experiments in which samples of the DNA to be probed are immobilized on filters, hybridized to the probe, and then washed under conditions of different stringencies. By way of illustration, a typical low stringency wash may be conducted at room temperature in a solution of 2×SSC and 0.1% SDS (sodium dodecyl sulfate). A typical high stringency wash may be conducted at 68° C. in a solution of 0.1×SSC and 0.5% SDS.

Clones that hybridize with the probe at the desired stringency level can then be rescued or isolated, and then sequenced, again using known techniques. As discussed earlier, comparison of the newly isolated sequence with the exemplified Ve polynucleotide sequences can be performed visually, or by using known algorithms and software packages. Those sequences exhibiting at least 40% homology to the exemplified Ve polynucleotides can then be tested to determine whether they are functional to confer on a susceptible plant resistance to Verticillium species. A suitable test is the complementation test described in Example 1herein. Cells or tissues of a susceptible plant are transformed with the polynucleotide of interest (e.g. as described by De Block, 1988) and transformed plants regenerated. The plants are inoculated with a strain of Verticillium which causes Verticillium wilt in the susceptible plant variety. The inoculated plants are examined over an appropriate time course (e.g. at four weeks after inoculation, then at weekly intervals for an additional four weeks) for symptoms of Verticillium wilt. Preferably, control plants such as susceptible non-transformed plants or susceptible plants transformed only with vector DNA are also inoculated with the disease-causing Verticillium strain and! then monitored for disease symptoms. Delayed or reduced disease symptoms are indicative that the isolated polynucleotide comprises a functional Ve polynucleotide.

The exemplified Ve polynucleotides and Ve polypeptides can be used in conjunction with other known techniques to obtain Ve polynucleotides from genomic DNA, cDNA, RNA, proteins, sequence databases, or plant cells or tissues. For example, using primers derived from the exemplified Ve1.1 or Ve1.2 sequences, Ve polynucleotides can be amplified from genomic DNA, cDNA or genomic or cDNA libraries of tomato plants or other plant species (Leister et al., 1996).

In a further alternative method, known immunodetection techniques employing antibodies specific to the Ve1.1 and Ve1.2 polypeptides, or the partial Vc polypeptide, can be used to screen plant cells, tissues, or extracted proteins of interest for the presence of related Ve polypeptides (Sambrook et al., 1989).

Again, such sequences can then be tested by the complementation tests described in Example 1 herein, to determine whether they function to confer on plants resistance to Verticillium species.

Additionally, those of skill in the art, through standard mutagenesis techniques, in conjunction with the complementation tests described in Example 1 herein, can obtain altered Ve polynucleotides and test them for the property of conferring, on plants resistance to Verticillium species. Useful mutagenesis techniques known in the art include, without limitation, oligonucleotide-directed mutagenesis, region-specific mutagenesis, linker-scanning mutagenesis, and site-directed mutagenesis by PCR (see e.g. Sambrook et al., 1989 and Ausubel et al., 1990, 1999).

In obtaining, variant Ve polynucleotides, those of ordinary skill in the art will recognize that proteins may be modified by certain amino acid substitutions, additions, deletions, and post-translational modifications, without loss or reduction of biological activity. In particular, it is well-known that conservative amino acid substitutions, that is, substitution of one amino acid for another amino acid of similar size, charge, polarity and conformation, are unlikely to significantly alter protein function. The 20 standard amino acids that are the constituents of proteins can be broadly categorized into four groups of conservative amino acids on the basis of the polarity of their side chains R- groups) as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein.

As shown in FIG. 9, Ve1.1 and Ve1.2, while both are functional to confer on plants resistance to Verticillium species, have sequence identity or homology of only about 84%. Those amino acids that are not identical are likely not essential to protein function. Hence, variation at these amino acids likely will not negatively affect the biological activity of Ve1.2 or Ve1.2. Further, those amino acids that are not identical, but that are similar, likely can be replaced by other similar amino acids, as discussed in the preceding paragraph, without loss of function.

Exemplified Ve polynucleotides isolated from a strain of *Lycopersicon esculentum* which is resistant to *Verticillium dahliae* have been transformed into *Solanum tuberosum* strains that are susceptible to infection by *V. albo-atrum*, resulting in functional complementation. The transformed *Solanum tuberosum* strains displayed reduced disease symptoms following inoculation with *V. albo-atrum* relative to non-transformed plants, illustrating that Ve polynucleotides of the invention are useful for conferring resistance to various Verticillium species on a range of plants. Ve polynucleotides of the invention can also be used to confer resistance to Verticillium species in all higher plants which are susceptible to infection by Verticillium species, including, without limitation, tomato, potato, hop, alfalfa, strawberry, sainfoin, runner bean, broad bean, pea, clover, cucumber, canola, cotton, dahlia, mint species, vine, eggplant, olive, pistachio, stone fruit, Brussels sprouts, groundnut, horse radish, tobacco, and red pepper.

In preparation for transformation of plant cells with Ve polynucleotides, recombinant vectors are prepared. The desired recombinant vector generally comprises an expression cassette designed for initiating transcription of the Ve polynucleotide in the transformed plant. Additional sequences are included to allow the vector to be cloned in a bacterial or phage host.

The vector will preferably contain a prokaryotic origin of replication having a broad host range. A selectable marker should also be included to allow selection of bacterial cells bearing the desired construct. Suitable prokaryotic selectable markers include resistance to antibiotics such as ampicillin.

Other DNA sequences encoding additional functions may also be present in the vector, as is known in the art. For instance, in the case of Agrobacterium mediated transformation, T-DNA sequences will also be included for subsequent transfer to plant chromosomes.

For expression in plants, the recombinant expression cassette will preferably contain, in addition to the desired sequence, a plant promoter region, a transcription initiation site (if the sequence to be transcribed lacks one), and a transcription termination sequence. Unique restriction enzyme sites at the 5' and 3' ends of the cassette are typically included to allow for easy insertion into a pre-existing vector. Sequences controlling eukaryotic gene expression are well known in the art.

The particular promoter used in the expression cassette is not critical to the invention. Any of a number of promoters which direct transcription in plant cells is suitable. The promoter can be either constitutive or inducible. A number of promoters which are active in plant cells have been described in the literature. These include the nopaline synthase (NOS) and octopine synthase (OCS) promoters (which are carried on tumour-inducing plasmids of *Agrobacterium tumefaciens*), the caulimovirus promoters such as the cauliflower mosaic virus (CaMV) 19S and 35S and the figwort mosaic virus 35S-promoters, the light-inducible promoter from the small subunit of ribulose-1,5-bis-phosphate carboxylase (ssRUBISCO, a very abundant plant polypeptide), and the chlorophyll a/b binding protein gene promoter. All of these promoters have been used to create various types of DNA constructs which have been expressed in plants. A particularly preferred promoter is the endogenous promoter of the Ve polynucleotide. For instance, with respect to Ve1.1 and Ve1.2, the endogenous promoters in SEQ ID NO: 10, are particularly preferred.

The entirety of the endogenous promoter region depicted in SEQ ID NO: 10 need not be used. A relatively short sequence within SEQ ID NO: 10, of as little as 50 nucleotides, may be functional as a promoter, provided that the elements essential to promoter function are included. The promoter region contains sequence of bases that signals RNA polymerase to associate with the DNA, and to initiate the transcription of mRNA using one of the DNA strands as a template to make a corresponding complimentary strand of RNA. Promoter sequence elements include the TATA box consensus sequence (TATAAT), which is usually 20 to 30 base pairs (bp) upstream (by convention −30 to −20 bp relative to the transcription start site) of the transcription start site. In most instances the TATA box is required for accurate transcription initiation: The TATA box is the only upstream promoter element that has a relatively fixed location with respect to the start point. The CAAT box consensus sequence is centered at −75, but can function at distances that vary considerably from the start point and in either orientation. Hence, the TATA box and CAAT box may be within 50 nucleotides of each other. Another common promoter element is the GC box at −90 which contains the consensus sequence GGGCGG. It may occur in multiple copies and in either orientation. Other sequences conferring tissue specificity, response to environmental signals, or maximum efficiency of transcription may also be found in the promoter region. Such sequences are often found within 400 bp of transcription initiation size, but may extend as far as 2000 bp or more. In heterologous promoter/structural gene combinations, the promoter is preferably positioned about the same distance from-the heterologous transcription start site as it is from the transcription start site in its natural setting. However, some variation in this distance can be accommodated without loss of promoter function.

Sequences within SEQ ID NO: 10 that provide promoter function can be readily identified. A chimeric construct is created, which includes the fragment of SEQ ID NO: 10 to be tested for promoter function, operably linked to a reporter gene. Protoplasts are transformed with the chimeric construct, and the expression of the reporter gene is measured. High expression of the reporter gene is indicative of strong promoter function. A suitable reporter gene for the analysis of plant gene expression is the bacterial gene uidA, encoding β-glucuronidase ("GUS"). GUS expression can be conveniently quantified through a highly sensitive non-radioactive assay using the fluorogenic substrate 4-MUGluc, as described by Gelvin et al. (1994).

In addition to a promoter sequence, the expression cassette preferably also contains a transcription termination region downstream of the structural gene to provide for efficient termination. The termination region may be obtained from the same gene as the promoter sequence, from a different gene, or may be the endogenous termination region of the Ve polynucleotide.

Polyadenylation sequences are also commonly added to the vector construct if the mRNA encoded by the structural gene is to be efficiently translated (Alber et al., 1982). Polyadenylation is believed to have an effect on stabilizing mRNAs. Polyadenylation sequences include, but are not limited to the Agrobacterium octopine synthase signal (Gielen et al., 1984) or the nopaline synthase signal (Depicker et al., 1982).

The vector will also typically contain a selectable marker gene by which transformed plant cells can be identified in culture. Typically, the marker gene encodes antibiotic resistance. These markers include resistance to G418, hygromycin, bleomycin, kanamycin, and gentamycin. After transforming the plant cells, those cells containing the vector will be identified by their ability to grow in a medium containing the particular antibiotic.

The recombinant vector is assembled by employing known recombinant DNA techniques (Sambrook et al., 1989; Ausubel et al., 1990, 1999). Restriction enzyme digestion and ligation are the basic steps employed to join two fragments of DNA. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The recombinant vector is typically assembled in stages employing rounds of restriction, ligation, and transformation of E. coli.

Recombinant vectors can be introduced into plant cells by a variety of known techniques. Although in the exemplified case potato plant stem and leaf sections were transformed via inoculation with Agrobacterium tumefaciens carrying the Ve polynucleotide sequence linked to a binary vector, direct transformation techniques which are known in the art can also be used to transfer the recombinant DNA. For instance, the vector can be microinjected directly into plant cells. Alternatively, nucleic acids may be introduced to the plant cell by high velocity ballistic penetration by small particles having the nucleic acid of interest embedded within the matrix of the particles or on the surface. Fusion of protoplasts with lipid-surfaced bodies such as minicells, cells or lysosomes carrying the DNA of interest can be used. The DNA may also be introduced into plant cells by electroporation, wherein plant protoplasts are electroporated in the presence of plasmids carrying the expression cassette, or by polyethylene glycol ("PEG")-mediated transformation. A review of some of the techniques for incorporating foreign DNA into plant cells is found in Gelvin et al. (1994).

In contrast to direct transformation methods, the exemplified case involves vectored transformation using Agrobacterium tumefaciens. Agrobacterium tumefaciens is a Gram-negative soil bacteria which causes a neoplastic disease known as crown gall in dicotyledonous plants. Induction of tumours is caused by tumour-inducing plasmids known as Ti plasmids. Ti plasmids direct the synthesis of opines in the infected plant. The opines are used as a source of carbon-and/or nitrogen by the Agrobacteria.

The bacterium does not enter the plant cell, but transfers only part of the Ti plasmid, a portion called T-DNA, which is stably integrated into the plant genome, where it expresses the functions needed to synthesize opines and to transform the plant cell. Vir (virulence) genes on the Ti plasmid, outside of the T-DNA region, are necessary for the transfer of the T-DNA. The vir region, however, is not transferred. In fact, the vir region, although required for T-DNA transfer, need not be physically linked to the T-DNA and may be provided on a separate plasmid.

The tumour-inducing portions of the T-DNA can be interrupted or deleted without loss of the transfer and integration functions, such that normal and healthy transformed plant cells may be produced which have lost all properties of tumour cells, but still harbour and express certain parts of T-DNA, particularly the T-DNA border regions. Therefore, modified Ti plasmids, in which the disease causing genes have been deleted, may be used as vectors for the transfer of the Ve polynucleotide constructs of the present invention into plants.

Transformation of plants cells with Agrobacterium and regeneration of whole plants typically involves either co-cultivation of Agrobacterium with cultured isolated protoplasts or transformation of intact cells or tissues with Agrobacterium. In the exemplified case, potato stem and leaf sections were transformed with Agrobacterium.

Alternatively, cauliflower mosaic virus (CaMV) may be used as a vector for introducing DNA into plants of the Solanaceae family. For instance, U.S. Pat. No. 4,407,956 to Howell teaches the use of cauliflower mosaic virus DNA as a plant vehicle.

After transformation, transformed plant cells or plants carrying the recombinant DNA are identified. A selectable marker, such as antibiotic resistance, is typically used. In the exemplified case, transformed plant cells were selected by growing the cells on growth medium containing carbenicillin and kanamycin. Other selectable markers will be apparent to those skilled in the art. For instance, the presence of opines can be used to identify transformants if the plants are transformed with Agrobacterium.

Expression of the foreign DNA can be confirmed by detection of RNA encoded by the inserted DNA using well known methods such as Northern blot hybridization. The inserted DNA sequence can itself be identified by Southern blot hybridization or by PCR (see, generally, Sambrook et al., 1989).

Generally, after it is determined that the transformed plant cells carry the recombinant DNA, whole plants- are regenerated. Techniques for regenerating differentiated transgenic plants from-transformed cells are well known in the art and are described in detail in such references as Gelvin et al. (1994). In the exemplified case, potato stem and leaf sections were inoculated with a culture of Agrobacterium tumefaciens carrying the desired Ve polynucleotide and carbenicillin and kanamycin marker genes. Transformants were selected on a growth medium containing carbenicillin and kanamycin. After transfer to a suitable medium for shoot induction, shoots were transferred to a medium suitable for rooting. Plants were then transferred to soil and hardened off. The plants regenerated in culture were transplanted and grown to maturity under greenhouse conditions.

The resistance of the regenerated transgenic plants to Verticillium species may then be tested. An aggressive isolate of a Verticillium wilt-causing pathogen such as *Verticillium albo-atrum* is isolated from infected plants, and cultured. Transgenic plants containing the Ve polynucleotide and control plants are then inoculated with a spore suspension of the cultured pathogen. The control plants may be wild type Verticillium-sensitive plants, or transgenic plants transformed only with vector DNA which does not contain the Ve polynucleotide insert. Disease reaction ratings can be measured visually, over an appropriate time course. For instance, in potato plants, the first observations may be made four weeks after inoculation, and conducted thereafter at weekly intervals for another four weeks. Plants that show delayed or reduced disease symptoms such as wilting, chlorosis, and necrosis of the leaves, relative to control plants, are rated as being resistant to Verticillium species.

Recombinant DNA procedures used for practicing the invention and which are not described in detail herein involve standard laboratory techniques that are well known in the art and are described in standard references such as Sambrook et al. (1989) or Ausubel et al. (1990, 1999). Generally, enzymatic reactions involving DNA ligase, DNA polymerase, restriction endonucleases and the like are performed according to the manufacturer's specifications. Abbreviations and nomenclature employed herein are standard in the art and are commonly used in scientific publications such as those cited herein.

The invention is further illustrated by the following non-limiting Examples.

EXAMPLE 1

Genetic experiments with near-isogenic lines of *Lycopersicon esculentum* have previously identified a codominant RAPD marker within 3.2±0.3 cM of Ve1, a Verticillium wilt resistance gene which confers resistance to race 1 of *Verticillium dahliae* (Kawchuk et al., 1994). Sequences of the RAPD were used to develop SCARs that were determined by high resolution mapping to be within 0.67±0.49 cM or 290 kb of Ve1 (Kawchuk et al., 1998).

For map-based cloning of Ve1, the SCAR sequences were used as hybridization probes to identify λ clones that possess contiguous, overlapping inserts of *Lycopersicon esculentum* VFN8 genomic DNA (FIG. 1). Genomic clones were isolated by screening a λ EMBL3 library (Clonetech Laboratories, Inc., Palo Alto, Calif., USA) of the *V. dahliae* race 1 resistant *L. esculentum* germplasm VFN8 initially with allele-specific SCARs (GenBank accession Nos. AF029221 and AF029223; Kawchuk et al., 1998). Approximately three copies of the genome, or $2\times10^5$ recombinant plaques, were transferred to duplicate HYBOND $N^+$ membranes and probed. Rescued clones were subcloned into pBluescript SK(−) and sequenced.

Identification of Ve1 involved in vivo functional complementation within the *Solanum tuberosum* ssp. tuberosum variety Désirée that is highly susceptible to *Verticillium albo-atrum.*

Genomic clones linked to Ve1 were cloned into the pBIN 19 binary vector for *Agrobacterium tumefaciens* mediated transformation. Plant transformation was as described by De Block (1988). Neomycin phosphotransferase II ("NPTII") levels were determined by enzyme-linked immunosorbent assay (Agdia Inc., Elkhart, Ind., USA) and enzymatic activity measured by radiolabelling of substrate (Staebell, 1990). Plants propagated in the greenhouse were inoculated with *V. albo-atrum* (Kawchuk et al., 1994). Disease reactions were obtained by challenging a minimum of 10 plants from at least three independent lines of transgenic potato plants for each of the pG1Ve, pG2Ve, pG3Ve, and pC1Ve constructs (FIG. 1). In vivo complementation was initially observed in potato plants transformed with the 6 kb genomic sequence of λ subclone pG1Ve (FIG. 1).

Referring to Table 1, plants transformed with pG1Ve (comprising, in the 5' to 3' direction, SEQ ID NO: 1 from nucleotide 1 to nucleotide 1332, SEQ ID NO: 10 from nucleotide 1 to nucleotide 3477, and SEQ ID NO: 5 from nucleotide 1 to nucleotide 1146) exhibited a delay and reduced disease symptoms following inoculation with *V. albo-atrum*. Improved complementation was observed in plants transformed with genomic subclone pG2Ve (SEQ ID NO: 5 from nucleotide 1 to nucleotide 3159) or pG3V3 (SEQ ID NO: 1 from nucleotide 1 to nucleotide 3417). In contrast, infection, wilt, chlorosis, necrosis and eventual death of all untransformed plants (Désirée) and plants transformed only with the binary vector DNA (pBI121 or pBIN19) occurred within a few weeks of inoculation.

To identify expressed sequences and the Ve1 locus, the λ subclones were sequenced, and pG1Ve used to probe a *Lycopersicon esculentum* cDNA library of the Verticillium wilt-resistant variety Craigella. Genomic DNA and cDNA sequences were determined with a BIGDYE Terminator Kit (PE Biosystems, Mississauga, Ontario, Canada) and an ABI 377 automated sequencer (PE Biosystems), using primers derived from the genomic sequences and the polylinker cloning site of the vector. A STRATAGENE (La Jolla, Calif., USA) cDNA cloning kit was used to prepare and unidirectionally clone cDNA as described by the manufacturer. Total RNA was isolated from detached leaves of greenhouse propagated *L. esculentum* cultivar Craigella, stressed in 1 mM L-serine for 48 hours. Polyadenylated [poly(A)$^+$] RNA was isolated by oligo(dT) cellulose chromatography. First strand cDNA synthesis was primed with an oligo(dT) linker-primer that contains a Xho I site and transcribed using a RNase H$^-$ reverse transcriptase in the presence of 5-methyl dCTP to hemimethylate the cDNA. Second strand cDNA was prepared using RNase H and DNA polymerase I and the double stranded DNA treated with Klenow before ligation to Eco RI adapters. The cDNA was ligated to Eco RI and Xho I restricted arms of the lambda phage vector Uni-ZAP XR vector. Phage were packaged and used to infect the recA$^-$ *E. coli* XL1-Blue MRF'. Approximately 3×10$^5$ recombinant plaques were transferred to HYBOND N$^+$ membranes and screened with the genomic subclone pG1Ve. Eight cDNA clones were recovered and the pBluescript SK(−) phagemid with the cloned insert excised and recircularized.

Figure 1:
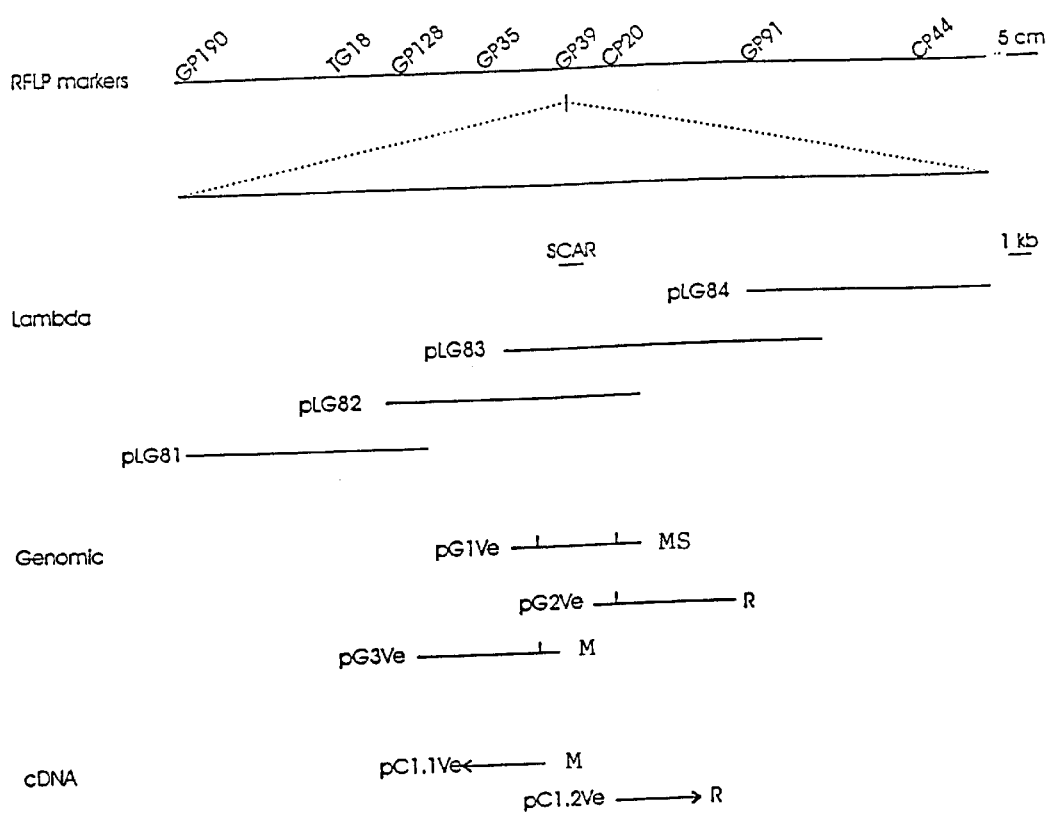
FIG. 1 is a schematic genetic and physical representation of the *L. esculentum* linkage group surrounding Ve1. Analysis of populations segregating for Ve1 identified closely linked co-dominant random amplified polymorphic DNAs ("RAPDs") and allele-specific sequence characterized amplified regions ("SCARs") that map to the region of restriction fragment length polymorphism ("RFLP") GP39. Identification of contiguous λ genomic clones facilitated the subcloning of genomic DNA containing the Ve1 locus.

Genomic sequences confirmed that pG1Ve possessed the SCAR sequence linked to the resistant Ve1 allele and revealed two terminal open reading frames ("ORFs") in pG1Ve homologous to the amino terminal domain of plant and animal receptors that possess leucine-rich repeats. Two cDNA clones, pC1.1Ve (SEQ ID NO: 3 from nucleotide 57 to nucleotide 3473) and pC1.2Ve (SEQ ID NO: 7 from nucleotide 1 to nucleotide 3159), corresponding to the ORFs observed in the genomic subclones were isolated (FIG. 1). Interestingly, the ORF within pG1Ve lacks 751 and 680 amino acids from the C terminus of, respectively, pC1.1Ve (i.e. leaving only amino acids 1–388 of SEQ ID NO: 4) and pC1.2Ve (i.e. leaving only amino acids 1–382 of SEQ ID NO: 8), demonstrating that in vivo complementation can occur without this domain.

To confirm complementation, the cDNA of pC1.1Ve and pC1.2Ve was cloned into the binary vector pBI121 in a sense orientation under transcriptional control of the cauliflower mosaic virus (CaMV) 35S promoter and transformed plants obtained as described for the genomic clones. All plants expressing pC1.1Ve (Ve1.1) and pC1.2Ve (Ve1.2) exhibited resistance to the pathogen, whereas untransformed germplasm and plants transformed with the vector alone were susceptible and expired within a few weeks of inoculation (Table 1).

Sequence analysis of the cDNA and corresponding genomic clones did not detect any introns within the Ve1 ORF. As shown in FIGS. 4A, 4B, and 7, several structural domains were observed within the 1139 and 990 amino acids of Ve1.1 (SEQ ID NO: 4) and Ve1.2 (SEQ ID NO: 8) deduced from the cDNA sequences. Motifs were identified with the PCGENE program (IntelliGenetics Inc.) version 6.85.

Referring to FIGS. 4A and 4B, six domains, A, B, C, D, E, and F, were identified in Ve1.1 (SEQ ID NO: 4). Domain A is a hydrophobic N terminus of 30 amino acids, indicative of a signal peptide that may target the protein to the cytoplasmic membrane (von Heijne, 1985). Domain B is a LRR with a 24 amino acid consensus XXIXNLXXLXX-LXLSXNXLSGXIP (SEQ ID NO: 9) that is often associated with protein-protein interactions and ligand binding. The presence of a glycine within the consensus sequence is consistent with that of extracytoplasmic proteins (Jones, 1994; Song, 1995) and facilitates the recognition of an extracellular pathogen ligand. Thirty five sequences matching the N-glycosylation consensus sequence N(X(S/T) were observed in Ve1.1, within the predicted LRR region. Amino acids in domain C represent a hydrophobic sequence with a predicted α helix secondary structure characteristic of membrane spanning proteins. As frequently observed with type Ia integral membrane proteins, a highly basic region (domain D) follows the hydrophobic domain. Amino acids in domain E include negative residues that define a highly acidic motif similar to PEST sequences observed in cytoplasmic proteins with half-lives of only a few hours (Rogers et al., 1986). The C terminus of Ve1.1 (domain F) concludes with the residues KKF, similar to the KKX motif that functions in animals as a signal for endoplasmic reticulum retention and receptor mediated endocytosis (Jackson et al., 1990).

Referring to FIG. 7, domains A, B, E, C and D, corresponding to the similarly identified domains in Ve1.1, were observed in the Ve1.2 amino acid sequence (SEQ ID NO: 8) deduced from the cDNA sequence. Twenty eight sequences matching the N-glycosylation consensus sequence N(X(S/T) were observed in Ve1.2, within the predicted LRR region.

Various versions of the BLAST algorithm (Altschul et al., 1997) were used to search DNA and protein databases for sequences having similarity to Ve1.1 and Ve1.2. Low homology (less than 40% homology, and generally less than 30% homology) to Ve1 was observed in several plant proteins with LRRs such as receptor-like protein kinases ("RLPKs"), antifungal polygalacturonase-inhibiting proteins ("PGIPs"), disease resistance genes that probably produce cytoplasmic proteins, and the genes Xa and Cf (Jones, 1994; Song, 1995) that appear to produce proteins with an extracytoplasmic domain that interacts with an extracellular ligand. Unlike Xa, Ve1 does not include a protein kinase and therefore represents a second member of the Cf class of pathogen resistance genes. Although Ve1 structurally resembles the Cf resistance genes from tomato, there is little amino acid homology other than the conserved residues of the leucine-rich domain.

Like Ve1, members of the cytokine receptor superfamily posses an extracellular ligand-binding domain, a short single pass transmembrane sequence and a cytoplasmic domain that lacks a kinase motif (Ihle, 1995). Recent crystallographic evidence reveals that hematopoietic and other cytokine receptors are capable of ligand-independent dimerization via ligand binding residues within LRR sequences (Livnah et al., 1999). The unexpected in vivo fragment complementation observed with the Ve1 N terminus suggests a similar interaction is occurring with a homologous protein in the susceptible potato plants to produce a heterodimer capable of extracellular ligand recognition and cytoplasmic signaling. This model is supported by the detection of a constitutively expressed Ve1 homolog in susceptible tomato and potato genotypes (FIG. 8).

To detect the Ve1 homolog, polyadenylated [poly(A)$^+$] RNA was isolated by oligo(dT) cellulose chromatography from leaves three days post-inoculation, separated on a 1.4% formaldehyde gel, transferred to HYBOND N$^+$ membranes and hybridized with pC1Ve. Heterodimerization between a full-length trans-membrane molecule and a truncated homolog lacking the cytoplasmic domain has been reported to produce a functional bacterial Tar chemoreceptor (Gardena et al., 1996) and monocot Xa21 resistance receptor (Wang et al., 1998).

Cytoplasmic signaling by Ve1 may be analogous to that of the erythropoietin cytokine receptor. Preformed dimers on the cell surface facilitate transmission of a ligand-induced conformational change from the extracellular to the cytoplasmic domain and subsequent signal transduction (Remy et al., 1999). The cytoplasmic domain interacts with kinases that link ligand binding to tyrosine phosphoylation of various signaling proteins and transcription activation factors. A similar model has been proposed for the kinase encoded by the Pto resistance gene that lacks a receptor domain (Martin, 1993).

Verticillium albo-atrum and Fusarium oxysporum are both necrotrophic fungi that invade roots and vascular tissue, and it is somewhat surprising that resistance to these pathogens is conferred by structurally distinct receptors. The I2 resistance gene for F. oxysporum isolated from tomato (Ori et al., 1997; Simons et al., 1998) resembles the Arabidopsis resistance gene RPS2 (Bent et al., 1994; Mindrinos et al., 1994) and RPM1 (Grant et al., 1995) for Pseudomonas syringae. PR proteins of this class are intracellular and possess an N terminal leucine zipper, nucleotide binding site and a leucine rich repeat. Since the Ve belongs to the same class of receptors as Cf, a gene that confers race-specific resistance to a biotrophic extracellular fungus without haustoria, factors other than infection epidemiology must determine the structure of receptors involved in specific host-pathogen interactions.

Resistance to different pathogen species is contrary to the traditional view of a highly specific interaction with race defining R genes. The results reported herein demonstrate that while the tomato Ve1 gene has a specificity capable of distinguishing races 1 and 2 of Verticillium dahliae, the gene retains the capacity to recognize another Verticillium species in a different host. This pleotropic resistance resembles that observed with the Mi gene which confers resistance to nematodes and aphids (Milligan et al., 1998; Rossi et al., 1998; Vos et al., 1998) and shares the ability of some R genes to retain biological activity in other plant genera (Rommens et al., 1995; Thilmony et al., 1995; Hammond-Kosack et al., 1998; Whitham, 1996). Several Verticillium species infect many agricultural plants, and this pleiotropic host independent complementation by Ve1 should therefore be of considerable value.

TABLE 1

Verticillium wilt disease ratings of transformed potato plants at three weeks postinoculation.

| Line (N = 30) | Live Plants (%) | Disease Rating* |
|---|---|---|
| Desiree | 0 | 5.0 (S) |
| pBI121 | 0 | 5.0 (S) |
| pBIN19 | 0 | 5.0 (S) |
| pG1Ve | 26 | 4.1 (MS) |
| pG2Ve | 90 | 0.3 (R) |
| pG3Ve | 53 | 2.2 (M) |
| pC1.1Ve | 40 | 2.8 (M) |
| pC1.2Ve | 87 | 0.4 (R) |

*Rating scale is based on percentage of plant exhibiting necrosis and chlorosis: 0 < 20%; 1 = 20 to 40%; 2 = 40 to 60%; 3 = 60 to 80%; 4 = >80%; 5 = 100%. S = susceptible; MS = moderately susceptible; M = moderate; R = resistant.

EXAMPLE 2

A single dominant resistance gene (Vc) for verticillium wilt was previously identified in Solanum chacoense (Lynch et al. 1997). Herein, we used this segregating population to map Vc versus Ve in tomato. This was accomplished by restricting extracted progeny and parental DNA with Taq I and probing the Southern blots. The Southern blots were probed with Ve1.1, and complete linkage was observed with verticillium wilt resistance indicating that not only did Ve1.1 hybridize to a homologous gene in S. chacoense but this gene was also linked to Vc.

A potato genomic library (titre 6.8×10 PFU/ml) (Clontech, Palo Alto Calif., US) of Desiree constructed in EMBL-3 SP6/T7 was probed with Ve1.1 and three genomic clones isolated. The primary screening was carried out by preparing duplicate plaque lifts of the plated library and probing the supported nitrocellulose membranes with Ve1.1 labelled with $p^{32}$. Four washes were performed using 2×SSC/0.1% SDS. Two washes were at 42° C. for 15 minutes each and the remaining two washes were at 65° C. also for 15 minutes. Plaques yielding positive signals on both membranes were lifted from the plate and eluted into SM buffer. This eluted lambda was used in the secondary screen following the above procedure except that the third and forth washes were performed at 58° C. for 15 minutes each. Plaques with a positive signal on duplicate membranes was removed and the lambda eluted. Lambda lysates were prepared from these secondary eluents and DNA was purified from them.

Oligonucleotide primers synthesized to detect Ve1.1 were used to PCR amplify related sequences that may be present in the three rescued genomic clones. Polymerase chain reaction was carried out on the three lambda DNA templates, at various dilutions, to determine if the inserted DNA within these constructs contained the gene of interest. We used primers that were previously generated to construct a Ve1 probe. Ve1 probe primers: 3B2F4 5'-AAT TCA CTC AAC GGG AGC CTT CCT GC-3'(SEQ ID NO: 11) and 3B2R4-2 5'-TCA AGG CAT TGT TAG AGA AAT CAA G 3'(SEQ ID NO: 12). The reaction mixture contained: 17 ul $H_2O$, 2.5 ul 10×PCR buffer, 1.0 ul 2.5 mM dNTPs, 1.5 ul 25 mM $MgCl_2$, 0.2 ul Amplitaq Gold, 1.0 ul primer 3B2F4, 1.0 ul primer 3B2R4-2 and 1.0 ul template (for a total volume of 25 ul). The reaction conditions were 1 cycle at 95° C. for 9 min.; 30 cycles at 94° C. for 1 min., 60° C. for 1 min., and 72° C. for 1 min. 30 sec.; and 1 cycle at 72° C. for 10 min. A 15 ul aliguot from each reaction tube was loaded onto a 1% agarose gel with EtBr added in and ran at 65 volts for 90 min. A DNA fragment of approximately 850 bp was detected from each genomic clone indicating the presence of a Ve1.1-related sequence that is most likely Vc. Sequencing of this fragment by the methods described in Example 1 herein identified a 982 base pair partial Vc genomic sequence having the nucleotide sequence depicted in SEQ ID NO: 13.

REFERENCES

Alber et al. 1982. Mol. And Appl. Genet. 1:419–434.
Altschul, S. F. et al. 1990. J. Mol. Biol. 215:403.
Altschul, S. F. et al. 1997. Nucleic Acids Res. 25: 3389–3402.
Ausubel, F. M. et al. 1990. Current protocols in molecular biology. Green Publishing and Wiley-Interscience, New York.
Ausubel, F. M. et al. 1999. Current Protocols in Molecular Biology. John Wiley & Sons, Inc., New York.
Bent, A. F. et al. 1994. Science 265:1856.
De Block, M. 1988. Theor. Appl. Genet. 76: 767.
Depicker et al. 1982. Mol. And Appl. Genet. 1:561–573.
Dixon, M. S. et al. 1998. The Plant Cell. 10:1915–1925.
Domsch, K. H, W. Gams, T. Anderson. 1980. Compendium of Soil Fungi. Academic Press. London.
Flor, H. H. 1946. J. Agric. Res. 73:335.
Gardina, P. and Manson, M. D. 1996. Science. 274:425.
Gielen et al. 1984. EMBO J. 3:835–846.
Grant, M. R. et al. 1995. Science. 269:843.
Hammond-Kosack et al. 1998. Plant Cell. 10:1251.
Ihle. 1995 . Nature. 377:591.
Jackson et al. 1990. EMBO J.9:3153.
Johal et al. 1992. Science. 258:985.
Jones, D. A. et al. 1994. Science 266:789.

Kawchuk, L. M., Hachey, J. and Lynch, D. R. 1998. Genome 41:91.
Kawchuk, L. M., Lynch, D. R., Hachey, J., and Bains, P. S. 1994. Theor. Appl. Genet. 89:661–664.
Lawrence et al. 1995. N. Plant Cell. 7:1195.
Leister et al. 1996. Nature Genetics. 14:421.
Livnah et al. 1999. Science. 283:987.
Lynch et al. 1997. Plant Disease. 81:10.
Martin, G. B. 1993. Science. 262:1432.
Milligan, S. B. et al. 1998. Plant Cell. 10:1307.
Mindrinos et al. 1994. Cell. 78:1089.
Ori, N. 1997. Plant Cell 9:521.
Gelvin S. B. et al. 1994. Plant Molecular Biology Manual. Kluwer Academic Publishers. Belgium.
Remy et al. 1999. Science. 283:990.
Rogers, S., Wells, R. and Rechsteiner, M. 1986. Science 234:364.
Rommens, C. M. T. et al. 1995. Plant Cell 7:1537
Rossi et al. 1998. Proc. Nat. Acad. Sci. USA. 95:9750.
Sambrook, J., Fritsch, E. F. and Maniatis, T. 1989. Molecular Cloning, A Laboratory Manual. Cold Spring Harbor Laboratory Press.
Simons et al. 1998. Plant Cell. 10:1055.
Song, W.-Y. 1995. Science 270:1804.
Staebell, M. 1990. Annal. Biochem. 185:319.
Thilmony, R. L. et al. 1995. Plant Cell. 7:1529
von Heijne G. 1985. Mol. Biol. 184:99.
Vos, P. et al. 1998. Nat. Biotechnol. 16:1365.
Wang, G. L. et al. 1998.. Plant Cell. 10:765.
Whitham, S. et al. 1.996. Proc. Natl. Acad. Sci. U.S.A. 93:8776.

All publications mentioned in this specification are indicative of the level of skill in the art to which this invention pertains. To the extent they are consistent herewith, all publications mentioned in this specification are herein incorporated by reference to the same extent as if each individual publication was specifically and individually indicated to be incorporated by reference.

Although the foregoing invention has been described in some detail by way of illustration and example, for purposes of clarity and understanding it will be understood that certain changes and modifications may be made without departing from the scope or spirit of the invention as defined by the following claims.

What is claimed is:

1. A purified and isolated polynucleotide, the expression of which in a plant confers on said plant resistance to at least one Verticillium species, wherein said polynucleotide encodes a polypeptide comprising the amino acid sequence depicted in SEQ ID NO: 4.

2. The purified and isolated polynucleotide according to claim 1, wherein said polynucleotide comprises nucleotides 57 to 3473 of SEQ ID NO: 3.

3. A purified and isolated polynucleotide, wherein the expression of said polynucleotide in a plant confers on said plant resistance to at least one Verticillium species, and wherein said polynucleotide encodes a polypeptide comprising an amino acid sequence having at least 80% identity to the amino acid sequence depicted in SEQ ID NO: 4.

4. The purified and isolated polynucleotide according to claim 3, wherein the at least one Verticillium species is a race 1 Verticillium species.

5. The purified and isolated polynucleotide according to claim 3, wherein the at least one Verticillium species is selected from the group consisting of *Verticillium dahliae* race 1 and *Verticillium albo-atrum*.

6. The purified and isolated polynucleotide according to claim 3, wherein said polynucleotide is obtained from a Solanaceous plant.

7. The purified and isolated polynucleotide according to claim 6, wherein said polynucleotide is obtained from Lycopersicon species.

8. The purified and isolated polynucleotide according to claim 6, wherein said polynucleotide is obtained from *Lycopersicon esculentum*.

9. A polynucleotide construct comprising in operable linkage the polynucleotide according to any one of claims 1, 2, 3 or 6–8 and a plant expressible promoter.

10. A plant vector comprising the polynucleotide construct of claim 9.

11. The polynucleotide construct according to claim 9, wherein said promoter is heterologous to said polynucleotide.

12. A vector comprising at least one polynucleotide according to any one of claims 1–3 and 6–8.

13. A vector according to claim 12, wherein said vector is a plant vector.

14. A transgenic plant cell which has been transformed with the polynucleotide construct of claim 9 or with the plant vector of claim 10.

15. A transgenic plant, plant seed, or plant embryo which has been transformed with the polynucleotide construct of claim 9 or with the plant vector of claim 10.

16. The transgenic plant, plant seed, or plant embryo according to claim 15, wherein said plant, plant seed, or plant embryo is a tomato, potato, hop, alfalfa, strawberry, sainfoin, runner bean, broad bean, pea, clover, cucumber, canola, cotton, dahlia, mint, vine, eggplant, olive, pistachio, stone fruit, Brussel sprouts, ground nut, horse radish, tobacco, or red pepper plant, plant seed, or plant embryo.

17. The plant, plant seed, or plant embryo according to claim 16, wherein said plant, plant seed, or plant embryo is a Solanaceous plant, plant seed, or plant embryo.

18. The plant, plant seed, or plant embryo according to claim 17, wherein said plant, plant seed, or plant embryo is a potato plant, plant seed, or plait embryo.

19. A method for producing a transgenic plant that is resistant to at least one Verticillium species, said method comprising the steps of:

a) introducing into a plant cell or plant tissue at least one polynucleotide construct according to claim 9 to produce a transformed plant cell or plant tissue; and b) regenerating a transgenic plant from said transformed plant cell or transformed plant tissue, wherein said transgenic plant is resistant to at least one Verticillium species.

20. The method according to claim 19, wherein said plant is a tomato, potato, hop, alfalfa, strawberry, sainfoin, runner bean, broad bean, pea, clover, cucumber, canola, cotton, dahlia, mint, vine, eggplant, olive, pistachio, stone fruit, Brussel sprouts, groundnut, horse radish, tobacco, or red pepper plant.

21. The method according to claim 20, wherein said plant is a Solanaceous plant.

22. The method according to claim 21, wherein said plant is a potato plant.

\* \* \* \* \*

SEQUENCE LISTING

```
<160> NUMBER OF SEQ ID NOS: 14

<210> SEQ ID NO 1
<211> LENGTH: 3420
<212> TYPE: DNA
<213> ORGANISM: Lycopersicon esculentum
<220> FEATURE:
<221> NAME/KEY: misc_feature
<222> LOCATION: (1)..(3420)
<223> OTHER INFORMATION: Ve1.1 genomic DNA sequence
<220> FEATURE:
<221> NAME/KEY: CDS
<222> LOCATION: (1)..(3420)

<400> SEQUENCE: 1 atg aga ttt tta cac ttt cta tgg atc ttc ttc atc ata ccc ttt ttg      48
Met Arg Phe Leu His Phe Leu Trp Ile Phe Phe Ile Ile Pro Phe Leu
  1               5                  10                  15 caa att tta tta ggt aat gag att tta ttg gtt tcc tct caa tgt ctt      96
Gln Ile Leu Leu Gly Asn Glu Ile Leu Leu Val Ser Ser Gln Cys Leu
             20                  25                  30 gat gat caa aag tca ttg ttg ctg cag ttg aag ggc agc ttc caa tat     144
Asp Asp Gln Lys Ser Leu Leu Leu Gln Leu Lys Gly Ser Phe Gln Tyr
         35                  40                  45 gat tct act ttg tca aat aaa ttg gca aga tgg aac cac aac aca agt     192
Asp Ser Thr Leu Ser Asn Lys Leu Ala Arg Trp Asn His Asn Thr Ser
     50                  55                  60 gaa tgt tgt aac tgg aat ggg gtt aca tgt gac ctc tct ggt cat gtg     240
Glu Cys Cys Asn Trp Asn Gly Val Thr Cys Asp Leu Ser Gly His Val
 65                  70                  75                  80 att gcc ttg gaa ctg gat gat gag aaa att tct agt gga att gag aat     288
Ile Ala Leu Glu Leu Asp Asp Glu Lys Ile Ser Ser Gly Ile Glu Asn
                 85                  90                  95 gca agt gct ctt ttc agt ctt cag tat ctt gag agg cta aat ttg gct     336
Ala Ser Ala Leu Phe Ser Leu Gln Tyr Leu Glu Arg Leu Asn Leu Ala
            100                 105                 110 tac aac aag ttc aat gtt ggc ata cca gtt ggt ata ggc aac ctc acc     384
Tyr Asn Lys Phe Asn Val Gly Ile Pro Val Gly Ile Gly Asn Leu Thr
        115                 120                 125
```

-continued

```
aac ttg acg tac ctg aat tta tcc aat gcc ggt ttt gtt ggc caa att     432
Asn Leu Thr Tyr Leu Asn Leu Ser Asn Ala Gly Phe Val Gly Gln Ile
        130                 135                 140 cct atg atg tta tca agg tta aca agg cta gtt act ctt gat ctc tca     480
Pro Met Met Leu Ser Arg Leu Thr Arg Leu Val Thr Leu Asp Leu Ser
145                 150                 155                 160 act ctt ttc cct gac ttt gcc cag cca cta aaa cta gag aat ccc aat     528
Thr Leu Phe Pro Asp Phe Ala Gln Pro Leu Lys Leu Glu Asn Pro Asn
                165                 170                 175 ttg agt cat ttc att gag aac tca aca gag ctt aga gag ctt tac ctt     576
Leu Ser His Phe Ile Glu Asn Ser Thr Glu Leu Arg Glu Leu Tyr Leu
        180                 185                 190 gat ggg gtt gat ctc tca gct cag agg act gag tgg tgt caa tct tta     624
Asp Gly Val Asp Leu Ser Ala Gln Arg Thr Glu Trp Cys Gln Ser Leu
195                 200                 205 tct tca tat ttg cct aac ttg act gtc ttg agc ttg cgt act tgt cga     672
Ser Ser Tyr Leu Pro Asn Leu Thr Val Leu Ser Leu Arg Thr Cys Arg
                210                 215                 220 att tca ggc cct att gat gaa tca ctt tct aag ctt cac ttt ctc tct     720
Ile Ser Gly Pro Ile Asp Glu Ser Leu Ser Lys Leu His Phe Leu Ser
225                 230                 235                 240 ttc atc cgt ctt gac cag aac aat ctc tct acc aca gtt cct gaa tac     768
Phe Ile Arg Leu Asp Gln Asn Asn Leu Ser Thr Thr Val Pro Glu Tyr
                245                 250                 255 ttt gcc aat ttc tca aac ttg act acc ttg acc ctc tcc tct tgt aat     816
Phe Ala Asn Phe Ser Asn Leu Thr Thr Leu Thr Leu Ser Ser Cys Asn
        260                 265                 270 ctg caa gga aca ttt cct aaa aga atc ttt cag gta cca gtc tta gag     864
Leu Gln Gly Thr Phe Pro Lys Arg Ile Phe Gln Val Pro Val Leu Glu
        275                 280                 285 ttt ttg gac ttg tca act aac aaa ttg ctt agt ggt agt att ccg att     912
Phe Leu Asp Leu Ser Thr Asn Lys Leu Leu Ser Gly Ser Ile Pro Ile
        290                 295                 300 ttt cct caa att gga tca ttg agg acg ata tca cta agc tac acc aag     960
Phe Pro Gln Ile Gly Ser Leu Arg Thr Ile Ser Leu Ser Tyr Thr Lys
305                 310                 315                 320 ttt tct ggt tca tta cca gac acc att tcg aac ctt caa aac cta tcc    1008
Phe Ser Gly Ser Leu Pro Asp Thr Ile Ser Asn Leu Gln Asn Leu Ser
                325                 330                 335 agg tta gaa ctc tcc aac tgc aat ttc agt gaa cca ata cct tcc aca    1056
Arg Leu Glu Leu Ser Asn Cys Asn Phe Ser Glu Pro Ile Pro Ser Thr
        340                 345                 350 atg gcg aac ctt acc aat ctt gtt tat tta gat ttc tcc ttc aac aat    1104
Met Ala Asn Leu Thr Asn Leu Val Tyr Leu Asp Phe Ser Phe Asn Asn
        355                 360                 365 ttc act ggt tcc ctc cca tat ttc caa ggg gcc aag aaa ctc atc tac    1152
Phe Thr Gly Ser Leu Pro Tyr Phe Gln Gly Ala Lys Lys Leu Ile Tyr
370                 375                 380 ttg gac ctt tca cgt aat ggt cta act ggt ctc ttg tct aga gct cat    1200
Leu Asp Leu Ser Arg Asn Gly Leu Thr Gly Leu Leu Ser Arg Ala His
385                 390                 395                 400 ttt gaa gga ctc tca gaa ctt gtc tac att aat tta ggg aac aat tca    1248
Phe Glu Gly Leu Ser Glu Leu Val Tyr Ile Asn Leu Gly Asn Asn Ser
                405                 410                 415 ctc aac ggg agc ctt cct gca tat ata ttt gag ctc ccc tcg ttg aag    1296
Leu Asn Gly Ser Leu Pro Ala Tyr Ile Phe Glu Leu Pro Ser Leu Lys
        420                 425                 430 cag ctt ttt ctt tac agc aat caa ttt gtt ggc caa gtc gac gaa ttt    1344
Gln Leu Phe Leu Tyr Ser Asn Gln Phe Val Gly Gln Val Asp Glu Phe
```

-continued

| | 435 | | | 440 | | | 445 | | | |
|---|---|---|---|---|---|---|---|---|---|---| cgc aat gca tcc tcc tct ccg ttg gat aca gtt gac ttg aga aac aac   1392
Arg Asn Ala Ser Ser Ser Pro Leu Asp Thr Val Asp Leu Arg Asn Asn
    450             455             460 cac ctg aat gga tcg att ccc aag tcc atg ttt gaa gtt ggg agg ctt   1440
His Leu Asn Gly Ser Ile Pro Lys Ser Met Phe Glu Val Gly Arg Leu
465             470             475             480 aag gtc ctc tca ctt tct tcc aac ttc ttt aga ggg aca gtt ccc ctt   1488
Lys Val Leu Ser Leu Ser Ser Asn Phe Phe Arg Gly Thr Val Pro Leu
                485             490             495 gac ctc att ggg agg ctg agc aac ctt tca aga ctg gag ctt tct tac   1536
Asp Leu Ile Gly Arg Leu Ser Asn Leu Ser Arg Leu Glu Leu Ser Tyr
            500             505             510 aat aac ttg act gtt gat gca agt agc agc aat tca acc tct ttc aca   1584
Asn Asn Leu Thr Val Asp Ala Ser Ser Ser Asn Ser Thr Ser Phe Thr
        515             520             525 ttt ccc cag ttg aac ata ttg aaa tta gcg tct tgt cgg ctg caa aag   1632
Phe Pro Gln Leu Asn Ile Leu Lys Leu Ala Ser Cys Arg Leu Gln Lys
    530             535             540 ttc ccc gat ctc aag aat cag tca agg atg atg cac tta gac ctt tca   1680
Phe Pro Asp Leu Lys Asn Gln Ser Arg Met Met His Leu Asp Leu Ser
545             550             555             560 gac aac caa ata ttg ggg gca ata cca aat tgg atc tgg gga att ggt   1728
Asp Asn Gln Ile Leu Gly Ala Ile Pro Asn Trp Ile Trp Gly Ile Gly
                565             570             575 ggt gga ggt ctc gcc cac ctg aat ctt tca ttc aat cag ctg gag tac   1776
Gly Gly Gly Leu Ala His Leu Asn Leu Ser Phe Asn Gln Leu Glu Tyr
            580             585             590 gtg gaa cag cct tac act gtt tcc agc aat ctt gca gtc ctt gat ttg   1824
Val Glu Gln Pro Tyr Thr Val Ser Ser Asn Leu Ala Val Leu Asp Leu
        595             600             605 cat tcc aac cgt tta aaa ggt gac tta cta ata cca cct tcc act gcc   1872
His Ser Asn Arg Leu Lys Gly Asp Leu Leu Ile Pro Pro Ser Thr Ala
    610             615             620 atc tat gtg gac tac tcg agc aat aat tta aac aat tcc atc cca aca   1920
Ile Tyr Val Asp Tyr Ser Ser Asn Asn Leu Asn Asn Ser Ile Pro Thr
625             630             635             640 gat att gga aga tct ctt ggt ttt gcc tcc ttt ttc tcg gta gca aac   1968
Asp Ile Gly Arg Ser Leu Gly Phe Ala Ser Phe Phe Ser Val Ala Asn
                645             650             655 aat agc atc act gga ata att cct gaa tcc ata tgc aac gtc agc tac   2016
Asn Ser Ile Thr Gly Ile Ile Pro Glu Ser Ile Cys Asn Val Ser Tyr
            660             665             670 ctt caa gtt ctt gat ttc tct aac aat gcc ttg agt gga aca ata cca   2064
Leu Gln Val Leu Asp Phe Ser Asn Asn Ala Leu Ser Gly Thr Ile Pro
        675             680             685 cca tgt cta ctg gaa tat agt cca aaa ctt gga gtg ctg aat cta ggg   2112
Pro Cys Leu Leu Glu Tyr Ser Pro Lys Leu Gly Val Leu Asn Leu Gly
    690             695             700 aac aat aga ctc cat ggt gtt ata cca gat tca ttt cca att ggt tgt   2160
Asn Asn Arg Leu His Gly Val Ile Pro Asp Ser Phe Pro Ile Gly Cys
705             710             715             720 gct cta ata act tta gac ctc agc agg aat atc ttt gaa ggg aag cta   2208
Ala Leu Ile Thr Leu Asp Leu Ser Arg Asn Ile Phe Glu Gly Lys Leu
                725             730             735 cca aaa tcg ctt gtc aac tgc acg ttg ttg gag gtc ctg aat gtt gga   2256
Pro Lys Ser Leu Val Asn Cys Thr Leu Leu Glu Val Leu Asn Val Gly
            740             745             750 aat aac agt ctt gtt gat cgt ttc cca tgc atg ttg agg aac tca acc   2304

-continued

```
                Asn Asn Ser Leu Val Asp Arg Phe Pro Cys Met Leu Arg Asn Ser Thr
                        755                 760                 765 agc ctg aag gtc cta gtc ttg cgc tcc aat aaa ttc aat gga aat ctt        2352
Ser Leu Lys Val Leu Val Leu Arg Ser Asn Lys Phe Asn Gly Asn Leu
    770                 775                 780 acg tgt aat ata acc aaa cat agc tgg aag aat ctc cag atc ata gat        2400
Thr Cys Asn Ile Thr Lys His Ser Trp Lys Asn Leu Gln Ile Ile Asp
785                 790                 795                 800 ata gct tcc aac aat ttt act ggt atg ttg aat gca gaa tgc ttt aca        2448
Ile Ala Ser Asn Asn Phe Thr Gly Met Leu Asn Ala Glu Cys Phe Thr
                805                 810                 815 aat tgg aga gga atg atg gtt gca aaa gat tac gtg gag aca gga cgc        2496
Asn Trp Arg Gly Met Met Val Ala Lys Asp Tyr Val Glu Thr Gly Arg
        820                 825                 830 aat cat atc cag tat gag ttc tta caa cta agt aac ttg tac tat cag        2544
Asn His Ile Gln Tyr Glu Phe Leu Gln Leu Ser Asn Leu Tyr Tyr Gln
            835                 840                 845 gat aca gtg aca tta atc atc aaa ggc atg gag ctg gag ctt gtg aag        2592
Asp Thr Val Thr Leu Ile Ile Lys Gly Met Glu Leu Glu Leu Val Lys
850                 855                 860 att ctt agg gtc ttc aca tct att gat ttc tct tcc aat aga ttt caa        2640
Ile Leu Arg Val Phe Thr Ser Ile Asp Phe Ser Ser Asn Arg Phe Gln
865                 870                 875                 880 gga aag ata cca gat act gtt ggg gat ctt agc tca ctt tat gtt ttg        2688
Gly Lys Ile Pro Asp Thr Val Gly Asp Leu Ser Ser Leu Tyr Val Leu
                885                 890                 895 aac ctg tca cac aat gcc ctc gag gga cca att cca aaa tca att ggg        2736
Asn Leu Ser His Asn Ala Leu Glu Gly Pro Ile Pro Lys Ser Ile Gly
        900                 905                 910 aag cta caa atg ctt gaa tca cta gac ctg tca aca aac cac ctg tcc        2784
Lys Leu Gln Met Leu Glu Ser Leu Asp Leu Ser Thr Asn His Leu Ser
            915                 920                 925 ggg gag atc ccc tca gag ctt tca agt ctc aca ttc tta gca gtt ttg        2832
Gly Glu Ile Pro Ser Glu Leu Ser Ser Leu Thr Phe Leu Ala Val Leu
930                 935                 940 aac tta tcg ttc aac aat ttg ttt gga aaa atc ccg caa agt aat caa        2880
Asn Leu Ser Phe Asn Asn Leu Phe Gly Lys Ile Pro Gln Ser Asn Gln
945                 950                 955                 960 ttt gaa aca ttc cca gca gaa tcc ttt gaa gga aac aga ggc cta tgc        2928
Phe Glu Thr Phe Pro Ala Glu Ser Phe Glu Gly Asn Arg Gly Leu Cys
                965                 970                 975 ggg ctt cct ctt aac gtc att tgc aaa agc gat act tca gag ttg aaa        2976
Gly Leu Pro Leu Asn Val Ile Cys Lys Ser Asp Thr Ser Glu Leu Lys
        980                 985                 990 cca gca cca agt tct caa gat gac tct tat gat tgg cag ttc ata ttt        3024
Pro Ala Pro Ser Ser Gln Asp Asp Ser Tyr Asp Trp Gln Phe Ile Phe
            995                 1000                1005 acg ggt gtg gga tat gga gta ggg gca gca atc tcc att gca cct ctg        3072
Thr Gly Val Gly Tyr Gly Val Gly Ala Ala Ile Ser Ile Ala Pro Leu
1010                1015                1020 ttg ttt tac aag caa gga aac aaa tac ttt gac aaa cat ttg gag aga        3120
Leu Phe Tyr Lys Gln Gly Asn Lys Tyr Phe Asp Lys His Leu Glu Arg
1025                1030                1035                1040 atg ctt aaa ctg atg ttt cct aga tac tgg ttc agt tac acc aga ttt        3168
Met Leu Lys Leu Met Phe Pro Arg Tyr Trp Phe Ser Tyr Thr Arg Phe
                1045                1050                1055 gac cct ggg aag gtt gtg gct gtg gaa cac tat gaa gat gag acc cca        3216
Asp Pro Gly Lys Val Val Ala Val Glu His Tyr Glu Asp Glu Thr Pro
        1060                1065                1070
```

| | | | | | | | | | | | | |
|---|---|---|---|---|---|---|---|---|---|---|---|---|
| gat | gac | acc | gaa | gat | gac | gat | gag | ggg | gga | aaa | gaa | gca | tct | ctt | ggg | 3264 |
| Asp | Asp | Thr | Glu | Asp | Asp | Asp | Glu | Gly | Gly | Lys | Glu | Ala | Ser | Leu | Gly | |
| | 1075 | | | | 1080 | | | | | 1085 | | | | | | |

```
gat gac acc gaa gat gac gat gag ggg gga aaa gaa gca tct ctt ggg    3264
Asp Asp Thr Glu Asp Asp Asp Glu Gly Gly Lys Glu Ala Ser Leu Gly
        1075                1080                1085 cgt tat tgt gtc ttc tgt agt aaa ctt gat ttt cag aaa aat gaa gca    3312
Arg Tyr Cys Val Phe Cys Ser Lys Leu Asp Phe Gln Lys Asn Glu Ala
    1090                1095                1100 atg cat gat cca aaa tgc act tgt cat atg tca tca tcc ccc aat tct   3360
Met His Asp Pro Lys Cys Thr Cys His Met Ser Ser Ser Pro Asn Ser
1105            1110                1115                1120 ttt cct cct acg ccg tcc tct tct tca cct tta tta gtc ata tat cac   3408
Phe Pro Pro Thr Pro Ser Ser Ser Ser Pro Leu Leu Val Ile Tyr His
                1125                1130                1135 aaa aag ttt tga                                                    3420
Lys Lys Phe
        1140

<210> SEQ ID NO 2
<211> LENGTH: 1139
<212> TYPE: PRT
<213> ORGANISM: Lycopersicon esculentum

<400> SEQUENCE: 2

Met Arg Phe Leu His Phe Leu Trp Ile Phe Phe Ile Ile Pro Phe Leu
 1                5                  10                  15

Gln Ile Leu Leu Gly Asn Glu Ile Leu Leu Val Ser Ser Gln Cys Leu
            20                  25                  30

Asp Asp Gln Lys Ser Leu Leu Leu Gln Leu Lys Gly Ser Phe Gln Tyr
        35                  40                  45

Asp Ser Thr Leu Ser Asn Lys Leu Ala Arg Trp Asn His Asn Thr Ser
    50                  55                  60

Glu Cys Cys Asn Trp Asn Gly Val Thr Cys Asp Leu Ser Gly His Val
65                  70                  75                  80

Ile Ala Leu Glu Leu Asp Asp Glu Lys Ile Ser Ser Gly Ile Glu Asn
                85                  90                  95

Ala Ser Ala Leu Phe Ser Leu Gln Tyr Leu Glu Arg Leu Asn Leu Ala
            100                 105                 110

Tyr Asn Lys Phe Asn Val Gly Ile Pro Val Gly Ile Gly Asn Leu Thr
        115                 120                 125

Asn Leu Thr Tyr Leu Asn Leu Ser Asn Ala Gly Phe Val Gly Gln Ile
    130                 135                 140

Pro Met Met Leu Ser Arg Leu Thr Arg Leu Val Thr Leu Asp Leu Ser
145                 150                 155                 160

Thr Leu Phe Pro Asp Phe Ala Gln Pro Leu Lys Leu Glu Asn Pro Asn
                165                 170                 175

Leu Ser His Phe Ile Glu Asn Ser Thr Glu Leu Arg Glu Leu Tyr Leu
            180                 185                 190

Asp Gly Val Asp Leu Ser Ala Gln Arg Thr Glu Trp Cys Gln Ser Leu
        195                 200                 205

Ser Ser Tyr Leu Pro Asn Leu Thr Val Leu Ser Leu Arg Thr Cys Arg
    210                 215                 220

Ile Ser Gly Pro Ile Asp Glu Ser Leu Ser Lys Leu His Phe Leu Ser
225                 230                 235                 240

Phe Ile Arg Leu Asp Gln Asn Asn Leu Ser Thr Thr Val Pro Glu Tyr
                245                 250                 255

Phe Ala Asn Phe Ser Asn Leu Thr Thr Leu Thr Leu Ser Ser Cys Asn
            260                 265                 270
```

```
Leu Gln Gly Thr Phe Pro Lys Arg Ile Phe Gln Val Pro Val Leu Glu
            275                 280                 285

Phe Leu Asp Leu Ser Thr Asn Lys Leu Leu Ser Gly Ser Ile Pro Ile
        290                 295                 300

Phe Pro Gln Ile Gly Ser Leu Arg Thr Ile Ser Leu Ser Tyr Thr Lys
305                 310                 315                 320

Phe Ser Gly Ser Leu Pro Asp Thr Ile Ser Asn Leu Gln Asn Leu Ser
                325                 330                 335

Arg Leu Glu Leu Ser Asn Cys Asn Phe Ser Glu Pro Ile Pro Ser Thr
            340                 345                 350

Met Ala Asn Leu Thr Asn Leu Val Tyr Leu Asp Phe Ser Phe Asn Asn
        355                 360                 365

Phe Thr Gly Ser Leu Pro Tyr Phe Gln Gly Ala Lys Lys Leu Ile Tyr
    370                 375                 380

Leu Asp Leu Ser Arg Asn Gly Leu Thr Gly Leu Leu Ser Arg Ala His
385                 390                 395                 400

Phe Glu Gly Leu Ser Glu Leu Val Tyr Ile Asn Leu Gly Asn Asn Ser
                405                 410                 415

Leu Asn Gly Ser Leu Pro Ala Tyr Ile Phe Glu Leu Pro Ser Leu Lys
            420                 425                 430

Gln Leu Phe Leu Tyr Ser Asn Gln Phe Val Gly Gln Val Asp Glu Phe
        435                 440                 445

Arg Asn Ala Ser Ser Ser Pro Leu Asp Thr Val Asp Leu Arg Asn Asn
    450                 455                 460

His Leu Asn Gly Ser Ile Pro Lys Ser Met Phe Glu Val Gly Arg Leu
465                 470                 475                 480

Lys Val Leu Ser Leu Ser Ser Asn Phe Phe Arg Gly Thr Val Pro Leu
                485                 490                 495

Asp Leu Ile Gly Arg Leu Ser Asn Leu Ser Arg Leu Glu Leu Ser Tyr
            500                 505                 510

Asn Asn Leu Thr Val Asp Ala Ser Ser Ser Asn Ser Thr Ser Phe Thr
        515                 520                 525

Phe Pro Gln Leu Asn Ile Leu Lys Leu Ala Ser Cys Arg Leu Gln Lys
    530                 535                 540

Phe Pro Asp Leu Lys Asn Gln Ser Arg Met Met His Leu Asp Leu Ser
545                 550                 555                 560

Asp Asn Gln Ile Leu Gly Ala Ile Pro Asn Trp Ile Trp Gly Ile Gly
                565                 570                 575

Gly Gly Gly Leu Ala His Leu Asn Leu Ser Phe Asn Gln Leu Glu Tyr
            580                 585                 590

Val Glu Gln Pro Tyr Thr Val Ser Ser Asn Leu Ala Val Leu Asp Leu
        595                 600                 605

His Ser Asn Arg Leu Lys Gly Asp Leu Leu Ile Pro Pro Ser Thr Ala
    610                 615                 620

Ile Tyr Val Asp Tyr Ser Ser Asn Asn Leu Asn Asn Ser Ile Pro Thr
625                 630                 635                 640

Asp Ile Gly Arg Ser Leu Gly Phe Ala Ser Phe Ser Val Ala Asn
                645                 650                 655

Asn Ser Ile Thr Gly Ile Ile Pro Glu Ser Ile Cys Asn Val Ser Tyr
            660                 665                 670

Leu Gln Val Leu Asp Phe Ser Asn Asn Ala Leu Ser Gly Thr Ile Pro
        675                 680                 685

Pro Cys Leu Leu Glu Tyr Ser Pro Lys Leu Gly Val Leu Asn Leu Gly
```

-continued

```
            690                 695                 700
Asn Asn Arg Leu His Gly Val Ile Pro Asp Ser Phe Pro Ile Gly Cys
705                 710                 715                 720
Ala Leu Ile Thr Leu Asp Leu Ser Arg Asn Ile Phe Glu Gly Lys Leu
                725                 730                 735
Pro Lys Ser Leu Val Asn Cys Thr Leu Leu Glu Val Leu Asn Val Gly
                740                 745                 750
Asn Asn Ser Leu Val Asp Arg Phe Pro Cys Met Leu Arg Asn Ser Thr
                755                 760                 765
Ser Leu Lys Val Leu Val Leu Arg Ser Asn Lys Phe Asn Gly Asn Leu
                770                 775                 780
Thr Cys Asn Ile Thr Lys His Ser Trp Lys Asn Leu Gln Ile Ile Asp
785                 790                 795                 800
Ile Ala Ser Asn Asn Phe Thr Gly Met Leu Asn Ala Glu Cys Phe Thr
                    805                 810                 815
Asn Trp Arg Gly Met Met Val Ala Lys Asp Tyr Val Glu Thr Gly Arg
                820                 825                 830
Asn His Ile Gln Tyr Glu Phe Leu Gln Leu Ser Asn Leu Tyr Tyr Gln
                835                 840                 845
Asp Thr Val Thr Leu Ile Ile Lys Gly Met Glu Leu Glu Leu Val Lys
850                 855                 860
Ile Leu Arg Val Phe Thr Ser Ile Asp Phe Ser Ser Asn Arg Phe Gln
865                 870                 875                 880
Gly Lys Ile Pro Asp Thr Val Gly Asp Leu Ser Ser Leu Tyr Val Leu
                885                 890                 895
Asn Leu Ser His Asn Ala Leu Glu Gly Pro Ile Pro Lys Ser Ile Gly
                900                 905                 910
Lys Leu Gln Met Leu Glu Ser Leu Asp Leu Ser Thr Asn His Leu Ser
                915                 920                 925
Gly Glu Ile Pro Ser Glu Leu Ser Leu Thr Phe Leu Ala Val Leu
                930                 935                 940
Asn Leu Ser Phe Asn Asn Leu Phe Gly Lys Ile Pro Gln Ser Asn Gln
945                 950                 955                 960
Phe Glu Thr Phe Pro Ala Glu Ser Phe Glu Gly Asn Arg Gly Leu Cys
                965                 970                 975
Gly Leu Pro Leu Asn Val Ile Cys Lys Ser Asp Thr Ser Glu Leu Lys
                980                 985                 990
Pro Ala Pro Ser Ser Gln Asp Ser Tyr Asp Trp Gln Phe Ile Phe
                995                 1000                1005
Thr Gly Val Gly Tyr Gly Val Gly Ala Ala Ile Ser Ile Ala Pro Leu
    1010                1015                1020
Leu Phe Tyr Lys Gln Gly Asn Lys Tyr Phe Asp Lys His Leu Glu Arg
1025                1030                1035                1040
Met Leu Lys Leu Met Phe Pro Arg Tyr Trp Phe Ser Tyr Thr Arg Phe
                1045                1050                1055
Asp Pro Gly Lys Val Val Ala Val Glu His Tyr Glu Asp Glu Thr Pro
                1060                1065                1070
Asp Asp Thr Glu Asp Asp Asp Glu Gly Gly Lys Glu Ala Ser Leu Gly
                1075                1080                1085
Arg Tyr Cys Val Phe Cys Ser Lys Leu Asp Phe Gln Lys Asn Glu Ala
                1090                1095                1100
Met His Asp Pro Lys Cys Thr Cys His Met Ser Ser Ser Pro Asn Ser
1105                1110                1115                1120
```

```
Phe Pro Pro Thr Pro Ser Ser Ser Pro Leu Leu Val Ile Tyr His
             1125                1130                1135

Lys Lys Phe

<210> SEQ ID NO 3
<211> LENGTH: 3478
<212> TYPE: DNA
<213> ORGANISM: Lycopersicon esculentum
<220> FEATURE:
<221> NAME/KEY: misc_feature
<222> LOCATION: (1)..(3478)
<223> OTHER INFORMATION: Ve1.1 cDNA sequence
<220> FEATURE:
<221> NAME/KEY: CDS
<222> LOCATION: (57)..(3476)

<400> SEQUENCE: 3
gcacgagaga aaaacaaca agtttgatgg attataattc ctccaagact taagca atg      59
                                                              Met
                                                                1 aga ttt tta cac ttt cta tgg atc ttc ttc atc ata ccc ttt ttg caa     107
Arg Phe Leu His Phe Leu Trp Ile Phe Phe Ile Ile Pro Phe Leu Gln
         5                  10                  15 att tta tta ggt aat gag att tta ttg gtt tcc tct caa tgt ctt gat     155
Ile Leu Leu Gly Asn Glu Ile Leu Leu Val Ser Ser Gln Cys Leu Asp
     20                  25                  30 gat caa aag tca ttg ttg ctg cag ttg aag ggc agc ttc caa tat gat     203
Asp Gln Lys Ser Leu Leu Leu Gln Leu Lys Gly Ser Phe Gln Tyr Asp
 35                  40                  45 tct act ttg tca aat aaa ttg gca aga tgg aac cac aac aca agt gaa     251
Ser Thr Leu Ser Asn Lys Leu Ala Arg Trp Asn His Asn Thr Ser Glu
 50                  55                  60                  65 tgt tgt aac tgg aat ggg gtt aca tgt gac ctc tct ggt cat gtg att     299
Cys Cys Asn Trp Asn Gly Val Thr Cys Asp Leu Ser Gly His Val Ile
                 70                  75                  80 gcc ttg gaa ctg gat gat gag aaa att tct agt gga att gag aat gca     347
Ala Leu Glu Leu Asp Asp Glu Lys Ile Ser Ser Gly Ile Glu Asn Ala
             85                  90                  95 agt gct ctt ttc agt ctt cag tat ctt gag agg cta aat ttg gct tac     395
Ser Ala Leu Phe Ser Leu Gln Tyr Leu Glu Arg Leu Asn Leu Ala Tyr
        100                 105                 110 aac aag ttc aat gtt ggc ata cca gtt ggt ata ggc aac ctc acc aac     443
Asn Lys Phe Asn Val Gly Ile Pro Val Gly Ile Gly Asn Leu Thr Asn
    115                 120                 125 ttg acg tac ctg aat tta tcc aat gcc ggt ttt gtt ggc caa att cct     491
Leu Thr Tyr Leu Asn Leu Ser Asn Ala Gly Phe Val Gly Gln Ile Pro
130                 135                 140                 145 atg atg tta tca agg tta aca agg cta gtt act ctt gat ctc tca act     539
Met Met Leu Ser Arg Leu Thr Arg Leu Val Thr Leu Asp Leu Ser Thr
                150                 155                 160 ctt ttc cct gac ttt gcc cag cca cta aaa cta gag aat ccc aat ttg     587
Leu Phe Pro Asp Phe Ala Gln Pro Leu Lys Leu Glu Asn Pro Asn Leu
            165                 170                 175 agt cat ttc att gag aac tca aca gag ctt aga gag ctt tac ctt gat     635
Ser His Phe Ile Glu Asn Ser Thr Glu Leu Arg Glu Leu Tyr Leu Asp
        180                 185                 190 ggg gtt gat ctc tca gct cag agg act gag tgg tgt caa tct tta tct     683
Gly Val Asp Leu Ser Ala Gln Arg Thr Glu Trp Cys Gln Ser Leu Ser
    195                 200                 205 tca tat ttg cct aac ttg act gtc ttg agc ttg cgt act tgt cga att     731
Ser Tyr Leu Pro Asn Leu Thr Val Leu Ser Leu Arg Thr Cys Arg Ile
```

```
210                 215                 220                 225 tca ggc cct att gat gaa tca ctt tct aag ctt cac ttt ctc tct ttc      779
Ser Gly Pro Ile Asp Glu Ser Leu Ser Lys Leu His Phe Leu Ser Phe
                230                 235                 240 atc cgt ctt gac cag aac aat ctc tct acc aca gtt cct gaa tac ttt      827
Ile Arg Leu Asp Gln Asn Asn Leu Ser Thr Thr Val Pro Glu Tyr Phe
                245                 250                 255 gcc aat ttc tca aac ttg act acc ttg acc ctc tcc tct tgt aat ctg      875
Ala Asn Phe Ser Asn Leu Thr Thr Leu Thr Leu Ser Ser Cys Asn Leu
                260                 265                 270 caa gga aca ttt cct aaa aga atc ttt cag gta cca gtc tta gag ttt      923
Gln Gly Thr Phe Pro Lys Arg Ile Phe Gln Val Pro Val Leu Glu Phe
                275                 280                 285 ttg gac ttg tca act aac aaa ttg ctt agt ggt agt att ccg att ttt      971
Leu Asp Leu Ser Thr Asn Lys Leu Leu Ser Gly Ser Ile Pro Ile Phe
290                 295                 300                 305 cct caa att gga tca ttg agg acg ata tca cta agc tac acc aag ttt     1019
Pro Gln Ile Gly Ser Leu Arg Thr Ile Ser Leu Ser Tyr Thr Lys Phe
                310                 315                 320 tct ggt tca tta cca gac acc att tcg aac ctt caa aac cta tcc agg     1067
Ser Gly Ser Leu Pro Asp Thr Ile Ser Asn Leu Gln Asn Leu Ser Arg
                325                 330                 335 tta gaa ctc tcc aac tgc aat ttc agt gaa cca ata cct tcc aca atg     1115
Leu Glu Leu Ser Asn Cys Asn Phe Ser Glu Pro Ile Pro Ser Thr Met
                340                 345                 350 gcg aac ctt acc aat ctt gtt tat tta gat ttc tcc ttc aac aat ttc     1163
Ala Asn Leu Thr Asn Leu Val Tyr Leu Asp Phe Ser Phe Asn Asn Phe
                355                 360                 365 act ggt tcc ctc cca tat ttc caa ggg gcc aag aaa ctc atc tac ttg     1211
Thr Gly Ser Leu Pro Tyr Phe Gln Gly Ala Lys Lys Leu Ile Tyr Leu
370                 375                 380                 385 gac ctt tca cgt aat ggt cta act ggt ctc ttg tct aga gct cat ttt     1259
Asp Leu Ser Arg Asn Gly Leu Thr Gly Leu Leu Ser Arg Ala His Phe
                390                 395                 400 gaa gga ctc tca gaa ctt gtc tac att aat tta ggg aac aat tca ctc     1307
Glu Gly Leu Ser Glu Leu Val Tyr Ile Asn Leu Gly Asn Asn Ser Leu
                405                 410                 415 aac ggg agc ctt cct gca tat ata ttt gag ctc ccc tcg ttg aag cag     1355
Asn Gly Ser Leu Pro Ala Tyr Ile Phe Glu Leu Pro Ser Leu Lys Gln
                420                 425                 430 ctt ttt ctt tac agc aat caa ttt gtt ggc caa gtc gac gaa ttt cgc     1403
Leu Phe Leu Tyr Ser Asn Gln Phe Val Gly Gln Val Asp Glu Phe Arg
            435                 440                 445 aat gca tcc tcc tct ccg ttg gat aca gtt gac ttg aga aac aac cac     1451
Asn Ala Ser Ser Ser Pro Leu Asp Thr Val Asp Leu Arg Asn Asn His
450                 455                 460                 465 ctg aat gga tcg att ccc aag tcc atg ttt gaa gtt ggg agg ctt aag     1499
Leu Asn Gly Ser Ile Pro Lys Ser Met Phe Glu Val Gly Arg Leu Lys
                470                 475                 480 gtc ctc tca ctt tct tcc aac ttc ttt aga ggg aca gtt ccc ctt gac     1547
Val Leu Ser Leu Ser Ser Asn Phe Phe Arg Gly Thr Val Pro Leu Asp
            485                 490                 495 ctc att ggg agg ctg agc aac ctt tca aga ctg gag ctt tct tac aat     1595
Leu Ile Gly Arg Leu Ser Asn Leu Ser Arg Leu Glu Leu Ser Tyr Asn
            500                 505                 510 aac ttg act gtt gat gca agt agc agc aat tca acc tct ttc aca ttt     1643
Asn Leu Thr Val Asp Ala Ser Ser Ser Asn Ser Thr Ser Phe Thr Phe
            515                 520                 525 ccc cag ttg aac ata ttg aaa tta gcg tct tgt cgg ctg caa aag ttc     1691
```

-continued

```
Pro Gln Leu Asn Ile Leu Lys Leu Ala Ser Cys Arg Leu Gln Lys Phe
530                 535                 540                 545 ccc gat ctc aag aat cag tca agg atg atg cac tta gac ctt tca gac      1739
Pro Asp Leu Lys Asn Gln Ser Arg Met Met His Leu Asp Leu Ser Asp
                550                 555                 560 aac caa ata ttg ggg gca ata cca aat tgg atc tgg gga att ggt ggt      1787
Asn Gln Ile Leu Gly Ala Ile Pro Asn Trp Ile Trp Gly Ile Gly Gly
        565                 570                 575 gga ggt ctc gcc cac ctg aat ctt tca ttc aat cag ctg gag tac gtg      1835
Gly Gly Leu Ala His Leu Asn Leu Ser Phe Asn Gln Leu Glu Tyr Val
580                 585                 590 gaa cag cct tac act gtt tcc agc aat ctt gta gtc ctt gat ttg cat      1883
Glu Gln Pro Tyr Thr Val Ser Ser Asn Leu Val Val Leu Asp Leu His
    595                 600                 605 tcc aac cgt tta aaa ggt gac tta cta ata cca cct tcc act gcc atc      1931
Ser Asn Arg Leu Lys Gly Asp Leu Leu Ile Pro Pro Ser Thr Ala Ile
610                 615                 620                 625 tat gtg gac tac tcg agc aat aat tta aac aat tcc atc cca aca gat      1979
Tyr Val Asp Tyr Ser Ser Asn Asn Leu Asn Asn Ser Ile Pro Thr Asp
                630                 635                 640 att gga aga tct ctt ggt ttt gcc tcc ttt ttc tcg gta gca aac aat      2027
Ile Gly Arg Ser Leu Gly Phe Ala Ser Phe Phe Ser Val Ala Asn Asn
        645                 650                 655 agc atc act gga ata att cct gaa tcc ata tgc aac gtc agc tac ctt      2075
Ser Ile Thr Gly Ile Ile Pro Glu Ser Ile Cys Asn Val Ser Tyr Leu
660                 665                 670 caa gtt ctt gat ttc tct aac aat gcc ttg agt gga aca ata cca cca      2123
Gln Val Leu Asp Phe Ser Asn Asn Ala Leu Ser Gly Thr Ile Pro Pro
    675                 680                 685 tgt cta ctg gaa tat agt cca aaa ctt gga gtg ctg aat cta ggg aac      2171
Cys Leu Leu Glu Tyr Ser Pro Lys Leu Gly Val Leu Asn Leu Gly Asn
690                 695                 700                 705 aat aga ctc cat ggt gtt ata cca gat tca ttt cca att ggt tgt gct      2219
Asn Arg Leu His Gly Val Ile Pro Asp Ser Phe Pro Ile Gly Cys Ala
                710                 715                 720 cta ata act tta gac ctc agc agg aat atc ttt gaa ggg aag cta cca      2267
Leu Ile Thr Leu Asp Leu Ser Arg Asn Ile Phe Glu Gly Lys Leu Pro
        725                 730                 735 aaa tcg ctt gtc aac tgc acg ttg ttg gag gtc ctg aat gtt gga aat      2315
Lys Ser Leu Val Asn Cys Thr Leu Leu Glu Val Leu Asn Val Gly Asn
740                 745                 750 aac agt ctt gtt gat cgt ttc cca tgc atg ttg agg aac tca acc agc      2363
Asn Ser Leu Val Asp Arg Phe Pro Cys Met Leu Arg Asn Ser Thr Ser
    755                 760                 765 ctg aag gtc cta gtc ttg cgc tcc aat aaa ttc aat gga aat ctt acg      2411
Leu Lys Val Leu Val Leu Arg Ser Asn Lys Phe Asn Gly Asn Leu Thr
770                 775                 780                 785 tgt aat ata acc aaa cat agc tgg aag aat ctc cag atc ata gat ata      2459
Cys Asn Ile Thr Lys His Ser Trp Lys Asn Leu Gln Ile Ile Asp Ile
                790                 795                 800 gct tcc aac aat ttt act ggt atg ttg aat gca gaa tgc ttt aca aat      2507
Ala Ser Asn Asn Phe Thr Gly Met Leu Asn Ala Glu Cys Phe Thr Asn
        805                 810                 815 tgg aga gga atg atg gtt gca aaa gat tac gtg gag aca gga cgc aat      2555
Trp Arg Gly Met Met Val Ala Lys Asp Tyr Val Glu Thr Gly Arg Asn
820                 825                 830 cat atc cag tat gag ttc tta caa cta agt aac ttg tac tat cag gat      2603
His Ile Gln Tyr Glu Phe Leu Gln Leu Ser Asn Leu Tyr Tyr Gln Asp
    835                 840                 845
```

```
aca gtg aca tta atc atc aaa ggc atg gag ctg gag ctt gtg aag att     2651
Thr Val Thr Leu Ile Ile Lys Gly Met Glu Leu Glu Leu Val Lys Ile
850                 855                 860                 865 ctt agg gtc ttc aca tct att gat ttc tct tcc aat aga ttt caa gga     2699
Leu Arg Val Phe Thr Ser Ile Asp Phe Ser Ser Asn Arg Phe Gln Gly
                870                 875                 880 aag ata cca gat act gtt ggg gat ctt agc tca ctt tat gtt ttg aac     2747
Lys Ile Pro Asp Thr Val Gly Asp Leu Ser Ser Leu Tyr Val Leu Asn
            885                 890                 895 ctg tca cac aat gcc ctc gag gga cca att cca aaa tca att ggg aag     2795
Leu Ser His Asn Ala Leu Glu Gly Pro Ile Pro Lys Ser Ile Gly Lys
        900                 905                 910 cta caa atg ctt gaa tca cta gac ctg tca aga aac cac ctg tcc ggg     2843
Leu Gln Met Leu Glu Ser Leu Asp Leu Ser Arg Asn His Leu Ser Gly
    915                 920                 925 gag atc ccc tca gag ctt tca agt ctc aca ttc tta gca gtt ttg aac     2891
Glu Ile Pro Ser Glu Leu Ser Ser Leu Thr Phe Leu Ala Val Leu Asn
930                 935                 940                 945 tta tcg ttc aac aat ttg ttt gga aaa atc ccg caa agt aat caa ttt     2939
Leu Ser Phe Asn Asn Leu Phe Gly Lys Ile Pro Gln Ser Asn Gln Phe
                950                 955                 960 gaa aca ttc tca gca gaa tcc ttt gaa gga aac aga ggc cta tgc ggg     2987
Glu Thr Phe Ser Ala Glu Ser Phe Glu Gly Asn Arg Gly Leu Cys Gly
            965                 970                 975 ctc cct ctt aac gtc att tgc aaa agc gat act tca gag ttg aaa cca     3035
Leu Pro Leu Asn Val Ile Cys Lys Ser Asp Thr Ser Glu Leu Lys Pro
        980                 985                 990 gca cca agt tct caa gat gac tct tat gat tgg cag ttc ata ttt acg     3083
Ala Pro Ser Ser Gln Asp Asp Ser Tyr Asp Trp Gln Phe Ile Phe Thr
    995                 1000                1005 ggt gtg gga tat gga gta ggg gca gca atc tcc att gca cct ctg ttg     3131
Gly Val Gly Tyr Gly Val Gly Ala Ala Ile Ser Ile Ala Pro Leu Leu
1010                1015                1020                1025 ttt tac aag caa gga aac aaa tac ttt gac aaa cat ttg gag aga atg     3179
Phe Tyr Lys Gln Gly Asn Lys Tyr Phe Asp Lys His Leu Glu Arg Met
                1030                1035                1040 ctt aaa ctg atg ttt cct aga tac tgg ttc agt tac acc aga ttt gac     3227
Leu Lys Leu Met Phe Pro Arg Tyr Trp Phe Ser Tyr Thr Arg Phe Asp
            1045                1050                1055 cct ggg aag gtt gtg gct gtg gaa cac tat gaa gat gag acc cca gat     3275
Pro Gly Lys Val Val Ala Val Glu His Tyr Glu Asp Glu Thr Pro Asp
        1060                1065                1070 gac acc gaa gat gac gat gag ggt gga aaa gaa gca tct ctt ggg cgt     3323
Asp Thr Glu Asp Asp Asp Glu Gly Gly Lys Glu Ala Ser Leu Gly Arg
    1075                1080                1085 tat tgt gtc ttc tgt agt aaa ctt gat ttt cag aaa aat gaa gca atg     3371
Tyr Cys Val Phe Cys Ser Lys Leu Asp Phe Gln Lys Asn Glu Ala Met
1090                1095                1100                1105 cat gat cca aaa tgc act tgt cat atg tca tca tcc ccc aat tct ttt     3419
His Asp Pro Lys Cys Thr Cys His Met Ser Ser Ser Pro Asn Ser Phe
                1110                1115                1120 cct cct acg ccg tcc ttt ttt tca cct tta tta gtc ata tat cac aaa     3467
Pro Pro Thr Pro Ser Phe Phe Ser Pro Leu Leu Val Ile Tyr His Lys
            1125                1130                1135 aag ttt tga tt                                                      3478
Lys Phe
    1140

<210> SEQ ID NO 4
<211> LENGTH: 1139
```

```
<212> TYPE: PRT
<213> ORGANISM: Lycopersicon esculentum

<400> SEQUENCE: 4

Met Arg Phe Leu His Phe Leu Trp Ile Phe Ile Ile Pro Phe Leu
 1               5                  10                  15

Gln Ile Leu Leu Gly Asn Glu Ile Leu Leu Val Ser Ser Gln Cys Leu
                20                  25                  30

Asp Asp Gln Lys Ser Leu Leu Gln Leu Lys Gly Ser Phe Gln Tyr
            35                  40                  45

Asp Ser Thr Leu Ser Asn Lys Leu Ala Arg Trp Asn His Asn Thr Ser
        50                  55                  60

Glu Cys Cys Asn Trp Asn Gly Val Thr Cys Asp Leu Ser Gly His Val
 65                 70                  75                  80

Ile Ala Leu Glu Leu Asp Asp Glu Lys Ile Ser Ser Gly Ile Glu Asn
                85                  90                  95

Ala Ser Ala Leu Phe Ser Leu Gln Tyr Leu Glu Arg Leu Asn Leu Ala
                100                 105                 110

Tyr Asn Lys Phe Asn Val Gly Ile Pro Val Gly Ile Gly Asn Leu Thr
            115                 120                 125

Asn Leu Thr Tyr Leu Asn Leu Ser Asn Ala Gly Phe Val Gly Gln Ile
    130                 135                 140

Pro Met Met Leu Ser Arg Leu Thr Arg Leu Val Thr Leu Asp Leu Ser
145                 150                 155                 160

Thr Leu Phe Pro Asp Phe Ala Gln Pro Leu Lys Leu Glu Asn Pro Asn
                165                 170                 175

Leu Ser His Phe Ile Glu Asn Ser Thr Glu Leu Arg Glu Leu Tyr Leu
                180                 185                 190

Asp Gly Val Asp Leu Ser Ala Gln Arg Thr Glu Trp Cys Gln Ser Leu
            195                 200                 205

Ser Ser Tyr Leu Pro Asn Leu Thr Val Leu Ser Leu Arg Thr Cys Arg
    210                 215                 220

Ile Ser Gly Pro Ile Asp Glu Ser Leu Ser Lys Leu His Phe Leu Ser
225                 230                 235                 240

Phe Ile Arg Leu Asp Gln Asn Asn Leu Ser Thr Thr Val Pro Glu Tyr
                245                 250                 255

Phe Ala Asn Phe Ser Asn Leu Thr Thr Leu Thr Leu Ser Ser Cys Asn
                260                 265                 270

Leu Gln Gly Thr Phe Pro Lys Arg Ile Phe Gln Val Pro Val Leu Glu
            275                 280                 285

Phe Leu Asp Leu Ser Thr Asn Lys Leu Leu Ser Gly Ser Ile Pro Ile
    290                 295                 300

Phe Pro Gln Ile Gly Ser Leu Arg Thr Ile Ser Leu Ser Tyr Thr Lys
305                 310                 315                 320

Phe Ser Gly Ser Leu Pro Asp Thr Ile Ser Asn Leu Gln Asn Leu Ser
                325                 330                 335

Arg Leu Glu Leu Ser Asn Cys Asn Phe Ser Glu Pro Ile Pro Ser Thr
            340                 345                 350

Met Ala Asn Leu Thr Asn Leu Val Tyr Leu Asp Phe Ser Phe Asn Asn
    355                 360                 365

Phe Thr Gly Ser Leu Pro Tyr Phe Gln Gly Ala Lys Lys Leu Ile Tyr
            370                 375                 380

Leu Asp Leu Ser Arg Asn Gly Leu Thr Gly Leu Leu Ser Arg Ala His
385                 390                 395                 400
```

-continued

```
Phe Glu Gly Leu Ser Glu Leu Val Tyr Ile Asn Leu Gly Asn Asn Ser
                405                 410                 415
Leu Asn Gly Ser Leu Pro Ala Tyr Ile Phe Glu Leu Pro Ser Leu Lys
            420                 425                 430
Gln Leu Phe Leu Tyr Ser Asn Gln Phe Val Gly Gln Val Asp Glu Phe
        435                 440                 445
Arg Asn Ala Ser Ser Ser Pro Leu Asp Thr Val Asp Leu Arg Asn Asn
    450                 455                 460
His Leu Asn Gly Ser Ile Pro Lys Ser Met Phe Glu Val Gly Arg Leu
465                 470                 475                 480
Lys Val Leu Ser Leu Ser Ser Asn Phe Phe Arg Gly Thr Val Pro Leu
                485                 490                 495
Asp Leu Ile Gly Arg Leu Ser Asn Leu Ser Arg Leu Glu Leu Ser Tyr
            500                 505                 510
Asn Asn Leu Thr Val Asp Ala Ser Ser Asn Ser Thr Ser Phe Thr
        515                 520                 525
Phe Pro Gln Leu Asn Ile Leu Lys Leu Ala Ser Cys Arg Leu Gln Lys
    530                 535                 540
Phe Pro Asp Leu Lys Asn Gln Ser Arg Met Met His Leu Asp Leu Ser
545                 550                 555                 560
Asp Asn Gln Ile Leu Gly Ala Ile Pro Asn Trp Ile Trp Gly Ile Gly
                565                 570                 575
Gly Gly Gly Leu Ala His Leu Asn Leu Ser Phe Asn Gln Leu Glu Tyr
            580                 585                 590
Val Glu Gln Pro Tyr Thr Val Ser Ser Asn Leu Val Val Leu Asp Leu
        595                 600                 605
His Ser Asn Arg Leu Lys Gly Asp Leu Leu Ile Pro Pro Ser Thr Ala
    610                 615                 620
Ile Tyr Val Asp Tyr Ser Ser Asn Leu Asn Asn Ser Ile Pro Thr
625                 630                 635                 640
Asp Ile Gly Arg Ser Leu Gly Phe Ala Ser Phe Phe Ser Val Ala Asn
                645                 650                 655
Asn Ser Ile Thr Gly Ile Ile Pro Glu Ser Ile Cys Asn Val Ser Tyr
            660                 665                 670
Leu Gln Val Leu Asp Phe Ser Asn Asn Ala Leu Ser Gly Thr Ile Pro
        675                 680                 685
Pro Cys Leu Leu Glu Tyr Ser Pro Lys Leu Gly Val Leu Asn Leu Gly
    690                 695                 700
Asn Asn Arg Leu His Gly Val Ile Pro Asp Ser Phe Pro Ile Gly Cys
705                 710                 715                 720
Ala Leu Ile Thr Leu Asp Leu Ser Arg Asn Ile Phe Glu Gly Lys Leu
                725                 730                 735
Pro Lys Ser Leu Val Asn Cys Thr Leu Leu Glu Val Leu Asn Val Gly
            740                 745                 750
Asn Asn Ser Leu Val Asp Arg Phe Pro Cys Met Leu Arg Asn Ser Thr
        755                 760                 765
Ser Leu Lys Val Leu Val Leu Arg Ser Asn Lys Phe Asn Gly Asn Leu
    770                 775                 780
Thr Cys Asn Ile Thr Lys His Ser Trp Lys Asn Leu Gln Ile Ile Asp
785                 790                 795                 800
Ile Ala Ser Asn Asn Phe Thr Gly Met Leu Asn Ala Glu Cys Phe Thr
                805                 810                 815
```

```
Asn Trp Arg Gly Met Met Val Ala Lys Asp Tyr Val Glu Thr Gly Arg
            820                 825                 830

Asn His Ile Gln Tyr Glu Phe Leu Gln Leu Ser Asn Leu Tyr Tyr Gln
        835                 840                 845

Asp Thr Val Thr Leu Ile Ile Lys Gly Met Glu Leu Glu Leu Val Lys
    850                 855                 860

Ile Leu Arg Val Phe Thr Ser Ile Asp Phe Ser Ser Asn Arg Phe Gln
865                 870                 875                 880

Gly Lys Ile Pro Asp Thr Val Gly Asp Leu Ser Ser Leu Tyr Val Leu
                885                 890                 895

Asn Leu Ser His Asn Ala Leu Glu Gly Pro Ile Pro Lys Ser Ile Gly
            900                 905                 910

Lys Leu Gln Met Leu Glu Ser Leu Asp Leu Ser Arg Asn His Leu Ser
        915                 920                 925

Gly Glu Ile Pro Ser Glu Leu Ser Ser Leu Thr Phe Leu Ala Val Leu
    930                 935                 940

Asn Leu Ser Phe Asn Asn Leu Phe Gly Lys Ile Pro Gln Ser Asn Gln
945                 950                 955                 960

Phe Glu Thr Phe Ser Ala Glu Ser Phe Glu Gly Asn Arg Gly Leu Cys
                965                 970                 975

Gly Leu Pro Leu Asn Val Ile Cys Lys Ser Asp Thr Ser Glu Leu Lys
            980                 985                 990

Pro Ala Pro Ser Ser Gln Asp Asp Ser Tyr Asp Trp Gln Phe Ile Phe
        995                 1000                1005

Thr Gly Val Gly Tyr Gly Val Gly Ala Ala Ile Ser Ile Ala Pro Leu
    1010                1015                1020

Leu Phe Tyr Lys Gln Gly Asn Lys Tyr Phe Asp Lys His Leu Glu Arg
1025                1030                1035                1040

Met Leu Lys Leu Met Phe Pro Arg Tyr Trp Phe Ser Tyr Thr Arg Phe
                1045                1050                1055

Asp Pro Gly Lys Val Val Ala Val Glu His Tyr Glu Asp Glu Thr Pro
            1060                1065                1070

Asp Asp Thr Glu Asp Asp Glu Gly Gly Lys Glu Ala Ser Leu Gly
        1075                1080                1085

Arg Tyr Cys Val Phe Cys Ser Leu Asp Phe Gln Lys Asn Glu Ala
    1090                1095                1100

Met His Asp Pro Lys Cys Thr Cys His Met Ser Ser Ser Pro Asn Ser
1105                1110                1115                1120

Phe Pro Pro Thr Pro Ser Phe Phe Ser Pro Leu Leu Val Ile Tyr His
                1125                1130                1135

Lys Lys Phe

<210> SEQ ID NO 5
<211> LENGTH: 3162
<212> TYPE: DNA
<213> ORGANISM: Lycopersicon esculentum
<220> FEATURE:
<221> NAME/KEY: misc_feature
<222> LOCATION: (1)..(3162)
<223> OTHER INFORMATION: Ve1.2 genomic DNA sequence
<220> FEATURE:
<221> NAME/KEY: CDS
<222> LOCATION: (1)..(3162)

<400> SEQUENCE: 5 atg aaa atg atg gca act ctg tac ttc cct atg gtt ctc ttg att ccc      48
Met Lys Met Met Ala Thr Leu Tyr Phe Pro Met Val Leu Leu Ile Pro
```

```
        1                   5                      10                       15
      tcg   ttt   caa   atc   tta   tca   gga   tac   cac   att   ttc   ttg   gtt   tcc   tct   caa        96
      Ser   Phe   Gln   Ile   Leu   Ser   Gly   Tyr   His   Ile   Phe   Leu   Val   Ser   Ser   Gln
                                    20                      25                      30 tgc   ctt   gac   gat   caa   aag   tca   ttg   ttg   ctg   cag   ttt   aag   gga   agc   ctc       144
      Cys   Leu   Asp   Asp   Gln   Lys   Ser   Leu   Leu   Leu   Gln   Phe   Lys   Gly   Ser   Leu
                        35                      40                      45 caa   tat   gat   tct   act   ttg   tca   aag   aaa   ttg   gca   aaa   tgg   aac   gac   atg       192
      Gln   Tyr   Asp   Ser   Thr   Leu   Ser   Lys   Lys   Leu   Ala   Lys   Trp   Asn   Asp   Met
            50                            55                      60 aca   agt   gaa   tgt   tgc   aat   tgg   aat   ggg   gtt   aca   tgc   aat   ctc   ttt   ggt       240
      Thr   Ser   Glu   Cys   Cys   Asn   Trp   Asn   Gly   Val   Thr   Cys   Asn   Leu   Phe   Gly
      65                      70                      75                            80 cat   gtg   atc   gct   ttg   gaa   ctg   gat   gat   gag   act   att   tct   agt   gga   att       288
      His   Val   Ile   Ala   Leu   Glu   Leu   Asp   Asp   Glu   Thr   Ile   Ser   Ser   Gly   Ile
                              85                      90                      95 gag   aat   tct   agt   gca   ctt   ttc   agt   ctt   caa   tat   ctt   gag   agc   cta   aat       336
      Glu   Asn   Ser   Ser   Ala   Leu   Phe   Ser   Leu   Gln   Tyr   Leu   Glu   Ser   Leu   Asn
                              100                     105                     110 ttg   gct   gac   aac   atg   ttc   aat   gtt   ggc   ata   cca   gtt   ggt   ata   gac   aac       384
      Leu   Ala   Asp   Asn   Met   Phe   Asn   Val   Gly   Ile   Pro   Val   Gly   Ile   Asp   Asn
                        115                     120                     125 ctc   aca   aac   ttg   aag   tac   ctg   aat   tta   tcc   aat   gct   ggt   ttt   gtc   ggg       432
      Leu   Thr   Asn   Leu   Lys   Tyr   Leu   Asn   Leu   Ser   Asn   Ala   Gly   Phe   Val   Gly
            130                     135                     140 caa   att   cct   ata   aca   tta   tca   aga   tta   aca   agg   cta   gtt   act   ctt   gat       480
      Gln   Ile   Pro   Ile   Thr   Leu   Ser   Arg   Leu   Thr   Arg   Leu   Val   Thr   Leu   Asp
      145                     150                     155                     160 ctc   tca   act   att   ctc   cct   ttt   ttt   gat   cag   cca   ctt   aaa   ctt   gag   aat       528
      Leu   Ser   Thr   Ile   Leu   Pro   Phe   Phe   Asp   Gln   Pro   Leu   Lys   Leu   Glu   Asn
                              165                     170                     175 ccc   aat   ttg   agt   cat   ttc   att   gag   aac   tca   aca   gag   ctt   aga   gag   ctt       576
      Pro   Asn   Leu   Ser   His   Phe   Ile   Glu   Asn   Ser   Thr   Glu   Leu   Arg   Glu   Leu
                        180                     185                     190 tac   ctt   gat   ggg   gtt   gat   ctt   tcg   tct   cag   agg   act   gag   tgg   tgt   caa       624
      Tyr   Leu   Asp   Gly   Val   Asp   Leu   Ser   Ser   Gln   Arg   Thr   Glu   Trp   Cys   Gln
            195                     200                     205 tct   tta   tct   tta   cat   ttg   cct   aac   ttg   acc   gtt   ttg   agc   ttg   cgt   gat       672
      Ser   Leu   Ser   Leu   His   Leu   Pro   Asn   Leu   Thr   Val   Leu   Ser   Leu   Arg   Asp
      210                     215                     220 tgt   caa   att   tca   ggc   cct   ttg   gat   gaa   tca   ctt   tct   aag   ctt   cac   ttt       720
      Cys   Gln   Ile   Ser   Gly   Pro   Leu   Asp   Glu   Ser   Leu   Ser   Lys   Leu   His   Phe
      225                     230                     235                     240 ctc   tct   ttt   gtc   caa   ctt   gac   cag   aac   aat   ctc   tct   agc   aca   gtt   cct       768
      Leu   Ser   Phe   Val   Gln   Leu   Asp   Gln   Asn   Asn   Leu   Ser   Ser   Thr   Val   Pro
                              245                     250                     255 gaa   tat   ttt   gcc   aat   ttc   tcg   aac   ttg   act   aca   ttg   acc   ctg   ggc   tct       816
      Glu   Tyr   Phe   Ala   Asn   Phe   Ser   Asn   Leu   Thr   Thr   Leu   Thr   Leu   Gly   Ser
                        260                     265                     270 tgt   aat   cta   cag   gga   aca   ttt   cct   gaa   aga   atc   ttt   cag   gta   tca   gtt       864
      Cys   Asn   Leu   Gln   Gly   Thr   Phe   Pro   Glu   Arg   Ile   Phe   Gln   Val   Ser   Val
            275                     280                     285 tta   gag   agt   ttg   gac   ttg   tca   att   aac   aag   ttg   ctt   cgt   ggt   agt   att       912
      Leu   Glu   Ser   Leu   Asp   Leu   Ser   Ile   Asn   Lys   Leu   Leu   Arg   Gly   Ser   Ile
      290                     295                     300 cca   att   ttt   ttc   cga   aat   gga   tct   ctg   agg   agg   ata   tca   cta   agc   tac       960
      Pro   Ile   Phe   Phe   Arg   Asn   Gly   Ser   Leu   Arg   Arg   Ile   Ser   Leu   Ser   Tyr
      305                     310                     315                     320 acc   aac   ttt   tcc   ggt   tca   tta   cca   gag   tcc   att   tcg   aac   cat   caa   aat      1008
```

-continued

```
Thr Asn Phe Ser Gly Ser Leu Pro Glu Ser Ile Ser Asn His Gln Asn
            325                 330                 335 cta tcc agg tta gag ctt tct aat tgc aat ttc tat gga tca ata cct      1056
Leu Ser Arg Leu Glu Leu Ser Asn Cys Asn Phe Tyr Gly Ser Ile Pro
        340                 345                 350 tcc aca atg gca aac ctt aga aat ctt ggt tat ttg gat ttc tcc ttc      1104
Ser Thr Met Ala Asn Leu Arg Asn Leu Gly Tyr Leu Asp Phe Ser Phe
            355                 360                 365 aac aat ttc act ggt tct atc cca tat ttt cga ctg tcc aag aaa ctc      1152
Asn Asn Phe Thr Gly Ser Ile Pro Tyr Phe Arg Leu Ser Lys Lys Leu
370                 375                 380 acc tac tta gac ctt tca cgt aat ggt cta act ggt ctc ttg tct aga      1200
Thr Tyr Leu Asp Leu Ser Arg Asn Gly Leu Thr Gly Leu Leu Ser Arg
385                 390                 395                 400 gct cat ttt gaa gga ctc tca gag ctt gtc cac att aat tta ggg aac      1248
Ala His Phe Glu Gly Leu Ser Glu Leu Val His Ile Asn Leu Gly Asn
                405                 410                 415 aat tta ctc agc ggg agc ctt cct gca tat ata ttt gag ctc ccc tcg      1296
Asn Leu Leu Ser Gly Ser Leu Pro Ala Tyr Ile Phe Glu Leu Pro Ser
            420                 425                 430 ttg cag cag ctt ttt ctt tac aga aat caa ttt gtt ggc caa gtc gac      1344
Leu Gln Gln Leu Phe Leu Tyr Arg Asn Gln Phe Val Gly Gln Val Asp
        435                 440                 445 gaa ttt cgc aat gca tcc tcc tct ccg ttg gat aca gtt gac ttg aca      1392
Glu Phe Arg Asn Ala Ser Ser Ser Pro Leu Asp Thr Val Asp Leu Thr
450                 455                 460 aac aac cac ctg aat gga tcg att ccg aag tcc atg ttt gaa att gaa      1440
Asn Asn His Leu Asn Gly Ser Ile Pro Lys Ser Met Phe Glu Ile Glu
465                 470                 475                 480 agg ctt aag gtg ctc tca ctt tct tcc aac ttc ttt aga ggg aca gtg      1488
Arg Leu Lys Val Leu Ser Leu Ser Ser Asn Phe Phe Arg Gly Thr Val
                485                 490                 495 ccc ctt gac ctc att ggg agg ctg agc aac ctt tca aga ctg gag ctt      1536
Pro Leu Asp Leu Ile Gly Arg Leu Ser Asn Leu Ser Arg Leu Glu Leu
            500                 505                 510 tct tac aat aac ttg act gtt gat gca agt agc agc aat tca acc tct      1584
Ser Tyr Asn Asn Leu Thr Val Asp Ala Ser Ser Ser Asn Ser Thr Ser
        515                 520                 525 ttc aca ttt ccc cag ttg aac ata ttg aaa tta gcg tct tgt cgg ctg      1632
Phe Thr Phe Pro Gln Leu Asn Ile Leu Lys Leu Ala Ser Cys Arg Leu
530                 535                 540 caa aag ttc ccc gat ctc aag aat cag tca tgg atg atg cac tta gac      1680
Gln Lys Phe Pro Asp Leu Lys Asn Gln Ser Trp Met Met His Leu Asp
545                 550                 555                 560 ctt tca gac aac caa ata ttg ggg gca ata cca aat tgg atc tgg gga      1728
Leu Ser Asp Asn Gln Ile Leu Gly Ala Ile Pro Asn Trp Ile Trp Gly
                565                 570                 575 att ggt ggt gga ggt ctc acc cac ctg aat ctt tca ttc aat cag ctg      1776
Ile Gly Gly Gly Gly Leu Thr His Leu Asn Leu Ser Phe Asn Gln Leu
            580                 585                 590 gag tac gtg gaa cag cct tac act gct tcc agc aat ctt gta gtc ctt      1824
Glu Tyr Val Glu Gln Pro Tyr Thr Ala Ser Ser Asn Leu Val Val Leu
        595                 600                 605 gat ttg cat tcc aac cgt tta aaa ggt gac tta cta ata cca cct tgc      1872
Asp Leu His Ser Asn Arg Leu Lys Gly Asp Leu Leu Ile Pro Pro Cys
610                 615                 620 act gcc atc tat gtg gac tac tct agc aat aat tta aac aat tcc atc      1920
Thr Ala Ile Tyr Val Asp Tyr Ser Ser Asn Asn Leu Asn Asn Ser Ile
625                 630                 635                 640
```

```
cca aca gat att gga aag tct ctt ggt ttt gcc tcc ttt ttc tcg gta    1968
Pro Thr Asp Ile Gly Lys Ser Leu Gly Phe Ala Ser Phe Phe Ser Val
            645                 650                 655 gca aac aat ggc att act gga ata att cct gaa tcc ata tgc aac tgc    2016
Ala Asn Asn Gly Ile Thr Gly Ile Ile Pro Glu Ser Ile Cys Asn Cys
            660                 665                 670 agc tac ctt caa gtt ctt gat ttc tct aac aat gcc ttg agt gga aca    2064
Ser Tyr Leu Gln Val Leu Asp Phe Ser Asn Asn Ala Leu Ser Gly Thr
            675                 680                 685 ata cca cca tgt cta ctg gaa tat agt aca aaa ctt gga gtg ctg aat    2112
Ile Pro Pro Cys Leu Leu Glu Tyr Ser Thr Lys Leu Gly Val Leu Asn
            690                 695                 700 ctt ggg aac aat aaa ctc aat ggt gtt ata cca gat tca ttt tca att    2160
Leu Gly Asn Asn Lys Leu Asn Gly Val Ile Pro Asp Ser Phe Ser Ile
705                 710                 715                 720 ggt tgt gct cta caa aca tta gac ctc agt gcg aat aac tta caa ggc    2208
Gly Cys Ala Leu Gln Thr Leu Asp Leu Ser Ala Asn Asn Leu Gln Gly
            725                 730                 735 agg ctg cca aaa tcg att gtg aat tgt aag ttg ttg gag gtc ctg aat    2256
Arg Leu Pro Lys Ser Ile Val Asn Cys Lys Leu Leu Glu Val Leu Asn
            740                 745                 750 gtt gga aat aac aga ctt gtt gat cat ttc cca tgc atg ttg agg aac    2304
Val Gly Asn Asn Arg Leu Val Asp His Phe Pro Cys Met Leu Arg Asn
            755                 760                 765 tca aac agt ctg agg gtc cta gtc ttg cgc tcc aat aaa ttc tat gga    2352
Ser Asn Ser Leu Arg Val Leu Val Leu Arg Ser Asn Lys Phe Tyr Gly
            770                 775                 780 aat ctt atg tgt gat gta acc aga aat agc tgg cag aat ctc cag atc    2400
Asn Leu Met Cys Asp Val Thr Arg Asn Ser Trp Gln Asn Leu Gln Ile
785                 790                 795                 800 ata gat ata gct tcc aac aac ttc act ggt gtg ttg aat gca gaa ttc    2448
Ile Asp Ile Ala Ser Asn Asn Phe Thr Gly Val Leu Asn Ala Glu Phe
            805                 810                 815 ttt tca aat tgg aga gga atg atg gtt gca gat gat tac gtg gag aca    2496
Phe Ser Asn Trp Arg Gly Met Met Val Ala Asp Asp Tyr Val Glu Thr
            820                 825                 830 gga cgc aat cat atc cag tat gag ttc tta caa cta agt aaa ttg tac    2544
Gly Arg Asn His Ile Gln Tyr Glu Phe Leu Gln Leu Ser Lys Leu Tyr
            835                 840                 845 tat cag gac aca gtg aca tta acc atc aaa ggc atg gag ctg gag ctt    2592
Tyr Gln Asp Thr Val Thr Leu Thr Ile Lys Gly Met Glu Leu Glu Leu
850                 855                 860 gtg aag att ctc agg gtc ttc aca tct att gat ttc tct tcc aat aga    2640
Val Lys Ile Leu Arg Val Phe Thr Ser Ile Asp Phe Ser Ser Asn Arg
865                 870                 875                 880 ttt caa gga gcg ata cca gat gct atc ggg aat ctc agc tca ctt tat    2688
Phe Gln Gly Ala Ile Pro Asp Ala Ile Gly Asn Leu Ser Ser Leu Tyr
            885                 890                 895 gtt ctg aat ctg tca cac aat gcc ctt gag gga cca atc cca aaa tcg    2736
Val Leu Asn Leu Ser His Asn Ala Leu Glu Gly Pro Ile Pro Lys Ser
            900                 905                 910 att ggg aag cta caa atg ctt gaa tca cta gac ctg tca aca aac cac    2784
Ile Gly Lys Leu Gln Met Leu Glu Ser Leu Asp Leu Ser Thr Asn His
            915                 920                 925 ctg tcc ggg gag atc cca tca gag ctt gca agt ctc aca ttc tta gca    2832
Leu Ser Gly Glu Ile Pro Ser Glu Leu Ala Ser Leu Thr Phe Leu Ala
930                 935                 940 gct ttg aac tta tcg ttc aac aaa ttg ttt ggc aaa att cca tca act    2880
Ala Leu Asn Leu Ser Phe Asn Lys Leu Phe Gly Lys Ile Pro Ser Thr
945                 950                 955                 960
```

-continued

```
aat cag ttt caa aca ttc tca gca gat tcc ttt gaa gga aac agt ggc    2928
Asn Gln Phe Gln Thr Phe Ser Ala Asp Ser Phe Glu Gly Asn Ser Gly
            965                 970                 975 cta tgc ggg ctc cct ctc aac aac agt tgt caa agc aat ggc tca gcc    2976
Leu Cys Gly Leu Pro Leu Asn Asn Ser Cys Gln Ser Asn Gly Ser Ala
        980                 985                 990 tca gag tcc ctg cct cca cca act ccg cta cca gac tca gat gat gaa    3024
Ser Glu Ser Leu Pro Pro Pro Thr Pro Leu Pro Asp Ser Asp Asp Glu
    995                 1000                1005 tgg gag ttc att ttt gca gca gtt gga tac ata gta ggg gca gca aat    3072
Trp Glu Phe Ile Phe Ala Ala Val Gly Tyr Ile Val Gly Ala Ala Asn
 1010                1015                1020 act att tca gtt gtg tgg ttt tac aag cca gtg aag aaa tgg ttt gat    3120
Thr Ile Ser Val Val Trp Phe Tyr Lys Pro Val Lys Lys Trp Phe Asp
1025                1030                1035                1040 aag cat atg gag aaa tgc ttg ctt tgg ttt tca aga aag tga            3162
Lys His Met Glu Lys Cys Leu Leu Trp Phe Ser Arg Lys
                1045                1050

<210> SEQ ID NO 6
<211> LENGTH: 1053
<212> TYPE: PRT
<213> ORGANISM: Lycopersicon esculentum

<400> SEQUENCE: 6

Met Lys Met Met Ala Thr Leu Tyr Phe Pro Met Val Leu Leu Ile Pro
 1               5                  10                  15

Ser Phe Gln Ile Leu Ser Gly Tyr His Ile Phe Leu Val Ser Ser Gln
            20                  25                  30

Cys Leu Asp Asp Gln Lys Ser Leu Leu Leu Gln Phe Lys Gly Ser Leu
        35                  40                  45

Gln Tyr Asp Ser Thr Leu Ser Lys Lys Leu Ala Lys Trp Asn Asp Met
    50                  55                  60

Thr Ser Glu Cys Cys Asn Trp Asn Gly Val Thr Cys Asn Leu Phe Gly
 65                  70                  75                  80

His Val Ile Ala Leu Glu Leu Asp Asp Glu Thr Ile Ser Ser Gly Ile
                85                  90                  95

Glu Asn Ser Ser Ala Leu Phe Ser Leu Gln Tyr Leu Glu Ser Leu Asn
            100                 105                 110

Leu Ala Asp Asn Met Phe Asn Val Gly Ile Pro Val Gly Ile Asp Asn
        115                 120                 125

Leu Thr Asn Leu Lys Tyr Leu Asn Leu Ser Asn Ala Gly Phe Val Gly
    130                 135                 140

Gln Ile Pro Ile Thr Leu Ser Arg Leu Thr Arg Leu Val Thr Leu Asp
145                 150                 155                 160

Leu Ser Thr Ile Leu Pro Phe Phe Asp Gln Pro Leu Lys Leu Glu Asn
                165                 170                 175

Pro Asn Leu Ser His Phe Ile Glu Asn Ser Thr Glu Leu Arg Glu Leu
            180                 185                 190

Tyr Leu Asp Gly Val Asp Leu Ser Ser Gln Arg Thr Glu Trp Cys Gln
        195                 200                 205

Ser Leu Ser Leu His Leu Pro Asn Leu Thr Val Leu Ser Leu Arg Asp
    210                 215                 220

Cys Gln Ile Ser Gly Pro Leu Asp Glu Ser Leu Ser Lys Leu His Phe
225                 230                 235                 240

Leu Ser Phe Val Gln Leu Asp Gln Asn Asn Leu Ser Ser Thr Val Pro
```

-continued

```
                245                 250                 255
Glu Tyr Phe Ala Asn Phe Ser Asn Leu Thr Thr Leu Thr Leu Gly Ser
            260                 265                 270
Cys Asn Leu Gln Gly Thr Phe Pro Glu Arg Ile Phe Gln Val Ser Val
        275                 280                 285
Leu Glu Ser Leu Asp Leu Ser Ile Asn Lys Leu Leu Arg Gly Ser Ile
    290                 295                 300
Pro Ile Phe Phe Arg Asn Gly Ser Leu Arg Arg Ile Ser Leu Ser Tyr
305                 310                 315                 320
Thr Asn Phe Ser Gly Ser Leu Pro Glu Ser Ile Ser Asn His Gln Asn
                325                 330                 335
Leu Ser Arg Leu Glu Leu Ser Asn Cys Asn Phe Tyr Gly Ser Ile Pro
            340                 345                 350
Ser Thr Met Ala Asn Leu Arg Asn Leu Gly Tyr Leu Asp Phe Ser Phe
        355                 360                 365
Asn Asn Phe Thr Gly Ser Ile Pro Tyr Phe Arg Leu Ser Lys Lys Leu
    370                 375                 380
Thr Tyr Leu Asp Leu Ser Arg Asn Gly Leu Thr Gly Leu Leu Ser Arg
385                 390                 395                 400
Ala His Phe Glu Gly Leu Ser Glu Leu Val His Ile Asn Leu Gly Asn
                405                 410                 415
Asn Leu Leu Ser Gly Ser Leu Pro Ala Tyr Ile Phe Glu Leu Pro Ser
            420                 425                 430
Leu Gln Gln Leu Phe Leu Tyr Arg Asn Gln Phe Val Gly Gln Val Asp
        435                 440                 445
Glu Phe Arg Asn Ala Ser Ser Pro Leu Asp Thr Val Asp Leu Thr
    450                 455                 460
Asn Asn His Leu Asn Gly Ser Ile Pro Lys Ser Met Phe Glu Ile Glu
465                 470                 475                 480
Arg Leu Lys Val Leu Ser Leu Ser Asn Phe Phe Arg Gly Thr Val
                485                 490                 495
Pro Leu Asp Leu Ile Gly Arg Leu Ser Asn Leu Ser Arg Leu Glu Leu
            500                 505                 510
Ser Tyr Asn Asn Leu Thr Val Asp Ala Ser Ser Ser Asn Ser Thr Ser
        515                 520                 525
Phe Thr Phe Pro Gln Leu Asn Ile Leu Lys Leu Ala Ser Cys Arg Leu
    530                 535                 540
Gln Lys Phe Pro Asp Leu Lys Asn Gln Ser Trp Met Met His Leu Asp
545                 550                 555                 560
Leu Ser Asp Asn Gln Ile Leu Gly Ala Ile Pro Asn Trp Ile Trp Gly
                565                 570                 575
Ile Gly Gly Gly Leu Thr His Leu Asn Leu Ser Phe Asn Gln Leu
            580                 585                 590
Glu Tyr Val Glu Gln Pro Tyr Thr Ala Ser Ser Asn Leu Val Val Leu
        595                 600                 605
Asp Leu His Ser Asn Arg Leu Lys Gly Asp Leu Leu Ile Pro Pro Cys
    610                 615                 620
Thr Ala Ile Tyr Val Asp Tyr Ser Ser Asn Leu Asn Asn Ser Ile
625                 630                 635                 640
Pro Thr Asp Ile Gly Lys Ser Leu Gly Phe Ala Ser Phe Ser Val
                645                 650                 655
Ala Asn Asn Gly Ile Thr Gly Ile Ile Pro Glu Ser Ile Cys Asn Cys
            660                 665                 670
```

Ser Tyr Leu Gln Val Leu Asp Phe Ser Asn Asn Ala Leu Ser Gly Thr
            675                 680                 685

Ile Pro Pro Cys Leu Leu Glu Tyr Ser Thr Lys Leu Gly Val Leu Asn
        690                 695                 700

Leu Gly Asn Asn Lys Leu Asn Gly Val Ile Pro Asp Ser Phe Ser Ile
705                 710                 715                 720

Gly Cys Ala Leu Gln Thr Leu Asp Leu Ser Ala Asn Asn Leu Gln Gly
                725                 730                 735

Arg Leu Pro Lys Ser Ile Val Asn Cys Lys Leu Leu Glu Val Leu Asn
            740                 745                 750

Val Gly Asn Asn Arg Leu Val Asp His Phe Pro Cys Met Leu Arg Asn
            755                 760                 765

Ser Asn Ser Leu Arg Val Leu Val Leu Arg Ser Asn Lys Phe Tyr Gly
            770                 775                 780

Asn Leu Met Cys Asp Val Thr Arg Asn Ser Trp Gln Asn Leu Gln Ile
785                 790                 795                 800

Ile Asp Ile Ala Ser Asn Asn Phe Thr Gly Val Leu Asn Ala Glu Phe
                805                 810                 815

Phe Ser Asn Trp Arg Gly Met Met Val Ala Asp Asp Tyr Val Glu Thr
            820                 825                 830

Gly Arg Asn His Ile Gln Tyr Glu Phe Leu Gln Leu Ser Lys Leu Tyr
            835                 840                 845

Tyr Gln Asp Thr Val Thr Leu Thr Ile Lys Gly Met Glu Leu Glu Leu
            850                 855                 860

Val Lys Ile Leu Arg Val Phe Thr Ser Ile Asp Phe Ser Ser Asn Arg
865                 870                 875                 880

Phe Gln Gly Ala Ile Pro Asp Ala Ile Gly Asn Leu Ser Ser Leu Tyr
                885                 890                 895

Val Leu Asn Leu Ser His Asn Ala Leu Glu Gly Pro Ile Pro Lys Ser
            900                 905                 910

Ile Gly Lys Leu Gln Met Leu Glu Ser Leu Asp Leu Ser Thr Asn His
            915                 920                 925

Leu Ser Gly Glu Ile Pro Ser Glu Leu Ala Ser Leu Thr Phe Leu Ala
            930                 935                 940

Ala Leu Asn Leu Ser Phe Asn Lys Leu Phe Gly Lys Ile Pro Ser Thr
945                 950                 955                 960

Asn Gln Phe Gln Thr Phe Ser Ala Asp Ser Phe Glu Gly Asn Ser Gly
                965                 970                 975

Leu Cys Gly Leu Pro Leu Asn Asn Ser Cys Gln Ser Asn Gly Ser Ala
            980                 985                 990

Ser Glu Ser Leu Pro Pro Pro Thr Pro Leu Pro Asp Ser Asp Asp Glu
            995                 1000                1005

Trp Glu Phe Ile Phe Ala Ala Val Gly Tyr Ile Val Gly Ala Ala Asn
    1010                1015                1020

Thr Ile Ser Val Val Trp Phe Tyr Lys Pro Val Lys Trp Phe Asp
1025                1030                1035                1040

Lys His Met Glu Lys Cys Leu Leu Trp Phe Ser Arg Lys
                1045                1050

<210> SEQ ID NO 7
<211> LENGTH: 3382
<212> TYPE: DNA
<213> ORGANISM: Lycopersicon esculentum
<220> FEATURE:

-continued

```
<221> NAME/KEY: misc_feature
<222> LOCATION: (1)..(3382)
<223> OTHER INFORMATION: Ve1.2 cDNA sequence
<220> FEATURE:
<221> NAME/KEY: CDS
<222> LOCATION: (1)..(3162)

<400> SEQUENCE: 7
```

| | | | | | | | | | | | | | | | | |
|---|---|---|---|---|---|---|---|---|---|---|---|---|---|---|---|---|
| atg | aaa | atg | atg | gca | act | ctg | tac | ttc | cct | atg | gtt | ctc | ttg | att | ccc | 48 |
| Met | Lys | Met | Met | Ala | Thr | Leu | Tyr | Phe | Pro | Met | Val | Leu | Leu | Ile | Pro | |
| 1 | | | | 5 | | | | | 10 | | | | | 15 | | |
| tcg | ttt | caa | atc | tta | tca | gga | tac | cac | att | ttc | ttg | gtt | tcc | tct | caa | 96 |
| Ser | Phe | Gln | Ile | Leu | Ser | Gly | Tyr | His | Ile | Phe | Leu | Val | Ser | Ser | Gln | |
| | | | 20 | | | | | 25 | | | | | 30 | | | |
| tgc | ctt | gac | gat | caa | aag | tca | ttg | ttg | ctg | cag | ttt | aag | gga | agc | ctc | 144 |
| Cys | Leu | Asp | Asp | Gln | Lys | Ser | Leu | Leu | Leu | Gln | Phe | Lys | Gly | Ser | Leu | |
| | | 35 | | | | | 40 | | | | | 45 | | | | |
| caa | tat | gat | tct | act | ttg | tca | aag | aaa | ttg | gca | aaa | tgg | aac | gac | atg | 192 |
| Gln | Tyr | Asp | Ser | Thr | Leu | Ser | Lys | Lys | Leu | Ala | Lys | Trp | Asn | Asp | Met | |
| 50 | | | | | 55 | | | | | 60 | | | | | | |
| aca | agt | gaa | tgt | tgc | aat | tgg | aat | ggg | gtt | aca | tgc | aat | ctc | ttt | ggt | 240 |
| Thr | Ser | Glu | Cys | Cys | Asn | Trp | Asn | Gly | Val | Thr | Cys | Asn | Leu | Phe | Gly | |
| 65 | | | | 70 | | | | | 75 | | | | | 80 | | |
| cat | gtc | atc | gct | ttg | gaa | ctg | gat | gat | gag | act | att | tct | agt | gga | att | 288 |
| His | Val | Ile | Ala | Leu | Glu | Leu | Asp | Asp | Glu | Thr | Ile | Ser | Ser | Gly | Ile | |
| | | | | 85 | | | | | 90 | | | | | 95 | | |
| gag | aat | tct | agt | gca | ctt | ttc | agt | ctt | caa | tat | ctt | gag | agc | cta | aat | 336 |
| Glu | Asn | Ser | Ser | Ala | Leu | Phe | Ser | Leu | Gln | Tyr | Leu | Glu | Ser | Leu | Asn | |
| | | | 100 | | | | | 105 | | | | | 110 | | | |
| ttg | gct | gac | aac | atg | ttc | aat | gtt | ggc | ata | cca | gtt | ggt | ata | gac | aac | 384 |
| Leu | Ala | Asp | Asn | Met | Phe | Asn | Val | Gly | Ile | Pro | Val | Gly | Ile | Asp | Asn | |
| | | 115 | | | | | 120 | | | | | 125 | | | | |
| ctc | aca | aac | ttg | aag | tac | ctg | aat | tta | tcc | aat | gct | ggt | ttt | gtc | ggg | 432 |
| Leu | Thr | Asn | Leu | Lys | Tyr | Leu | Asn | Leu | Ser | Asn | Ala | Gly | Phe | Val | Gly | |
| | 130 | | | | | 135 | | | | | 140 | | | | | |
| caa | att | cct | ata | aca | tta | tca | aga | tta | aca | agg | cta | gtt | act | ctt | gat | 480 |
| Gln | Ile | Pro | Ile | Thr | Leu | Ser | Arg | Leu | Thr | Arg | Leu | Val | Thr | Leu | Asp | |
| 145 | | | | | 150 | | | | | 155 | | | | | 160 | |
| ctc | tca | act | att | ctc | cct | ttt | ttt | gat | cag | cca | ctt | aaa | ctt | gag | aat | 528 |
| Leu | Ser | Thr | Ile | Leu | Pro | Phe | Phe | Asp | Gln | Pro | Leu | Lys | Leu | Glu | Asn | |
| | | | | 165 | | | | | 170 | | | | | 175 | | |
| ccc | aat | ttg | agt | cat | ttc | att | gag | aac | tca | aca | gag | ctt | aga | gag | ctt | 576 |
| Pro | Asn | Leu | Ser | His | Phe | Ile | Glu | Asn | Ser | Thr | Glu | Leu | Arg | Glu | Leu | |
| | | | 180 | | | | | 185 | | | | | 190 | | | |
| tac | ctt | gat | ggg | gtt | gat | ctt | tcg | tct | cag | agg | tct | gag | tgg | tgt | caa | 624 |
| Tyr | Leu | Asp | Gly | Val | Asp | Leu | Ser | Ser | Gln | Arg | Ser | Glu | Trp | Cys | Gln | |
| | | 195 | | | | | 200 | | | | | 205 | | | | |
| tct | tta | tct | tta | cat | ttg | cct | aac | ttg | acc | gtt | ttg | agc | ttg | cgt | gat | 672 |
| Ser | Leu | Ser | Leu | His | Leu | Pro | Asn | Leu | Thr | Val | Leu | Ser | Leu | Arg | Asp | |
| | 210 | | | | | 215 | | | | | 220 | | | | | |
| tgt | caa | att | tca | ggc | cct | ttg | gat | gaa | tca | ctt | act | aag | ctt | cac | ttt | 720 |
| Cys | Gln | Ile | Ser | Gly | Pro | Leu | Asp | Glu | Ser | Leu | Thr | Lys | Leu | His | Phe | |
| 225 | | | | | 230 | | | | | 235 | | | | | 240 | |
| ctc | tct | ttt | gtc | caa | ctt | gac | cag | aac | aat | ctc | tct | agc | aca | gtt | cct | 768 |
| Leu | Ser | Phe | Val | Gln | Leu | Asp | Gln | Asn | Asn | Leu | Ser | Ser | Thr | Val | Pro | |
| | | | | 245 | | | | | 250 | | | | | 255 | | |
| gaa | tat | ttt | gcc | aat | ttc | tcg | aac | ttg | act | aca | ttg | acc | ctg | ggc | tct | 816 |
| Glu | Tyr | Phe | Ala | Asn | Phe | Ser | Asn | Leu | Thr | Thr | Leu | Thr | Leu | Gly | Ser | |
| | | | 260 | | | | | 265 | | | | | 270 | | | |
| tgt | aat | cta | cag | gga | aca | ttt | cct | gaa | aga | atc | ttt | cag | gta | tca | gtt | 864 |
| Cys | Asn | Leu | Gln | Gly | Thr | Phe | Pro | Glu | Arg | Ile | Phe | Gln | Val | Ser | Val | |

```
                275                 280                 285
tta gag agt ttg gac ttg tca att aac aag ttg ctt cgt ggt agt att    912
Leu Glu Ser Leu Asp Leu Ser Ile Asn Lys Leu Leu Arg Gly Ser Ile
    290                 295                 300 cca att ttt ttc cga aat gga tct ctg agg agg ata tca cta agc tac    960
Pro Ile Phe Phe Arg Asn Gly Ser Leu Arg Arg Ile Ser Leu Ser Tyr
305                 310                 315                 320 acc aac ttt tcc ggt tca tta cca gag tcc att tcg aac cat caa aat   1008
Thr Asn Phe Ser Gly Ser Leu Pro Glu Ser Ile Ser Asn His Gln Asn
                325                 330                 335 cta tcc agg tta gag ctt tct aat tgc aat ttc tat gga tca ata cct   1056
Leu Ser Arg Leu Glu Leu Ser Asn Cys Asn Phe Tyr Gly Ser Ile Pro
            340                 345                 350 tcc aca atg gca aac ctt aga aat ctt ggt tat ttg gat ttc tcc ttc   1104
Ser Thr Met Ala Asn Leu Arg Asn Leu Gly Tyr Leu Asp Phe Ser Phe
        355                 360                 365 aac aat ttc act ggt tct atc cca tat ttt cga ctg tcc aag aaa ctc   1152
Asn Asn Phe Thr Gly Ser Ile Pro Tyr Phe Arg Leu Ser Lys Lys Leu
    370                 375                 380 acc tac tta gac ctt tca cgt aat ggt cta act ggt ctc ttg tct aga   1200
Thr Tyr Leu Asp Leu Ser Arg Asn Gly Leu Thr Gly Leu Leu Ser Arg
385                 390                 395                 400 gct cat ttt gaa gga ctc tca gag ctt gtc cac att aat tta ggg aac   1248
Ala His Phe Glu Gly Leu Ser Glu Leu Val His Ile Asn Leu Gly Asn
                405                 410                 415 aat tta ctc agc ggg agc ctt cct gca tat ata ttt gag ctc ccc tcg   1296
Asn Leu Leu Ser Gly Ser Leu Pro Ala Tyr Ile Phe Glu Leu Pro Ser
            420                 425                 430 ttg cag cag ctt ttt ctt tac aga aat caa ttt gtt ggc caa gtc gac   1344
Leu Gln Gln Leu Phe Leu Tyr Arg Asn Gln Phe Val Gly Gln Val Asp
        435                 440                 445 gaa ttt cgc aat gca tcc tcc tct ccg ttg gat aca gtt gac ttg aca   1392
Glu Phe Arg Asn Ala Ser Ser Ser Pro Leu Asp Thr Val Asp Leu Thr
    450                 455                 460 aac aac cac ctg aat gga tcg att ccg aag tcc atg ttt gaa att gaa   1440
Asn Asn His Leu Asn Gly Ser Ile Pro Lys Ser Met Phe Glu Ile Glu
465                 470                 475                 480 agg ctt aag gtg ctc tca ctt tct tcc aac ttc ttt aga ggg aca gtg   1488
Arg Leu Lys Val Leu Ser Leu Ser Ser Asn Phe Phe Arg Gly Thr Val
                485                 490                 495 ccc ctt gac ctc att ggg agg ctg agc aac ctt tca aga ctg gag ctt   1536
Pro Leu Asp Leu Ile Gly Arg Leu Ser Asn Leu Ser Arg Leu Glu Leu
            500                 505                 510 tct tac aat aag ttg act gtt gat gca agt agc agc aat tca acc tct   1584
Ser Tyr Asn Lys Leu Thr Val Asp Ala Ser Ser Ser Asn Ser Thr Ser
        515                 520                 525 ttc aca ttt ccc cag ttg aac ata ttg aaa tta gcg tct tgt cgg ctg   1632
Phe Thr Phe Pro Gln Leu Asn Ile Leu Lys Leu Ala Ser Cys Arg Leu
    530                 535                 540 caa aag ttc ccc gat ctc aag aat cag tca tgg atg atg cac tta gac   1680
Gln Lys Phe Pro Asp Leu Lys Asn Gln Ser Trp Met Met His Leu Asp
545                 550                 555                 560 ctt tca gac aac caa ata ttg ggg gca ata cca aat tgg atc tgg gga   1728
Leu Ser Asp Asn Gln Ile Leu Gly Ala Ile Pro Asn Trp Ile Trp Gly
                565                 570                 575 att ggt ggt gga ggt ctc acc cac ctg aat ctt tca ttc aat cag ctg   1776
Ile Gly Gly Gly Gly Leu Thr His Leu Asn Leu Ser Phe Asn Gln Leu
            580                 585                 590 gag tac gtg gaa cag cct tac act gct tcc agc aat ctt gta gtc ctt   1824
```

```
                Glu Tyr Val Glu Gln Pro Tyr Thr Ala Ser Ser Asn Leu Val Val Leu
                                595                 600                 605 gat ttg cat tcc aac cgt tta aaa ggt gac tta cta ata cca cct tgc        1872
Asp Leu His Ser Asn Arg Leu Lys Gly Asp Leu Leu Ile Pro Pro Cys
    610                 615                 620 act gcc atc tat gtg aac tac tct agc aat aat tta aac aat tcc atc        1920
Thr Ala Ile Tyr Val Asn Tyr Ser Ser Asn Asn Leu Asn Asn Ser Ile
625                 630                 635                 640 cca aca gat att gga aag tct ctt ggt ttt gcc tcc ttt ttc tcg gta        1968
Pro Thr Asp Ile Gly Lys Ser Leu Gly Phe Ala Ser Phe Phe Ser Val
                645                 650                 655 gca aac aat ggc att act gga ata att cct gaa tcc ata tgc aac tgc        2016
Ala Asn Asn Gly Ile Thr Gly Ile Ile Pro Glu Ser Ile Cys Asn Cys
            660                 665                 670 agc tac ctt caa gtt ctt gat ttc tct aac aat gcc ttg agt gga aca        2064
Ser Tyr Leu Gln Val Leu Asp Phe Ser Asn Asn Ala Leu Ser Gly Thr
        675                 680                 685 ata cca cca tgt cta ctg gaa tat agt aca aaa ctt gga gtg ctg aat        2112
Ile Pro Pro Cys Leu Leu Glu Tyr Ser Thr Lys Leu Gly Val Leu Asn
    690                 695                 700 ctt ggg aac aat aaa ctc aat ggt gtt ata cca gat tca ttt tca att        2160
Leu Gly Asn Asn Lys Leu Asn Gly Val Ile Pro Asp Ser Phe Ser Ile
705                 710                 715                 720 ggt tgt gct cta caa aca tta gac ctc agt gcg aat aac tta caa ggc        2208
Gly Cys Ala Leu Gln Thr Leu Asp Leu Ser Ala Asn Asn Leu Gln Gly
                725                 730                 735 agg ctg cca aaa tcg att gtg aat tgt aag ttg ttg gag gtc ctg aat        2256
Arg Leu Pro Lys Ser Ile Val Asn Cys Lys Leu Leu Glu Val Leu Asn
            740                 745                 750 gtt gga aat aac aga ctt gtt gat cat ttc cca tgc atg ttg agg aac        2304
Val Gly Asn Asn Arg Leu Val Asp His Phe Pro Cys Met Leu Arg Asn
        755                 760                 765 tca aac agt ctg agg gtc cta gtc ttg cgc tcc aat aaa ttc tat gga        2352
Ser Asn Ser Leu Arg Val Leu Val Leu Arg Ser Asn Lys Phe Tyr Gly
    770                 775                 780 aat ctt atg tgt gat gta acc aga aat agc tgg cag aat ctc cag atc        2400
Asn Leu Met Cys Asp Val Thr Arg Asn Ser Trp Gln Asn Leu Gln Ile
785                 790                 795                 800 ata gat ata gct tcc aac aac ttc act ggt gtg ttg aat gca gaa ttc        2448
Ile Asp Ile Ala Ser Asn Asn Phe Thr Gly Val Leu Asn Ala Glu Phe
                805                 810                 815 ttt tca aat tgg aga gga atg atg gtt gca gat gat tac gtg gag aca        2496
Phe Ser Asn Trp Arg Gly Met Met Val Ala Asp Asp Tyr Val Glu Thr
            820                 825                 830 gga cgc aat cat atc cag tat gag ttc tta caa cta agt aaa ttg tac        2544
Gly Arg Asn His Ile Gln Tyr Glu Phe Leu Gln Leu Ser Lys Leu Tyr
        835                 840                 845 tat cag gac aca gtg aca tta acc atc aaa ggc atg gag ctg gag ctt        2592
Tyr Gln Asp Thr Val Thr Leu Thr Ile Lys Gly Met Glu Leu Glu Leu
    850                 855                 860 gtg aag att ctc agg gtc ttc aca tct att gat ttc tct tcc aat aga        2640
Val Lys Ile Leu Arg Val Phe Thr Ser Ile Asp Phe Ser Ser Asn Arg
865                 870                 875                 880 ttt caa gga gcg ata cca gat gct atc ggg aat ctc agc tca ctt tat        2688
Phe Gln Gly Ala Ile Pro Asp Ala Ile Gly Asn Leu Ser Ser Leu Tyr
                885                 890                 895 gtt ctg aat ctg tca cac aat gcc ctt gag gga cca atc cca aaa tcg        2736
Val Leu Asn Leu Ser His Asn Ala Leu Glu Gly Pro Ile Pro Lys Ser
            900                 905                 910
```

-continued

| | |
|---|---|
| att ggg aag cta caa atg ctt gaa tca cta gac ctg tca aca aac cac<br>Ile Gly Lys Leu Gln Met Leu Glu Ser Leu Asp Leu Ser Thr Asn His<br>         915                    920                    925 | 2784 |
| ctg tcc ggg gag atc cca tca gag ctt gca agt ctc aca ttc tta gca<br>Leu Ser Gly Glu Ile Pro Ser Glu Leu Ala Ser Leu Thr Phe Leu Ala<br>930                          935                        940 | 2832 |
| gct ttg aac tta tcg ttc aac aaa ttg ttt ggc aaa att cca tca act<br>Ala Leu Asn Leu Ser Phe Asn Lys Leu Phe Gly Lys Ile Pro Ser Thr<br>945                        950                    955                  960 | 2880 |
| aat cag ttt caa aca ttc tca gca gat tcc ttt gaa gga aac agt ggc<br>Asn Gln Phe Gln Thr Phe Ser Ala Asp Ser Phe Glu Gly Asn Ser Gly<br>                965                    970                    975 | 2928 |
| cta tgc ggg ctc cct ctc aac aac agt tgt caa agc aat ggc tca gcc<br>Leu Cys Gly Leu Pro Leu Asn Asn Ser Cys Gln Ser Asn Gly Ser Ala<br>980                          985                        990 | 2976 |
| tca gag tcc ctg cct cca cca act ccg cta cca gac tca gat gat gaa<br>Ser Glu Ser Leu Pro Pro Pro Thr Pro Leu Pro Asp Ser Asp Asp Glu<br>                995                    1000                  1005 | 3024 |
| tgg gag ttc att ttt gca gca gtt gga tac ata gta ggg gca gca aat<br>Trp Glu Phe Ile Phe Ala Ala Val Gly Tyr Ile Val Gly Ala Ala Asn<br>   1010                       1015                    1020 | 3072 |
| act att tca gtt gtg tgg ttt tac aag cca gtg aag aaa tgg ttt gat<br>Thr Ile Ser Val Val Trp Phe Tyr Lys Pro Val Lys Lys Trp Phe Asp<br>1025                     1030                    1035                  1040 | 3120 |
| aag cat atg gag aaa tgc ttg ctt tgg ttt tca aga aag tga<br>Lys His Met Glu Lys Cys Leu Leu Trp Phe Ser Arg Lys<br>                1045                    1050 | 3162 |
| ttattaaacc cataaataat gagtttattc ttggagtgtt ttgtttaaa taaacaacag | 3222 |
| gataaggaaa atcaagttaa taagctcgca gaacatgatt gttatttcct ttgatgaatg | 3282 |
| tatacaattt tcaatattgg ttcttcaacc ataaccgcag gctaactgtc agttgttgga | 3342 |
| agtcctgaat tttggaaatg acatacattt ttatagtttc | 3382 |

<210> SEQ ID NO 8
<211> LENGTH: 1053
<212> TYPE: PRT
<213> ORGANISM: Lycopersicon esculentum

<400> SEQUENCE: 8

Met Lys Met Met Ala Thr Leu Tyr Phe Pro Met Val Leu Leu Ile Pro
1               5                  10                 15

Ser Phe Gln Ile Leu Ser Gly Tyr His Ile Phe Leu Val Ser Ser Gln
              20                  25                  30

Cys Leu Asp Asp Gln Lys Ser Leu Leu Leu Gln Phe Lys Gly Ser Leu
        35                    40                  45

Gln Tyr Asp Ser Thr Leu Ser Lys Lys Leu Ala Lys Trp Asn Asp Met
50                   55                  60

Thr Ser Glu Cys Cys Asn Trp Asn Gly Val Thr Cys Asn Leu Phe Gly
65              70                  75                  80

His Val Ile Ala Leu Glu Leu Asp Asp Glu Thr Ile Ser Ser Gly Ile
              85                  90                  95

Glu Asn Ser Ser Ala Leu Phe Ser Leu Gln Tyr Leu Glu Ser Leu Asn
        100                    105                  110

Leu Ala Asp Asn Met Phe Asn Val Gly Ile Pro Val Gly Ile Asp Asn
             115                  120                  125

Leu Thr Asn Leu Lys Tyr Leu Asn Leu Ser Asn Ala Gly Phe Val Gly
        130                    135                  140

-continued

```
Gln Ile Pro Ile Thr Leu Ser Arg Leu Thr Arg Leu Val Thr Leu Asp
145                 150                 155                 160

Leu Ser Thr Ile Leu Pro Phe Asp Gln Pro Leu Lys Leu Glu Asn
            165                 170                 175

Pro Asn Leu Ser His Phe Ile Glu Asn Ser Thr Glu Leu Arg Glu Leu
            180                 185                 190

Tyr Leu Asp Gly Val Asp Leu Ser Ser Gln Arg Ser Glu Trp Cys Gln
        195                 200                 205

Ser Leu Ser Leu His Leu Pro Asn Leu Thr Val Leu Ser Leu Arg Asp
    210                 215                 220

Cys Gln Ile Ser Gly Pro Leu Asp Glu Ser Leu Thr Lys Leu His Phe
225                 230                 235                 240

Leu Ser Phe Val Gln Leu Asp Gln Asn Asn Leu Ser Ser Thr Val Pro
                245                 250                 255

Glu Tyr Phe Ala Asn Phe Ser Asn Leu Thr Thr Leu Thr Leu Gly Ser
            260                 265                 270

Cys Asn Leu Gln Gly Thr Phe Pro Glu Arg Ile Phe Gln Val Ser Val
        275                 280                 285

Leu Glu Ser Leu Asp Leu Ser Ile Asn Lys Leu Leu Arg Gly Ser Ile
290                 295                 300

Pro Ile Phe Phe Arg Asn Gly Ser Leu Arg Arg Ile Ser Leu Ser Tyr
305                 310                 315                 320

Thr Asn Phe Ser Gly Ser Leu Pro Glu Ser Ile Ser Asn His Gln Asn
                325                 330                 335

Leu Ser Arg Leu Glu Leu Ser Asn Cys Asn Phe Tyr Gly Ser Ile Pro
            340                 345                 350

Ser Thr Met Ala Asn Leu Arg Asn Leu Gly Tyr Leu Asp Phe Ser Phe
        355                 360                 365

Asn Asn Phe Thr Gly Ser Ile Pro Tyr Phe Arg Leu Ser Lys Lys Leu
    370                 375                 380

Thr Tyr Leu Asp Leu Ser Arg Asn Gly Leu Thr Gly Leu Leu Ser Arg
385                 390                 395                 400

Ala His Phe Glu Gly Leu Ser Glu Leu Val His Ile Asn Leu Gly Asn
                405                 410                 415

Asn Leu Leu Ser Gly Ser Leu Pro Ala Tyr Ile Phe Glu Leu Pro Ser
            420                 425                 430

Leu Gln Gln Leu Phe Leu Tyr Arg Asn Gln Phe Val Gly Gln Val Asp
        435                 440                 445

Glu Phe Arg Asn Ala Ser Ser Pro Leu Asp Thr Val Asp Leu Thr
450                 455                 460

Asn Asn His Leu Asn Gly Ser Ile Pro Lys Ser Met Phe Glu Ile Glu
465                 470                 475                 480

Arg Leu Lys Val Leu Ser Leu Ser Ser Asn Phe Phe Arg Gly Thr Val
                485                 490                 495

Pro Leu Asp Leu Ile Gly Arg Leu Ser Asn Leu Ser Arg Leu Glu Leu
            500                 505                 510

Ser Tyr Asn Lys Leu Thr Val Asp Ala Ser Ser Asn Ser Thr Ser
        515                 520                 525

Phe Thr Phe Pro Gln Leu Asn Ile Leu Lys Leu Ala Ser Cys Arg Leu
        530                 535                 540

Gln Lys Phe Pro Asp Leu Lys Asn Gln Ser Trp Met Met His Leu Asp
545                 550                 555                 560

Leu Ser Asp Asn Gln Ile Leu Gly Ala Ile Pro Asn Trp Ile Trp Gly
```

-continued

```
                    565                 570                 575
Ile Gly Gly Gly Leu Thr His Leu Asn Leu Ser Phe Asn Gln Leu
                580                 585                 590
Glu Tyr Val Glu Gln Pro Tyr Thr Ala Ser Ser Asn Leu Val Leu
            595                 600                 605
Asp Leu His Ser Asn Arg Leu Lys Gly Asp Leu Leu Ile Pro Pro Cys
610                 615                 620
Thr Ala Ile Tyr Val Asn Tyr Ser Ser Asn Leu Asn Asn Ser Ile
625                 630                 635                 640
Pro Thr Asp Ile Gly Lys Ser Leu Gly Phe Ala Ser Phe Phe Ser Val
                645                 650                 655
Ala Asn Asn Gly Ile Thr Gly Ile Ile Pro Glu Ser Ile Cys Asn Cys
            660                 665                 670
Ser Tyr Leu Gln Val Leu Asp Phe Ser Asn Asn Ala Leu Ser Gly Thr
                675                 680                 685
Ile Pro Pro Cys Leu Leu Glu Tyr Ser Thr Lys Leu Gly Val Leu Asn
            690                 695                 700
Leu Gly Asn Asn Lys Leu Asn Gly Val Ile Pro Asp Ser Phe Ser Ile
705                 710                 715                 720
Gly Cys Ala Leu Gln Thr Leu Asp Leu Ser Ala Asn Asn Leu Gln Gly
                725                 730                 735
Arg Leu Pro Lys Ser Ile Val Asn Cys Lys Leu Leu Glu Val Leu Asn
            740                 745                 750
Val Gly Asn Asn Arg Leu Val Asp His Phe Pro Cys Met Leu Arg Asn
            755                 760                 765
Ser Asn Ser Leu Arg Val Leu Val Leu Arg Ser Asn Lys Phe Tyr Gly
            770                 775                 780
Asn Leu Met Cys Asp Val Thr Arg Asn Ser Trp Gln Asn Leu Gln Ile
785                 790                 795                 800
Ile Asp Ile Ala Ser Asn Asn Phe Thr Gly Val Leu Asn Ala Glu Phe
                805                 810                 815
Phe Ser Asn Trp Arg Gly Met Met Val Ala Asp Asp Tyr Val Glu Thr
                820                 825                 830
Gly Arg Asn His Ile Gln Tyr Glu Phe Leu Gln Leu Ser Lys Leu Tyr
            835                 840                 845
Tyr Gln Asp Thr Val Thr Leu Thr Ile Lys Gly Met Glu Leu Glu Leu
850                 855                 860
Val Lys Ile Leu Arg Val Phe Thr Ser Ile Asp Phe Ser Ser Asn Arg
865                 870                 875                 880
Phe Gln Gly Ala Ile Pro Asp Ala Ile Gly Asn Leu Ser Ser Leu Tyr
                885                 890                 895
Val Leu Asn Leu Ser His Asn Ala Leu Glu Gly Pro Ile Pro Lys Ser
            900                 905                 910
Ile Gly Lys Leu Gln Met Leu Glu Ser Leu Asp Leu Ser Thr Asn His
            915                 920                 925
Leu Ser Gly Glu Ile Pro Ser Glu Leu Ala Ser Leu Thr Phe Leu Ala
            930                 935                 940
Ala Leu Asn Leu Ser Phe Asn Lys Leu Phe Gly Lys Ile Pro Ser Thr
945                 950                 955                 960
Asn Gln Phe Gln Thr Phe Ser Ala Asp Ser Phe Glu Gly Asn Ser Gly
                965                 970                 975
Leu Cys Gly Leu Pro Leu Asn Asn Ser Cys Gln Ser Asn Gly Ser Ala
            980                 985                 990
```

```
Ser Glu Ser Leu Pro Pro Pro Thr Pro Leu Pro Asp Ser Asp Asp Glu
        995                 1000                1005

Trp Glu Phe Ile Phe Ala Ala Val Gly Tyr Ile Val Gly Ala Ala Asn
    1010                1015                1020

Thr Ile Ser Val Val Trp Phe Tyr Lys Pro Val Lys Lys Trp Phe Asp
1025                1030                1035                1040

Lys His Met Glu Lys Cys Leu Leu Trp Phe Ser Arg Lys
                1045                1050

<210> SEQ ID NO 9
<211> LENGTH: 24
<212> TYPE: PRT
<213> ORGANISM: Lycopersicon esculentum
<220> FEATURE:
<223> OTHER INFORMATION: leucine-rich repeat consensus sequence
<220> FEATURE:
<223> OTHER INFORMATION: X is any of the 20 standard amino acids

<400> SEQUENCE: 9

Xaa Xaa Ile Xaa Asn Leu Xaa Xaa Leu Xaa Xaa Leu Xaa Leu Ser Xaa
 1               5                  10                  15

Asn Xaa Leu Ser Gly Xaa Ile Pro
            20

<210> SEQ ID NO 10
<211> LENGTH: 3477
<212> TYPE: DNA
<213> ORGANISM: Lycopersicon esculentum
<220> FEATURE:
<221> NAME/KEY: misc_feature
<222> LOCATION: (1)..(3477)
<223> OTHER INFORMATION: Ve1.1 Ve.1.2 promoter region

<400> SEQUENCE: 10
tacctaataa aatttgcaaa aagggtatga tgaagaagat ccatagaaag tgtaaaaatc      60
tcattgctta agtcttggag gaattataat ccatcaaact tgttgttttt tctactttgg    120
gattgaaatg aagggagaag gtagaaaaga agataaataa tgaggggaag aaatggtcaa    180
aagaaaaaca tgacaagtgc ttggttgttt aattttatgt atttgcagat tgtattgttt    240
ctttctacgc gttttatgt cgggcctatt tgtttattgg tttggtgact ttgaatatac    300
ttaaagaaaa tactaatcaa aaccatgact tttttgcat ttgtttgaat ttatatttat    360
gatttaggag tttctattct aagtgtgggg ttggctgttt accatgggat tctctcacat    420
gcaaggtttt gattactact tatatatttc accattggtc caaataagt attttttaata   480 ctccaacaat aatattaaac aaaaacaaga actgtgttga tttcatacca tgaacagatg    540
tgacttgtgt gtgtgttttt tttaaaaaaa aatcttagta gcacttgtaa tcattcacca    600
tatttattta tttttgtctt ttttcctatt tgattagta aattgatatt attaataaaa     660
ttaaaaatgt acctattgta acagtaagaa tatatagatg aataataaat tgaagaagag    720
gtatggacag gagtgatttg taataattga aataattgtt agaaaatatt ttttatata    780 tttattaaaa atagaaactt gacgataaaa agtcaatagc agtccatttt caaaaatagg    840
gaaattacgc atttctttaa aggaagcaat tgccagacag ccaaccatct tctttagaaa    900
attgtggctg accctaccta ctagaaaaag gttatgatga cacgaaattc gcgaaattta    960 agatttttt taaaaataaa tatatattaa tattataata ttacttacgt agttatttag   1020
tgttaagtat aaagatataa taatctcgag aattattctt tgtttggttg gatgtttaat  1080
```

-continued

```
aaatcttgaa taatttattc aatatttata tcttagtgat ggaacaagtt actcatatag   1140
aagataactt attcttgatt ccaaccaaat tatagaatat ctaaggatga aataaaaaat   1200
tttaaaaata aaaatatatc cttttttaaaa tgaatttaca tgtaaagggt atcacatatt   1260
aatttacgat ataatatcgg agaaggaaaa ataagaaaat tctaagagaa aataatatg    1320 ccaagttgtt ttgctattca gaacgggaaa atgttaatta attttatagg tgtgataaaa   1380
ttaaataagt aaacttatta taaaaataaa taataagttt gattggattg taacgaactt   1440
gaataacgta attatataaa tatttttataa tgattatata gactaattgt gttctaccaa  1500
acatgttcca attatgcttc agccgataaa attgaattta ataggtgaga cagagagttg   1560
gttgttatcg ttttaagtaa tattctacgt cattttaata agtttaaaat tccgagcata   1620
gaaaactgaa taaaatagaa aaaattatag caatttttat gggtcctcct agctgaagtt   1680
ggtgttttgt tatttttttc ttatgcatgt gaatctcaat aatataggtg aaaatcaatt   1740
ttgttctttt tcctaatact aagtaagggg ttgttgtata taaagatgtt tggcgtgcaa   1800
caataccttg caattataaa aatactaatt agaaagcaat aactggtttt ttcggatatt   1860
caataaagtt gaaacgatat aaagaaaatt agtgtgactt ttactcaaga atgacataca   1920
cgaattgaga aattgtttaa tttattttta aaaaagaaa gaaattagcc tactagtttt     1980
ctacgtgatt gattttttttt ttggtatgtc ttttttgttga cttactcaat gttttgcaga   2040
aatccataga ttaactaaca aaaacttgca atttcagcag tcccctgtca acatgaaaaa   2100
taattcaata tacggagtta ttcgctaaag cggaggctat gattcatctg aacccttttc   2160
aacgaaaaat tacactatga caaatttatt ctaaaccggt gtatcatttt catgaatgaa   2220
gcaagaccaa agaggagact tccacaagtg ttgtgcagga gtcaatgaat gagaatcttc   2280
agagtcttct acacaatgaa ccaaaggggc taacatcaaa cgaggagact aggaggtaat   2340
tcaatctcta caaatacata attattttttt cgcatttttt tatacgtgatt aaaattatac   2400 tttgtgtgta tataaaaaat attaaacagt aaatttaagt taaaggtata aatcaaaata   2460
acttccactc atatataggc cataaatgag gtaattaatt ttcatcatat ttataaaaat   2520
atctcctttc acacttgaaa gtgatcattt agttgactgt tgatagaaca taagccttac   2580
ccagaaaatg acagattgtt gatgatcaaa tacactaaat tacattatag tagttatgta   2640
aaatatcgta ctaaacacaa cattaattaa aagtagaaaa aaagagtgga ataacaagca   2700
ctcgagtaga aaaataaatc atccttccta taagtgtttt gctatccggt taaataaata   2760
tatatgtata ttaatttatg aaccaccaat aaaattgatt gttggcttaa tggtaagtaa   2820
ggacccttat aaatgcttcc cacaccagtg ttttaaaaaa aggaaacatg ttttgcaata   2880
tttttctctt tctatcctaa agttagaatt ctcaaacaac ttctgtagtt acaattacaa   2940
cctttcggaa atatccaata aaattgaaac gatacacaaa agattagcat gacctttact   3000
caaagatgac gacatataca aattgagaaa tgattaaaca gagaaattaa aacaaagaag   3060
aaagaaataa gcctactatt tttctacacg gttgaatgtt cttcttcttc taattttttc   3120
ttgtggaatt tctacatctt tttttttaa atttttggtc tccaactaaa ccagccccag   3180
tttggctagt gctattttttt ttttgttgac tctagtggaa gtctcctaaa tttttctctt   3240
cctctggtct tttggtagat tcaagttttt aaaaagtcag aaatgtatca cagtagtact   3300
tagatatgaa aattctaacc atacaattcc aatcatatta acaatttcat aaatgaagca   3360
agaccaaaga ggagacttca agtcttcca cagaatgaac caaaagggct aacaacaaac   3420 aagttttttaa gttccttcga actgcataac tgagtcatat tcaagctaac aagttgc     3477
```

```
<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence:PCR forward
      primer 3B2F4

<400> SEQUENCE: 11
aattcactca acgggagcct tcctgc                                             26

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:PCR reverse
      primer 3B2R4

<400> SEQUENCE: 12
tcaaggcatt gttagagaaa tcaa                                               24

<210> SEQ ID NO 13
<211> LENGTH: 982
<212> TYPE: DNA
<213> ORGANISM: Solanum chacoense
<220> FEATURE:
<221> NAME/KEY: misc_feature
<222> LOCATION: (1)..(982)
<223> OTHER INFORMATION: Vc partial genomic DNA sequence
<220> FEATURE:
<221> NAME/KEY: CDS
<222> LOCATION: (2)..(982)

<400> SEQUENCE: 13 c atg att acg cca agc tat tta ggg aca tat aga ata ctc aag cta tgc        49
  Met Ile Thr Pro Ser Tyr Leu Gly Thr Tyr Arg Ile Leu Lys Leu Cys
    1               5                  10                  15 atc caa cgc gtg ggg gag ctc tcc cat atg gtc gac ctg cag gcg ncc          97
Ile Gln Arg Val Gly Glu Leu Ser His Met Val Asp Leu Gln Ala Xaa
                 20                  25                  30 gcg aat tca cta gtg att aat tca ctc aac ggg agc ctt cct gca tgt         145
Ala Asn Ser Leu Val Ile Asn Ser Leu Asn Gly Ser Leu Pro Ala Cys
             35                  40                  45 atc ttt gag ctt ccc tcc ttg cag acg ctt tta ctt aac agc aat caa         193
Ile Phe Glu Leu Pro Ser Leu Gln Thr Leu Leu Leu Asn Ser Asn Gln
     50                  55                  60 ttt gtt ggc caa gtc aac cat ttt cac aat gca tcc tcc ttt ctc gat         241
Phe Val Gly Gln Val Asn His Phe His Asn Ala Ser Ser Phe Leu Asp
 65                  70                  75                  80 gaa att gat ttg agc aac aac caa ctg aat ggt tca att ccc aag tcc         289
Glu Ile Asp Leu Ser Asn Asn Gln Leu Asn Gly Ser Ile Pro Lys Ser
                 85                  90                  95 atg ttt gac gtt ggg agg ctt aag gtt ctc tca ctt tct tcc aat ttc         337
Met Phe Asp Val Gly Arg Leu Lys Val Leu Ser Leu Ser Ser Asn Phe
            100                 105                 110 ttt agc gga aca gta ccc ctt gac ctc att ggg aag ctg agc aat ctt         385
Phe Ser Gly Thr Val Pro Leu Asp Leu Ile Gly Lys Leu Ser Asn Leu
         115                 120                 125 tca cga ctg gag ctt tct tac aat aac ttg act gtt gat gca agt agc         433
Ser Arg Leu Glu Leu Ser Tyr Asn Asn Leu Thr Val Asp Ala Ser Ser
    130                 135                 140 agt aat tca gac tct ttc aca ttt ccc cag ttg aac ata ttg aaa cta         481
```

```
Ser Asn Ser Asp Ser Phe Thr Phe Pro Gln Leu Asn Ile Leu Lys Leu
145                 150                 155                 160 gct tcg tgt cgg ctg caa aag ttt cct gat ctt aaa aat cag tca agg      529
Ala Ser Cys Arg Leu Gln Lys Phe Pro Asp Leu Lys Asn Gln Ser Arg
                165                 170                 175 atg atc caa tta gac ctt tct gac aac aaa ata ctg ggg gca ata cca      577
Met Ile Gln Leu Asp Leu Ser Asp Asn Lys Ile Leu Gly Ala Ile Pro
            180                 185                 190 aat tgg att tgg cga ata ggt aac gga gct ctg agt cac ctg aat ctt      625
Asn Trp Ile Trp Arg Ile Gly Asn Gly Ala Leu Ser His Leu Asn Leu
        195                 200                 205 tct ttc aat cag ttg gag tac gtg gaa cag cct tac aat gtt tcc aga      673
Ser Phe Asn Gln Leu Glu Tyr Val Glu Gln Pro Tyr Asn Val Ser Arg
210                 215                 220 tat ctt gtc gtc ctt gac ttg cat tcc aat aag cta aag ggt gac cta      721
Tyr Leu Val Val Leu Asp Leu His Ser Asn Lys Leu Lys Gly Asp Leu
225                 230                 235                 240 cca att cca cct tcc ttt gct gca tat ttg gac tac tcg agc aat aat      769
Pro Ile Pro Pro Ser Phe Ala Ala Tyr Leu Asp Tyr Ser Ser Asn Asn
                245                 250                 255 ttc agc aat tcc atc cca cta gat att ggc aat tat ctt ggt ttt gcc      817
Phe Ser Asn Ser Ile Pro Leu Asp Ile Gly Asn Tyr Leu Gly Phe Ala
            260                 265                 270 tcc ttt ttc tcg gta gca aac aat ggc att act gga aga att ccc gaa      865
Ser Phe Phe Ser Val Ala Asn Asn Gly Ile Thr Gly Arg Ile Pro Glu
        275                 280                 285 tcc ata tgc aat gtc agc tac ctt caa gtt ctt gat ttc tct aac aat      913
Ser Ile Cys Asn Val Ser Tyr Leu Gln Val Leu Asp Phe Ser Asn Asn
    290                 295                 300 gcc ttg aaa tcg aat tcc cgc ggc cgc cat ggc ggc cgg gag cat gcg      961
Ala Leu Lys Ser Asn Ser Arg Gly Arg His Gly Gly Arg Glu His Ala
305                 310                 315                 320 acg tcg ggc cca att cgc cct                                          982
Thr Ser Gly Pro Ile Arg Pro
                325
```

<210> SEQ ID NO 14
<211> LENGTH: 327
<212> TYPE: PRT
<213> ORGANISM: Solanum chacoense

<400> SEQUENCE: 14

```
Met Ile Thr Pro Ser Tyr Leu Gly Thr Tyr Arg Ile Leu Lys Leu Cys
 1               5                  10                  15

Ile Gln Arg Val Gly Glu Leu Ser His Met Val Asp Leu Gln Ala Xaa
            20                  25                  30

Ala Asn Ser Leu Val Ile Asn Ser Leu Asn Gly Ser Leu Pro Ala Cys
        35                  40                  45

Ile Phe Glu Leu Pro Ser Leu Gln Thr Leu Leu Asn Ser Asn Gln
    50                  55                  60

Phe Val Gly Gln Val Asn His Phe His Asn Ala Ser Ser Phe Leu Asp
65                  70                  75                  80

Glu Ile Asp Leu Ser Asn Asn Gln Leu Asn Gly Ser Ile Pro Lys Ser
                85                  90                  95

Met Phe Asp Val Gly Arg Leu Lys Val Leu Ser Leu Ser Ser Asn Phe
            100                 105                 110

Phe Ser Gly Thr Val Pro Leu Asp Leu Ile Gly Lys Leu Ser Asn Leu
        115                 120                 125
```

```
-continued

Ser Arg Leu Glu Leu Ser Tyr Asn Asn Leu Thr Val Asp Ala Ser Ser
    130             135             140

Ser Asn Ser Asp Ser Phe Thr Phe Pro Gln Leu Asn Ile Leu Lys Leu
145             150             155             160

Ala Ser Cys Arg Leu Gln Lys Phe Pro Asp Leu Lys Asn Gln Ser Arg
            165             170             175

Met Ile Gln Leu Asp Leu Ser Asp Asn Lys Ile Leu Gly Ala Ile Pro
        180             185             190

Asn Trp Ile Trp Arg Ile Gly Asn Gly Ala Leu Ser His Leu Asn Leu
        195             200             205

Ser Phe Asn Gln Leu Glu Tyr Val Glu Gln Pro Tyr Asn Val Ser Arg
    210             215             220

Tyr Leu Val Val Leu Asp Leu His Ser Asn Lys Leu Lys Gly Asp Leu
225             230             235             240

Pro Ile Pro Pro Ser Phe Ala Ala Tyr Leu Asp Tyr Ser Ser Asn Asn
            245             250             255

Phe Ser Asn Ser Ile Pro Leu Asp Ile Gly Asn Tyr Leu Gly Phe Ala
            260             265             270

Ser Phe Phe Ser Val Ala Asn Asn Gly Ile Thr Gly Arg Ile Pro Glu
        275             280             285

Ser Ile Cys Asn Val Ser Tyr Leu Gln Val Leu Asp Phe Ser Asn Asn
    290             295             300

Ala Leu Lys Ser Asn Ser Arg Gly Arg His Gly Gly Arg Glu His Ala
305             310             315             320

Thr Ser Gly Pro Ile Arg Pro
                325
```